(12) United States Patent
Yang et al.

(10) Patent No.: US 12,268,665 B2
(45) Date of Patent: Apr. 8, 2025

(54) COMBINATION OF IMMUNOTHERAPIES WITH MDM2 INHIBITORS

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Douglas Dong Fang, Suzhou (CN); Qiuqiong Tang, Suzhou (CN)

(73) Assignee: ASCENTAGE PHARMA (SUZHOU) CO., LTD, Suzhou (CN)

( * ) Notice: Subject to any disclaimer, the term of this patent is extended or adjusted under 35 U.S.C. 154(b) by 428 days.

(21) Appl. No.: 16/618,794

(22) PCT Filed: Aug. 7, 2019

(86) PCT No.: PCT/CN2019/099664
§ 371 (c)(1),
(2) Date: Dec. 2, 2019

(87) PCT Pub. No.: WO2020/030016
PCT Pub. Date: Feb. 13, 2020

(65) Prior Publication Data
US 2022/0175725 A1    Jun. 9, 2022

Related U.S. Application Data

(60) Provisional application No. 62/853,069, filed on May 27, 2019.

(30) Foreign Application Priority Data

Aug. 8, 2018  (WO) ............... PCT/CN2018/099280
Dec. 28, 2018  (WO) ............... PCT/CN2018/124866
Jan. 29, 2019  (WO) ............... PCT/CN2019/073720

(51) Int. Cl.
*A61K 31/407* (2006.01)
*A61K 39/395* (2006.01)
*A61P 35/00* (2006.01)

(52) U.S. Cl.
CPC ........ *A61K 31/407* (2013.01); *A61K 39/3955* (2013.01); *A61P 35/00* (2018.01)

(58) Field of Classification Search
CPC .... A61P 35/00; A61K 31/407; A61K 39/3955
See application file for complete search history.

(56) References Cited

U.S. PATENT DOCUMENTS 9,745,314 B2    8/2017 Wang et al.

FOREIGN PATENT DOCUMENTS

| CN | 106794171 A | 5/2017 |
| CN | 107206071 A | 9/2017 |
| WO | 2015/161032 A1 | 10/2015 |

OTHER PUBLICATIONS

T R Golub et al. Molecular Classification of Cancer . . . Science vol. 286 Oct. 15, 1999, p. 531-537 (Year: 1999).*
Le et al. N Engl J Med. Jun. 25, 2015; 372(26): 2509-2520). (Year: 2015).*
Wu et al. Pseudoprogression and hyperprogression after checkpoint blockade, International Immunopharmacology, 2018, p. 125-135 (Year: 2018).*
Hui Qin Wang, et al., "Abstract 5560: PD-1/PD-L1 blockade enhances MDM2 inhibitor activity in p53 wild-type cancers", AACR Annual Meeting 2018; Apr. 14-18, 2018, Chicago, IL., vol. 78, Issue 13. Suppl. DOI: 10.1158/1538-7445.AM2018-5560.
Dorothea Rudolph, et al., "BI 907828: a novel, potent MDM2 inhibitor that induces anti-tumor immunological memory and acts synergistically with an anti-PD1 antibody in syngeneic mouse models of cancer", AACR Annual Meeting 2018; Apr. 14-18, 2018, Chicago, USA.
Angelo Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development". Journal of Medicinal Chemistry(2017), vol. 60, received on Nov. 17, 2016 (Nov. 17, 2016), 2819-2839.
Guo, G. et al., "Local Activation of p53 in the Tumor Microenvironment Overcomes Immune Suppression and Enhances Antitumor Immunity", Cancer Research (Mar. 2017), vol. 77(9), pp. 2292.
Wu, X. et al., "The p53-mdm-2 autoregulatory feedback loop", Genes & Development (1993), vol. 7, pp. 1126-1132.
Mockler, M. B. et al., "Targeting T Cell Immunometabolism for Cancer Immunotherapy; Understanding the Impact of the Tumor Microenvironment", Frontiers in Oncology (May 2014), vol. 4:107.
Pearce, E. L. et al., "Fueling Immunity: Insights into Metabolism and Lymphocyte Function", Science (Oct. 2013), vol. 342(6155): 1242454.
Dröge, W. et al., "Regulation of T-cell functions by I-lactate", Cellular Immunology (1987), vol. 108, pp. 405-416.

(Continued)

*Primary Examiner* — Kortney L. Klinkel
*Assistant Examiner* — Richard Grant Peckham
(74) *Attorney, Agent, or Firm* — Jun He Law Offices P.C.; James J . Zhu

(57) ABSTRACT

Disclosed herein are combination therapies comprising an effective amount of a modulator of the immune checkpoint molecule; and an effective amount of a MDM2 inhibitor.

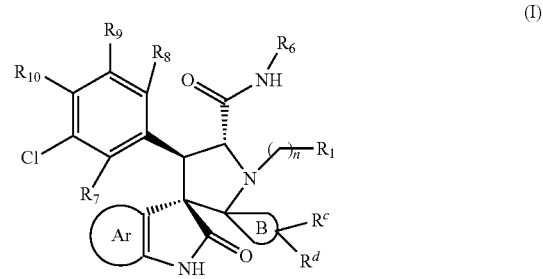

13 Claims, 30 Drawing Sheets

(56) References Cited

OTHER PUBLICATIONS

Fischer, K. et al., "Inhibitory effect of tumor cell-derived lactic acid on human T cells", Blood (May 2007), vol. 109(9), pp. 3812-3819.
Ledderose, C. et al., "Mitochondria are gate-keepers of T cell function by producing the ATP that drives purinergic signaling", Journal of Biological Chemistry (2014), vol. 289, No. 37, pp. 25936-25945.
Sena, L. A. et al., "Mitochondria Are Required for Antigen-Specific T Cell Activation through Reactive Oxygen Species Signaling", Immunity (Feb. 2013), vol. 38(2), pp. 225-236.
Harris, T. J. et al., "Primer on tumor immunology and cancer immunotherapy", Journal for Immuno Therapy of Cancer (2013), vol. 1, pp. 12.
Chen, D. S. et al., "Oncology Meets Immunology: The Cancer-Immunity Cycle", Immunity (Jul. 2013), vol. 39, pp. 1-10.
Pardoll, D. M. et al., "The blockade of immune checkpoints in cancer immunotherapy", Nat. Rev. Cancer (2012), vol. 12(4), pp. 252-264.
Sharma, P. et al., "Immune Checkpoint Targeting in Cancer Therapy: Toward Combination Strategies with Curative Potential", Cell (Apr. 2015), vol. 161, pp. 205-214.
Martinez-Forero, I. et al., "T Cell Costimulation with Anti-CD137 Monoclonal Antibodies Is Mediated by K63-Polyubiquitin-Dependent Signals from Endosomes", The Journal of Immunology (2013), vol. 190(12), pp. 6694-6706.
Dubrot, J. et al., "Treatment with anti-CD137 mAbs causes intense accumulations of liver T cells without selective antitumor immunotherapeutic effects in this organ", Cancer Immunol. Immunother. (2010), vol. 59, pp. 1223-1233.
Cheng, Q. et al., "ATM activates p53 by regulating MDM2 oligomerization and E3 processivity", The EMBO Journal (2009), vol. 28, pp. 3857-3867.
Maya, R. et al., "ATM-dependent phosphorylation of Mdm2 on serine 395: role in p53 activation by DNA damage", Genes & Development (2001), vol. 15, pp. 1067-1077.
A Study of APG-115 in Combination With Pembrolizumab in Patients With Metastatic Melanomas or Advanced Solid Tumors, NCT03611868, retrieved from https://clinicaltrials.gov/ct2/show/NCT03611868,on Apr. 26, 2020. Published on Aug. 2, 2018. p. 1-8.
APG-115 in Patients With Advanced Solid Tumors or Lymphomas (APG-115), NCT02935907, retrieved from https://clinicaltrials.gov/ct2/show/NCT02935907, on Apr. 26, 2020. Published on Oct. 18, 2016. p. 1-7.
Tolcher, A.W., et al., "A phase Ib/II study of APG-115 in combination with pembrolizumab in patients with unresectable or metastatic melanomas or advanced solid tumors", Annals of Oncology 30 (Supplement 1): i2-i3, 2019. doi: 10.1093/annonc/mdz027.
Zhang, X. et al., "A phase I study of a novel MDM2-P53 antagonist APG-115 in Chinese patients with advanced soft tissue sarcomas", Journal of Clinical Oncology (May 2019), vol. 37(15_suppl), pp. 3124-3124. p. 1-6.
Rasco, D. W. et al., "A phase I study of a novel MDM2 antagonist APG-115 in patients with advanced solid tumors", Journal of Clinical Oncology (May 2019), vol. 37(15_suppl), pp. 3126-3126.
Rudolph, D. et al., "Abstract 4866: BI 907828: A novel, potent MDM2 inhibitor that induces antitumor immunologic memory and acts synergistically with an anti-PD-1 antibody in syngeneic mouse models of cancer", Experimental and Molecular Therapeutics (Jul. 2018). Proceedings: AACR Annual Meeting 2018, Chicago, IL, pp. 4866-4866. p. 1-2. DOI:10.1158/1538-7445.
A Phase I Study of APG-115 Capsules in Patients with Advanced Solid Tumors, CTR20170975, published on Nov. 20, 2017.

* cited by examiner

Figure 3A
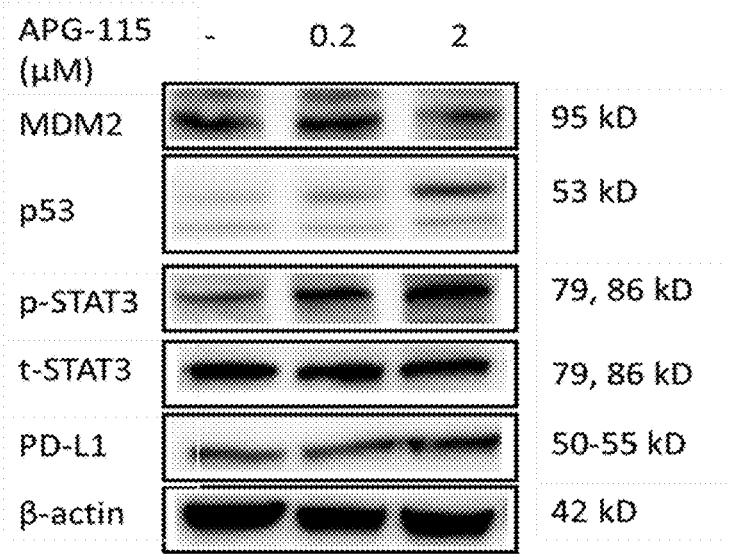
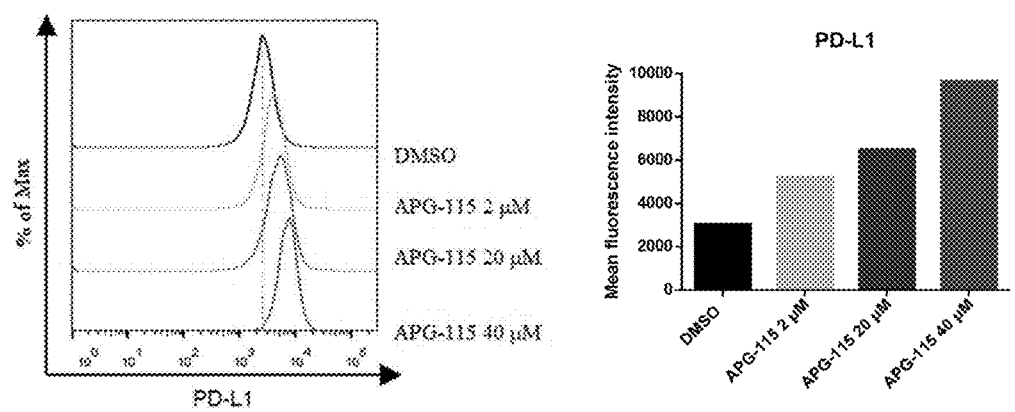
Figure 3B

A p53$^{wt}$ MH-22A

B p53$^{mut}$ MC38

Enhanced antitumor activity of anti-PD-1 therapy
by combination with APG-115.

(a)

(b)

APG-115 Pharmacokinetics in Plasma (a)

(b)

Serum MIC-1 levels were elevated (a)

(b)

APG-115 Pharmacokinetics in Plasma (a)

Serum MIC-1 levels were elevated

COMBINATION OF IMMUNOTHERAPIES WITH MDM2 INHIBITORS

FIELD OF THE INVENTION

The present invention relates to combination immunotherapies with MDM2 inhibitors to treat conditions and diseases wherein inhibition of MDM2 and MDM2-related proteins provides a benefit.

BACKGROUND OF THE INVENTION

MDM2 inhibitors interfere the binding of MDM2 oncoprotein with the tumor suppressor p53 protein, which thereby serves as a pharmacological p53 activator. Emerging evidence suggests that p53 dysfunction also fuels inflammation and supports tumor immune evasion and, thus, p53 dysfunction serves as an immunological driver of tumorigenesis (Guo G, Cancer Research, 2017; 77(9):2292).

MDM2 and p53 are part of an auto-regulatory feed-back loop (Wu et al., *Genes Dev.* 7:1126 (1993)). MDM2 is transcriptionally activated by p53 and MDM2, in turn, inhibits p53 activity by at least three mechanisms (Wu et al., *Genes Dev.* 7:1126 (1993)). First, MDM2 protein directly binds to the p53 transactivation domain, and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

APG-115 is a novel, bioavailable, highly potent MDM2 inhibitor.

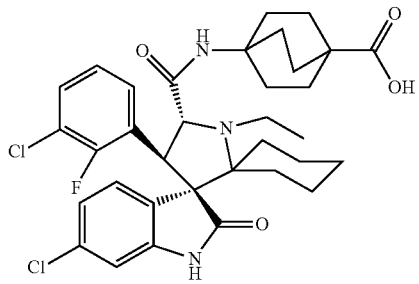

APG-115 is currently in clinical trials in patients with advanced solid tumor or lymphomas (NCT02935907). Given the potency of APG-115, it would be advantageous to further enhance the efficacy of this drug candidate in cancer treatment.

SUMMARY OF THE INVENTION

It has now been found by the inventors of the present application that the administration of a MDM2 inhibitor or a pharmaceutically acceptable salt thereof and a modulator of an immune checkpoint molecule (e.g., an activator of a co-stimulatory molecule or an inhibitor of an immune checkpoint molecule) synergistically treats cancer. In particular, as demonstrated in Examples 1-3 disclosed herein, it is surprising to find that the addition of a MDM2 inhibitor (e.g., APG-115) enhanced efficacy of immunotherapy (e.g., anti PD-1 therapy), leading to an increase in response rated, more complete regression (CR) responders, delayed tumor growth, as well as conversion of resistance tumors into responding ones.

Accordingly, provided herein are methods of treating cancer in a subject, by administering to the subject in need thereof: a) an effective amount of a modulator of an immune checkpoint molecule; and b) an effective amount of a MDM2 inhibitor, wherein the MDM2 inhibitor is represented by the following formula (formula (I)):

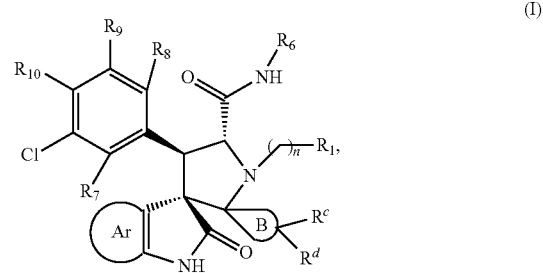

or a pharmaceutically acceptable salt thereof, the definitions of each variable are provided herein.

In another aspect, provided herein are methods of treating cancer in a subject, by administering to the subject in need thereof an effective amount of a MDM2 inhibitor represented by the following formula (formula (I)):

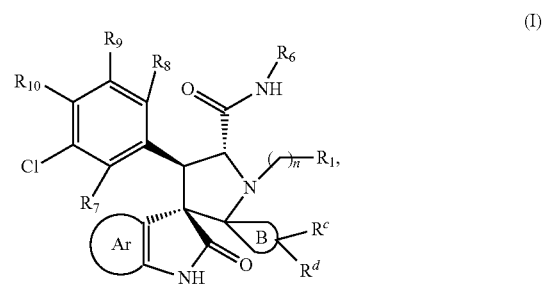

or a pharmaceutically acceptable salt thereof, the definitions of each variable are provided herein.

The cancer can be treated in the claimed invention is selected from the group consisting of adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, choriocarcinoma, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, head and neck cancer, hepatoma cancer, Hodgkin disease, Kaposi sarcoma, kidney cancer, laryngeal and hypopharyngeal cancer, leukemia—acute lymphocytic (ALL) in adults, leukemia—acute myeloid (AML), leukemia—chronic lymphocytic (CLL), leukemia—chronic myeloid (CML), leukemia—chronic myelomonocytic (CMML), leukemia in children, liver cancer, lung cancer—non-small cell, lung cancer—small cell, lung carcinoid tumor, lymphoma of the skin, malignant mesothelioma, Merkel cell carcinoma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer—basal and squamous cell, skin cancer—melanoma, small intestine cancer, stomach cancer, testicular cancer, thymus cancer, thyroid cancer, uterine sarcoma, urothelial carcinoma, vaginal cancer, vulvar cancer, Waldenstrom macroglobulinemia, and Wilms Tumor.

In certain embodiments, the cancer is selected from pancreatic cancer, adenoid cystic carcinoma, lung cancer, gastrointestinal stromal tumor, and breast cancer. In certain embodiments, the cancer is locally advanced or metastatic solid tumor or lymphoma. In certain embodiments, the subject is treatment-experienced and shows disease progression.

Also provided herein are pharmaceutical compositions comprising a) an effective amount of a modulator of an immune checkpoint molecule; and b) an effective amount of a MDM2 inhibitor, wherein the MDM2 inhibitor is represented by the following formula:

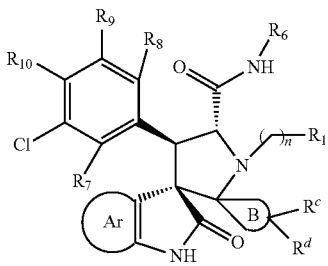

or a pharmaceutically acceptable salt thereof, the definitions of each variable are provided herein.

Also provided herein is the use of a) an effective amount of a modulator of an immune checkpoint molecule; and b) an effective amount of a MDM2 inhibitor of formula (I) disclosed herein, or a pharmaceutically acceptable salt thereof, for the preparation of a medicament for the treatment of cancers.

In another embodiment, provided herein a combination of a) an effective amount of a modulator of an immune checkpoint molecule; and b) an effective amount of a MDM2 inhibitor of formula (I) disclosed herein, or a pharmaceutically acceptable salt thereof, for use in treating cancers.

BRIEF DESCRIPTION OF THE DRAWINGS

FIG. 3A shows expression levels of MDM2, p53, total STAT3 (t-STAT3), phosphorylated STAT3 (p-STAT3), PD-L1, and β-actin (loading control) expression after MH-22A cells were treated with indicated doses of APG-115 for 72 h. FIG. 3B shows PD-L1 expression levels with different doses of APG-115.

DETAILED DESCRIPTION OF THE INVENTION

Figure 1:
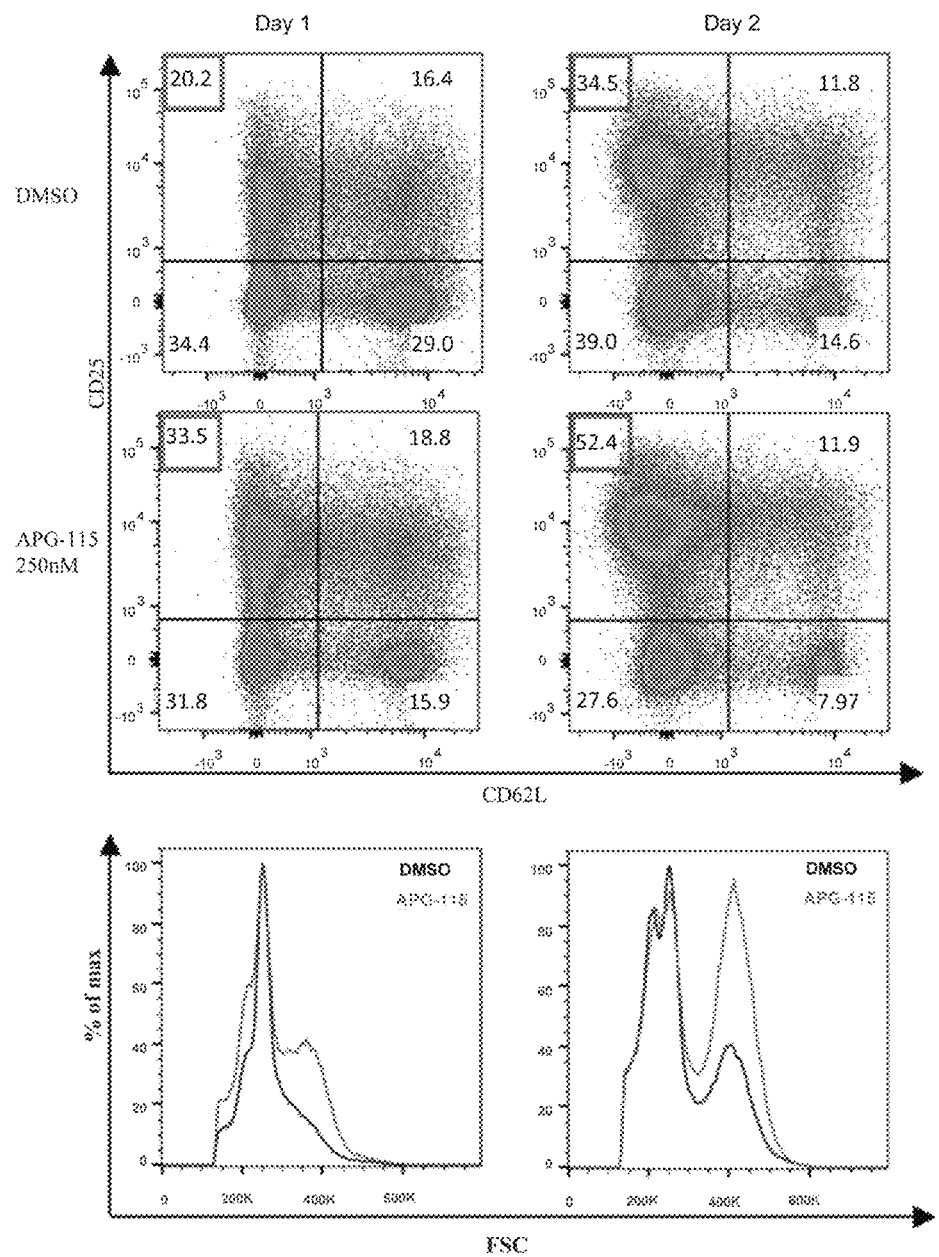
FIG. 1 shows that APG-115 enhanced mouse CD4$^+$ T cell activation.

Described herein are combination therapies using MDM2 inhibitors and modulators of immune checkpoint molecules (also referred to as "immune checkpoint modulators" herein)

for treatment of cancer. Immune checkpoint modulators can target checkpoint molecules that modulate antitumor immune responses.

The immune checkpoint modulator (e.g., an activator or an inhibitor) therapies approved to date have demonstrated clinical responses in multiple tumor types and are continuously being evaluated for broader utility. However, in spite of the remarkable responses observed in multiple cancers in response to targeting a single checkpoint on immune cells, the durability of response has been observed only in a fraction of patients. Efforts are currently focused on targeting multiple checkpoints using combination therapy based on the bifurcation in T cell pathways targeted by various immunotherapies to improve durable anti-tumor responses in the clinical setting. Clinical trials of combination therapies are ongoing with long term patient outcomes yet to be determined. See Sharma et al., cited above.

T cell mediated immune responses involve a sequence of events that require clonal selection of antigen specific cells, their activation and proliferation, transport to the site of the antigen and elicitation of immune response. See Mockler et al., 2014, Frontiers in Oncol 4:1; and Pearce et al., 2013, Science 342(6155):1242454, each of which is incorporated by reference herein. Upon receiving T cell receptor and co-stimulatory signals, T cells develop in growth, expansion and differentiation into cytotoxic, regulatory, or helper T cells. Depending on their stage of activation, T cells display distinct metabolic profiles. See Mockler et al., 2014, Front. Oncol. 4: 107, which is incorporated by reference herein in its entirety. Naïve T cells are metabolically quiescent adopting a basal level of nutrient uptake and rely on oxidative phosphorylation as a primary source for ATP production. In contrast, activated T cells (effector T cells) adopt an anabolic metabolic profile to guarantee increased energy supplies needed for cell growth, proliferation, differentiation, and effector functions. Effector T cells preferentially use glycolysis over oxidative phosphorylation for ATP production, therefore consuming high amounts of glucose. Contrary to naïve T cells and effector T cells, the long lifespan of memory T cells poses a different metabolic demand. Transition to the memory stage is characterized by a quiescent metabolism with an increased reliance on fatty acid oxidation to fuel oxidative phosphorylation. In summary, each stage of T cell development requires metabolic support via production of energy and generation of biosynthetic precursors. Thus it is critical that T cells undergo appropriate activation and differentiation to maintain homeostasis.

T cells in tumors, so-called tumor infiltrating lymphocytes (TILs) have been shown to be key denominators for overall survival in solid cancer bearing patients. The tumor microenvironment is hostile to T cell function, e.g. due to expression of enzymes that deplete the amino acids tryptophan and arginine and the presence of innate cells or regulatory T cells which both have suppressive activity. Moreover, cancer cells are characterized by an altered metabolism, glycolysis, in which glucose is metabolized to lactate which is secreted to the microenvironment rather than further metabolized in the mitochondria. This altered metabolism is governed by activated oncogenes and/or hypoxia. Lactate negatively impacts the function of immune cells and it is detrimental to T cell function, cytokine production and cytokine capacity. See Droge et al., 1987, Cell Immunol 108(2):405-16; and Fischer et al., 2007, Blood 109(9):3812-9.

The unique bioenergetics challenge within the tumor microenvironment can range from extreme hypoxic regions to areas of aerobic glycolysis rendering the microenvironment nutrient deficient. See Mockler et al., cited above. Each of these conditions can have a profound effect on T cell function and thus impair anti-tumor immune responses. Hypoxia associated changes in tumor microenvironment can lead to a decrease in T cell proliferation, downregulate mitochondrial oxygen consumption, and impact differentiation leading to a perpetual low level of inflammation. Furthermore, nutrient deprivation can limit the availability of substrates such as glucose that is essential for effector T cell survival and proliferation.

A central part of the T cell activation involves significant alterations in cellular metabolism including a marked increase in glucose metabolism. Although glycolysis represents a rapid source of ATP generation along with NADPH via the pentose shunt, it is not sufficient to generate the full complement of molecules essential for proliferation. However, increased mitochondrial oxygen consumption along with generation of ROS is essential for T cell activation and differentiation. Furthermore, mitochondrial ATP released in the extracellular space enables purinergic signaling mechanisms that regulate T cell activation in the immune—APC synapse. Normal mitochondrial function represents a central role in harnessing of immune response since primary mitochondrial dysfunction is associated with immune dysfunction and increased incidence of infections. See Ledderose et al., 2014, J Biol Chem 289:25936; and Sena et al., 2013, Immunity 38:2 25.

One of the hallmarks of cancer is evasion of the immune system, so cancer immunotherapy must take a different approach by augmenting the beneficial anti-tumor responses of effector T cells initially, leading to memory T cell generation and by attenuating the responses of regulatory T cells. Increasing activated tumor specific effector T cell numbers is perhaps the most beneficial approach to elevate anti-tumor immunity.

MDM2 inhibitors have been described previously as an anti-cancer therapeutic agent (See, e.g., U.S. Pat. No. 9,745,314, the entire contents of which are incorporated herein by reference), and is being evaluated in humans as monotherapy or in combination with standard of care chemotherapy agents for treatment of diseases and conditions wherein inhibition of MDM2 and MDM2-related proteins activity provides a benefit.

The results presented herein demonstrate that MDM2 inhibitors enhanced mouse $CD4^+$ T cell activation (See Example 1.1), while the treatment didn't induce apoptosis of APG-115-treated T cells. In addition, upregulation of inflammatory cytokines (including IFN-γ, IL-2, TNF-α, IL-10 and IL-4) following MDM2 inhibitors treatment in stimulated mouse T cells was observed (See Example 1.2). These cytokines are closely associated with successful immune-mediated cancer eradication. Furthermore, treatment with MDM2 inhibitors upregulated PD-L1 expression in tumor cells (See Example 1.3). The data suggest that MDM2 inhibitors indeed promotes immune response in vitro.

The in vivo efficacy studies (See Examples 2.1) provided in the present application demonstrated that, in a p53 wild-type syngeneic model derived from MH-22A murine hepatoma cells, while anti-PD-1 therapy substantially inhibited tumor growth and led to complete regression (CR) or partial regression (PR) in a large fraction of tumor-bearing animals, the addition of a MDM2 inhibitor was able to expand CR fraction, accelerate the therapeutic effect and, importantly, convert the remaining non-responders into tumors responding to PD-1 blockade. Importantly, such synergistic effect of the combination treatment also applied in a p53 mutant MC38 murine colon syngeneic mouse model (See Example 3.1), indicating the immune modulation function of MDM2-p53 may not require intact p53. The synergistic effect exerted by a MDM2 inhibitor is comparable with or even greater than epacadostat, an IDO1 inhibitor under clinical evaluation. Sequentially, re-challenge studies (See Examples 2.2) confirmed that, like CR mice cured by PD-1 blockade, CR mice previously treated with the combination therapy of anti-PD-1 antibody and a MDM2 inhibitor efficiently rejected re-engrafting of MH-22A tumor cells, implicating for the successful development of immune memory. Importantly, tumor infiltrating lymphocyte (TIL) analysis (See Examples 2.3) revealed significant increases in $CD45^+$ cells, $CD3^+$ T cells, and cytotoxic $CD8^+$ T cells, as well as a decrease in dendritic cells after the combination therapy in comparison with anti-PD-1 monotherapy. The data suggest that the superior effect of the combination is facilitated by the increased number of T cells, especially cytotoxic $CD8^+$ T cells, and reduced dendritic cells in the tumor microenvironment.

Furthermore, pharmacokinetics (PK) analysis (See Examples 2.5) demonstrated that systemic exposure and tumor distribution of a MDM2 inhibitor were appropriately achieved. The increase in systemic exposure and tumor distribution of a MDM2 inhibitor was dose proportionally. Finally, in animal models, the combination therapy was well tolerated by tumor-bearing mice.

Based upon the results presented herein, MDM2 inhibitors and immune checkpoint modulators therapies are expected to work particularly effectively in concert for the treatment of cancers. For example, combination of a MDM2 inhibitor with a modulator of an immune checkpoint molecule has the potential to synergize the activity of these agents in augmenting T cell mediated anti-tumor responses, thereby improving overall durability in patient outcomes. Accordingly, the present invention provides methods for treating cancers in a subject in need thereof by administering to the subject an effective amount of a MDM2 inhibitor and an effective amount of a modulator of an immune check point molecule.

I. Definitions

In accordance with the present disclosure and as used herein, the following terms are defined with the following meanings, unless explicitly stated otherwise.

As used herein, an "immune checkpoint" or "immune checkpoint molecule" is a molecule in the immune system that modulates a signal. An immune checkpoint molecule can be a co-stimulatory checkpoint molecule, i.e., turn up a signal, or an inhibitory checkpoint molecule, i.e., turn down a signal. A "co-stimulatory checkpoint molecule" as used herein is a molecule in the immune system that turns up a signal or is co-stimulatory. An "inhibitory checkpoint molecule", as used herein is a molecule in the immune system that turns down a signal or is co-inhibitory.

As used herein, a "modulator of an immune checkpoint molecule" is an agent capable of altering the activity of an immune checkpoint in a subject. In certain embodiments, a modulator of an immune checkpoint molecule alters the function of one or more immune checkpoint molecules including PD-1, PD-L1, PD-L2, CTLA-4, TIM-3, LAG3, CD160, 2B4, TGF β, VISTA, BTLA, TIGIT, LAIR1, OX40, CD2, CD27, ICAM-1, NKG2C, SLAMF7, NKp80, CD160, B7-H3, LFA-1, 1COS, 4-1BB, GITR, CD30, CD40, BAFFR, HVEM, CD7, LIGHT, and CD83. The modulator of the immune checkpoint may be an activator (e.g., an agonist) or an inhibitor (e.g., an antagonist) of the immune checkpoint. In some embodiments, the modulator of the immune checkpoint molecule is an immune checkpoint binding protein (e.g., an antibody, antibody Fab fragment, divalent antibody, antibody drug conjugate, scFv, fusion protein, bivalent antibody, or tetravalent antibody). In some embodiments, the modulator of the immune checkpoint molecule is a monoclonal antibody or an antigen binding fragment thereof. In other embodiments, the modulator of the immune checkpoint molecule is a small molecule. In a particular embodiment, the modulator of the immune checkpoint molecule is an anti-PD1 antibody. In a particular embodiment, the modulator of the immune checkpoint molecule is an anti-PD-L1 antibody. In a particular embodiment, the modulator of the immune checkpoint molecule is an anti-CTLA-4 antibody.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX.

The term "functional p53," as used herein, refers to wild-type p53 expressed at normal, high, or low levels and mutant or allelic variants of p53 that retain(s) at least about 5% of the activity of wild-type p53, e.g., at least about 10%, about 20%, about 30%, about 40%, about 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "complete regression" refers to tumor is not detectable after treatment.

The term "partial regression" refers to tumor volumes become smaller (e.g., 10%, 20%, 30%, 40%, 50%, 60%, 70%, 80%, 90% less) compared to before treatment.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the terms "treat," "treating" or "treatment" refer, preferably, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) of the state of disease, amelioration or palliation of the disease state, diminishing rate of progression or increasing time to progression, and remission (whether partial or total). "Treatment" of a cancer can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, treatment does not include one or more of a decrease in pain or an increase in the quality of life (QOL) as judged by a qualified individual, e.g., a treating physician, e.g., using accepted assessment tools of pain and QOL.

In certain embodiments, treatment includes a symptom or sign which approaches a normalized value (for example a value obtained in a healthy patient or individual), e.g., is less than 50% different from a normalized value, in certain embodiments less than about 25% different from a normalized value, in other embodiments is less than 10% different from a normalized value, and in yet other embodiments the presence of a symptom is not significantly different from a normalized value as determined using routine statistical tests. As used herein, treatment can include reduction of tumor burden, inhibition of tumor growth, including inducing stable disease in a subject with progressive disease prior to treatment, increasing time to progression, or increasing survival time. Increases can be determined relative to an appropriate control or expected outcomes. As used herein, treatment can include increasing survival of a subject, with or without a decrease in tumor burden, as compared to appropriate controls. Treatment need not be curative.

As used herein, "co-administration" or "combination therapy" is understood as administration of two or more active agents using separate formulations or a single pharmaceutical formulation, or consecutive administration in any order such that, there is a time period while both (or all) active agents simultaneously exert their biological activities. It is contemplated herein that one active agent (e.g., a MDM2 inhibitor) can improve the activity of a second agent, for example, can sensitize target cells, e.g., cancer cells, to the activities of the second agent. Co-administration does not require that the agents are administered at the same time, at the same frequency, or by the same route of administration. As used herein, "co-administration" or "combination therapy" includes administration of a MDM2 inhibitor with one or more modulators of an immune checkpoint molecule. Examples of immune checkpoint modulators are provided herein.

The terms "administer", "administering" or "administration" include any method of delivery of a pharmaceutical composition or agent into a subject's system or to a particular region in or on a subject. In certain embodiments, the agent is delivered orally. In certain embodiments, the agent is administered parenterally. In certain embodiments, the agent is delivered by injection or infusion. In certain embodiments, the agent is delivered topically including transmucosally. In certain embodiments, the agent is delivered by inhalation. In certain embodiments of the invention, an agent is administered by parenteral delivery, including, intravenous, intramuscular, subcutaneous, intramedullary injections, as well as intrathecal, direct intraventricular, intraperitoneal, intranasal, or intraocular injections. In one embodiment, the compositions provided herein may be administered by injecting directly to a tumor. In some embodiments, the formulations of the invention may be administered by intravenous injection or intravenous infusion. In certain embodiments, the formulation of the invention can be administered by continuous infusion. In certain embodiments, administration is not oral. In certain embodiments, administration is systemic. In certain embodiments, administration is local. In some embodiments, one or more routes of administration may be combined, such as, for example, intravenous and intratumoral, or intravenous and peroral, or intravenous and oral, intravenous and topical, or intravenous and transdermal or transmucosal. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, continuous infusion, etc.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, a "dispersion" refers to a system in which particles of colloidal size of any nature (e.g., solid, liquid or gas) are dispersed in a continuous phase of a different composition or state. In intravenous drug delivery the continuous phase is substantially water and the dispersed particles can be solid (a suspension) or an immiscible liquid (emulsion).

A "subject" to be treated by the method of the invention can mean either a human or non-human animal, preferably a mammal, more preferably a human. In certain embodiments, a subject has a detectable tumor prior to initiation of treatments using the methods of the invention. In certain embodiments, the subject has a detectable tumor at the time of initiation of the treatments using the methods of the invention.

As used herein, the term "safe and therapeutic effective amount" or "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure.

The term "therapeutically effective amount" or "effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" or "effective amount" will vary depending on the compound, the disease and its severity and the age, weight, etc., of the patient to be treated. A therapeutically effective amount or an effective amount need not be curative. A therapeutically effective amount or an effective amount need not prevent a disease or condition from ever occurring. Instead a therapeutically effective amount or an effective amount is an amount that will at least delay or reduce the onset, severity, or progression of a disease or condition. Disease progression can be monitored, for example, by one or more of tumor burden, time to progression, survival time, or other clinical measurements used in the art.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like.

"Preventing" or "prevention" refers to a reduction in risk of acquiring a disease or disorder. Prevention does not require that the disease or condition never occur, or recur, in the subject.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Ranges expressed as "up to" a certain value, e.g., up to 5, is understood as all values, including the upper limit of the range, e.g., 0, 1, 2, 3, 4, and 5, and fractional values as appropriate. Up to or within a week is understood to include, 0.5, 1, 2, 3, 4, 5, 6, or 7 days. Similarly, ranges delimited by "at least" are understood to include the lower value provided and all higher numbers.

All percent formulations are w/w unless otherwise indicated.

As used herein, "about" is understood to include within three standard deviations of the mean or within standard ranges of tolerance in the specific art. In certain embodiments, about is understood a variation of no more than 0.5.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used inclusively herein to mean, and is used interchangeably with, the term "and/or," unless context clearly indicates otherwise.

The term "such as" is used herein to mean, and is used interchangeably, with the phrase "such as but not limited to".

II. MDM2 Inhibitors

The MDM2 inhibitors disclosed in the present invention inhibit the interaction between p53 or p53-related proteins and MDM2 or MDM2-related proteins. By inhibiting the negative effect of MDM2 or MDM2-related proteins on p53 or p53-related proteins, the MDM2 inhibitors of the present invention sensitize cells to inducers of apoptosis and/or cell cycle arrest. In one embodiment, the MDM2 inhibitors of the present invention induce apoptosis and/or cell cycle arrest.

Compound disclosed herein can be effective as MDM2 inhibitors. In some embodiments, a compound of the invention is represented by formula (I):

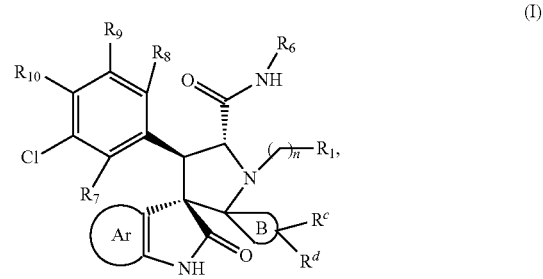

or a pharmaceutically acceptable salt thereof, wherein

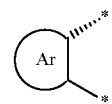

is selected from the group consisting of

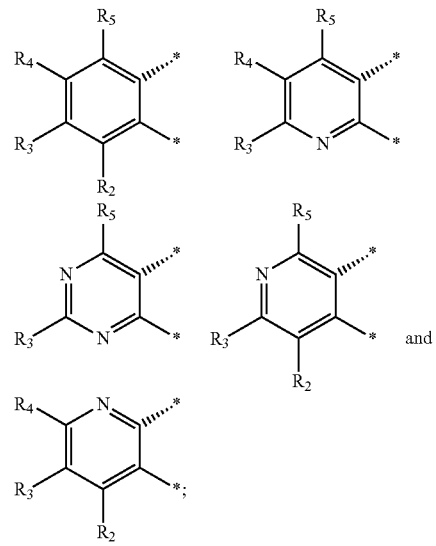

B is a $C_{4-7}$ carbocyclic ring;
$R_1$ is H, substituted or unsubstituted $C_1$-4 alkyl, substituted or unsubstituted cycloalkyl, substituted or unsubstituted heterocycloalkyl, $OR^a$, or $NR^aR^b$;
n is 0, 1, or 2;
$R_2$, $R_3$, $R_4$, $R_5$, $R_7$, $R_8$, $R_9$, and $R_{10}$, independently, are selected from the group consisting of H, F, Cl, $CH_3$, and $CF_3$;
$R_6$ is

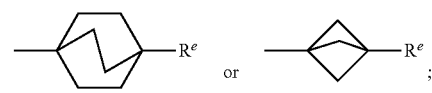

R$^a$ is hydrogen or substituted or unsubstituted C$_{1-4}$ alkyl;
R$^b$ is hydrogen or substituted or unsubstituted C$_1$-4 alkyl;
R$^c$ and R$^d$ are substituents on one carbon atom of ring B, wherein
R$^c$ is H, C$_{1-3}$ alkyl, C$_{1-3}$ alkylene-OR$^a$, OR$^a$, or halo;
R$^d$ is H, C$_{1-3}$ alkyl, C$_{1-3}$ alkylene-OR$^a$, OR$^a$, or halo; or
R$^c$ and R$^d$ are taken together with the carbon to which they are attached to form a 4 to 6-membered Spiro substituent, optionally containing an oxygen atom; and
R$^e$ is —C(=O)OR$^a$, —C(=O)NR$^a$R$^b$, or —C(=O)NHSO$_2$CH$_3$.

The compounds of structural formula (I) inhibit MDM2-p53 interactions and are useful in the treatment of a variety of diseases and conditions. In particular, the compounds of structural formula (I) are used in methods of treating a disease or condition wherein inhibition of MDM2 and MDM2-related protein provides a benefit, for example, cancers and proliferative diseases. The method comprises administering a therapeutically effective amount of a compound of structural formula (I) to a subject in need thereof.

As used herein, the term "alkyl" refers to straight chained and branched saturated C$_{1-10}$ hydrocarbon groups, including but not limited to methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term C$_{m-n}$ means the alkyl group has "m" to "n" carbon atoms. The term "alkylene" refers to an alkyl group having a substituent. An alkyl, e.g., methyl, or alkylene, e.g., —CH$_2$—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" is defined as fluoro, chloro, bromo, or iodo.

The term "hydroxy" is defined as —OH.

The term "alkoxy" is defined as —OR, wherein R is alkyl.

The term "amino" is defined as —NH$_2$, and the term "alkylamino" is defined as —NR$_2$, wherein at least one R is alkyl and the second R is alkyl or hydrogen.

The term "carbamoyl" is defined as —C(=O)NR$_2$.

The term "carboxy" is defined as —C(=O)OH or a salt thereof.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$ alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$ alkyl, —OCOalkyl, aryl, and heteroaryl.

As used herein, the term "cycloalkyl" means a monocyclic or bicyclic, saturated or partially unsaturated, ring system containing three to eight carbon atoms, including cyclopropyl, cyclobutyl, cyclopentyl, cyclohexyl, cycloheptyl, and cyclooctyl, optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Non-limiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, C$_{1-6}$ alkyl, C$_{1-6}$ alkoxy, cyano, amino, carbamoyl, nitro, carboxy, C$_{2-7}$ alkenyl, C$_{2-7}$ alkynyl, or the like on an atom of the ring.

In some embodiments,

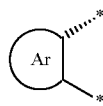

is

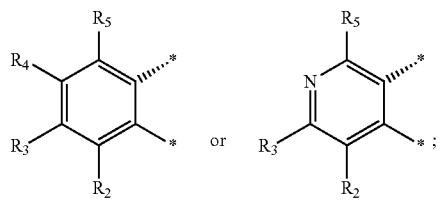

In some embodiments, B is

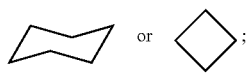

In some embodiments, n is 0 or 1 and $R_1$ is H or $CH_3$.

In some embodiments,

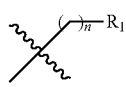

is H, $CH_3$, or $CH_2CH_3$.

In some embodiments, $R_2$ is H. In other embodiments, $R_3$ is halo, and preferably chloro. In still another embodiments, $R_4$ is H, $R_5$ is H, or both $R_4$ and $R_5$ are H.

In some embodiments, $R_7$ is halo, and more preferably is fluoro.

In some embodiments, each of $R^8$, $R^9$, and $R^{10}$ are H.

In some embodiments, $R^a$ and $R^b$, individually, are H, $CH_3$, or $CH_2CH_3$.

In some embodiments, $R^c$ and $R^d$, individually, are H, halo, OH, $CH_3$, $CH_2CH_3$, or $CH_2OH$. In some embodiments, $R^c$ and $R^d$ are F and F, H and H, OH and $CH_3$, OH and H, $CH_3$ and $CH_3$, $CH_3$ and OH, H and OH, $CH_2CH_3$ and $CH_2CH_3$, and $CH_2OH$ and $CH_2OH$.

In some embodiments, $R^e$ is —C(=O)OH, —C(=O)NH_2$, or —C(=O)NHSO_2CH_3$.

In one embodiment, the MDM2 inhibitor is selected from:

Compound Q

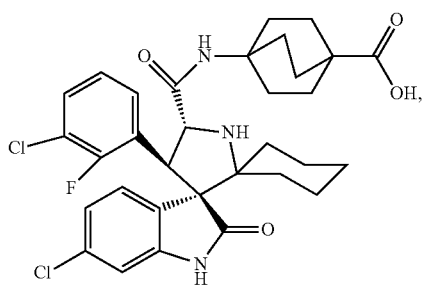

Compound M

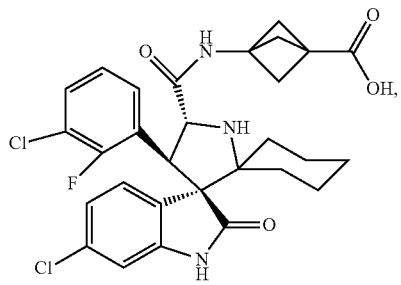

Compound N

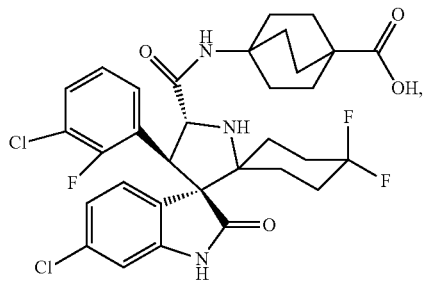

Compound H

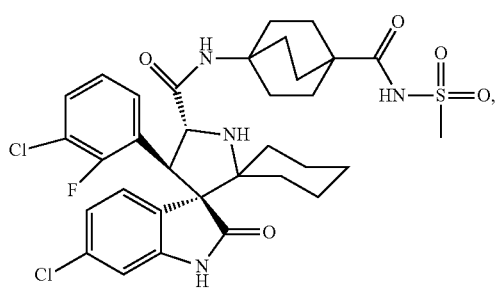

Compound J

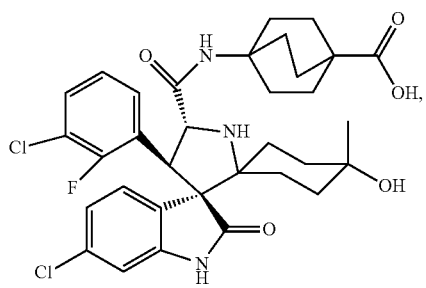

Compound G

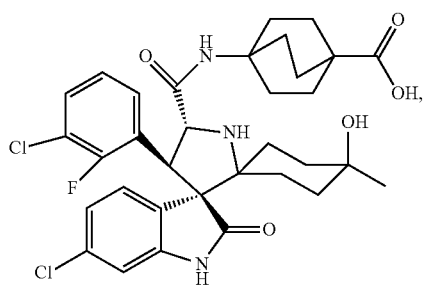

-continued
Compound E
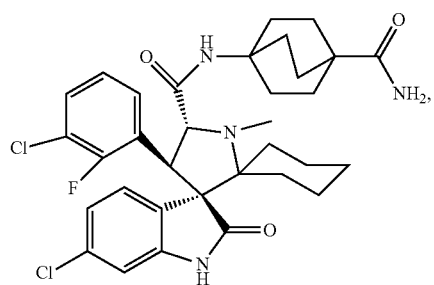
Compound C
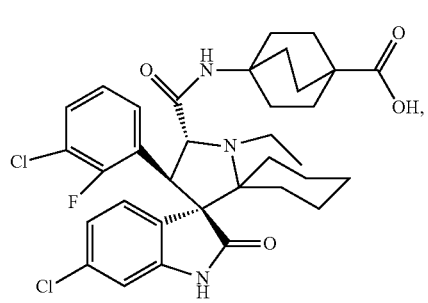
Compound F
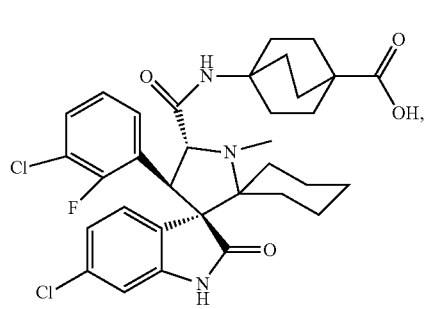
Compound Y
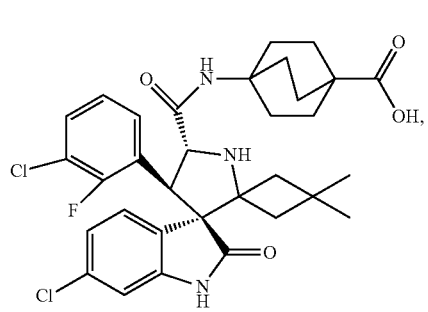
Compound K
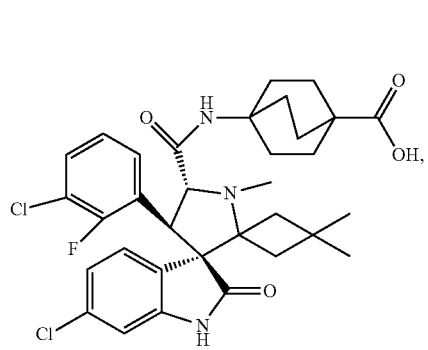
-continued
Compound P
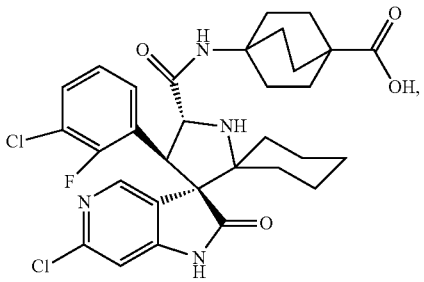
Compound T
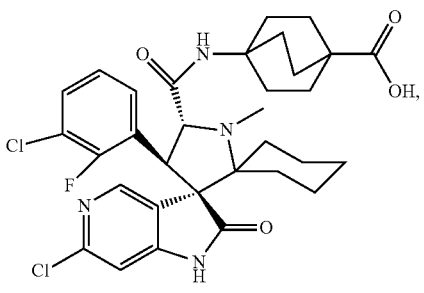
Compound S
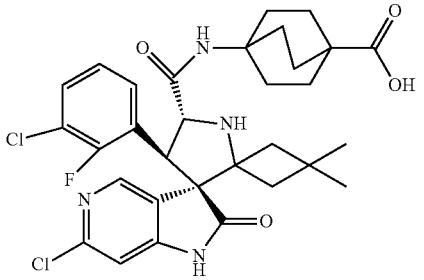
and
Compound W
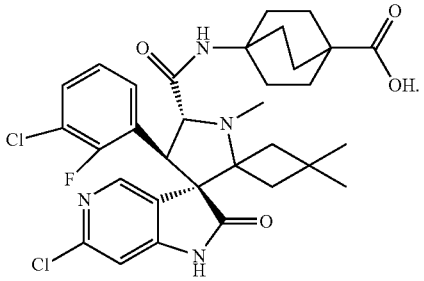
In one embodiment, the MDM2 inhibitor is
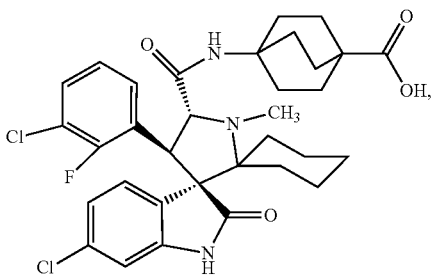 [SMILES: CN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]
or a pharmaceutically acceptable salt thereof.

In one embodiment, the MDM2 inhibitor is

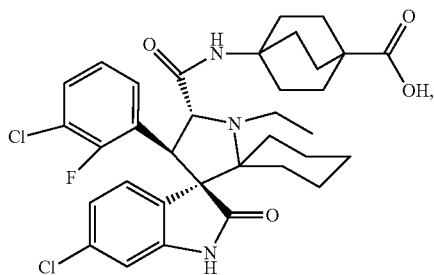 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt thereof. This compound is also referred to herein as APG-115.

More MDM2 inhibitors and the synthesis of the MDM2 inhibitors that can be used in the present application are further disclosed in U.S. Pat. No. 9,745,314, which is incorporated herein by reference.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation, such as, but not limited to, alkali and alkaline earth metal ions, e.g., $Na^+$, $K^+$, $Ca^{2+}$, and $Mg^{2+}$ well as organic cations such as, but not limited to, ammonium and substituted ammonium ions, e.g., $NH_4^+$, $NHMe_3^+$, $NH_2Me_2^+$, $NHMe_3^+$ and $NMe_4^+$. Examples of monovalent and divalent pharmaceutically acceptable cations are discussed, e.g., in Berge et al. *J. Pharm. Sci.*, 66:1-19 (1997).

The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts thereof.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures)) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

III. Immunotherapies

The ability of tumor cells to harness a range of complex, overlapping mechanisms to prevent the immune system from distinguishing self from non-self represents the fundamental mechanism of tumors to evade immunosurveillance. Mechanism(s) include disruption of antigen presentation, disruption of regulatory pathways controlling T cell activation or inhibition (immune checkpoint regulation), recruitment of cells that contribute to immune suppression (Tregs, MDSC) or release of factors that influence immune activity (IDO, PGE2). See Harris et al., 2013, *J Immunotherapy Cancer* 1:12; Chen et al., 2013, *Immunity* 39:1; Pardoll, et al., 2012, *Nature Reviews: Cancer* 12:252; and Sharma et al., 2015, *Cell* 161:205, each of which is incorporated by reference herein in its entirety. Recent years have seen an explosion of immune-oncology therapeutic modalities with approaches ranging from inhibitors of T cell checkpoint, T cell activating agents, and potential vaccines either approved for clinical use or under active investigation. A few of these, including anti-CTLA-4, anti-PD-1, and anti-PD-L1 immune checkpoint therapies, have demonstrated variable success and have been approved for clinical use. Although the checkpoint inhibitors are the most advanced in clinical development for treatment of various cancers, these represent a fraction of the potential targets and pathways that can be harnessed to improve anti-tumor responses. This is evidenced by the continuous emergence of new lists of potential molecules influencing checkpoint or inhibitory pathways along with co-stimulatory molecules that improve immune responses that are in various stages of preclinical and clinical development. Examples of new immune checkpoints that are being evaluated for cancer treatment include LAG-3 (Triebel et al., 1990, *J. Exp. Med.* 171: 1393-1405), TIM-3 (Sakuishi et al., 2010, *J. Exp. Med* 207: 2187-2194) and VISTA (Wang et al., 2011, *J. Exp. Med.* 208: 577-592). Examples of co-stimulatory molecules that improve immune responses include ICOS (Fan et al., 2014, *J. Exp. Med.* 211: 715-725), OX40 (Curti et al., 2013, *Cancer Res.* 73: 7189-7198) and 4-1BB (Melero et al., 1997, *Nat. Med.* 3: 682-685).

In some embodiments, the immune checkpoint molecule of the invention is a co-stimulatory immune checkpoint (i.e., a molecule that stimulates the immune response), and the immune checkpoint modulator is an activator (an agonist) of a stimulatory immune checkpoint. In some embodiments, the immune checkpoint molecule of the invention is an inhibitory immune checkpoint molecule, (i.e. a molecule that inhibits immune response), and the immune checkpoint modulator is an inhibitor (an antagonist) of an inhibitory immune checkpoint. In some embodiments, the immune checkpoint modulator is an immune checkpoint binding protein (e.g., an antibody, antibody Fab fragment, divalent antibody, antibody drug conjugate, scFv, fusion protein, bivalent antibody, or tetravalent antibody). In certain embodiments, the immune checkpoint modulator is capable of binding to, or modulating the activity of more than one immune checkpoint. Examples of stimulatory and inhibitory immune checkpoints, and molecules that modulate these immune checkpoints that may be used in the methods of the invention, are provided below.

i. Co-Stimulatory Immune Checkpoint Molecules

CD27 supports antigen-specific expansion of naïve T cells and is vital for the generation of T cell memory (See, e.g., Hendriks et al. (2000) *Nat. Immunol.* 171 (5): 433-40). CD27 is also a memory marker of B cells (See, e.g., Agematsu et al. (2000) *Histol. Histopathol.* 15 (2): 573-6. CD27 activity is governed by the transient availability of its ligand, CD70, on lymphocytes and dendritic cells (See, e.g., Borst et al. (2005) *Curr. Opin. Immunol.* 17 (3): 275-81). Multiple immune checkpoint modulators specific for CD27 have been developed and may be used as disclosed herein. In some embodiments, the immune checkpoint modulator is an agent that modulates the activity and/or expression of CD27. In some embodiments, the immune checkpoint modulator is an agent that binds to CD27 (e.g., an anti-CD27 antibody). In some embodiments, the checkpoint modulator is a CD27 agonist. In some embodiments, the checkpoint modulator is a CD27 antagonist. In some embodiments, the immune checkpoint modulator is an CD27-binding protein (e.g., an antibody). In some embodiments, the immune checkpoint modulator is varlilumab (Celldex Therapeutics). Additional CD27-binding proteins (e.g., antibodies) are known in the art and are disclosed, e.g., in U.S. Pat. Nos. 9,248,183, 9,102,737, 9,169,325, 9,023,999, 8,481,029; U.S. Patent Application Publication Nos. 2016/0185870, 2015/0337047, 2015/0299330, 2014/0112942, 2013/0336976, 2013/0243795, 2013/0183316, 2012/0213771, 2012/0093805, 2011/0274685, 2010/0173324; and PCT Publication Nos. WO 2015/016718, WO 2014/140374, WO 2013/138586, WO 2012/004367, WO 2011/130434, WO 2010/001908, and WO 2008/051424, each of which is incorporated by reference herein.

CD28. Cluster of Differentiation 28 (CD28) is one of the proteins expressed on T cells that provide co-stimulatory signals required for T cell activation and survival. T cell stimulation through CD28 in addition to the T-cell receptor (TCR) can provide a potent signal for the production of various interleukins (IL-6 in particular). Binding with its two ligands, CD80 and CD86, expressed on dendritic cells, prompts T cell expansion (See, e.g., Prasad et al. (1994) *Proc. Nat'l. Acad. Sci. USA* 91(7): 2834-8). Multiple immune checkpoint modulators specific for CD28 have been developed and may be used as disclosed herein. In some embodiments, the immune checkpoint modulator is an agent that modulates the activity and/or expression of CD28. In some embodiments, the immune checkpoint modulator is an agent that binds to CD28 (e.g., an anti-CD28 antibody). In some embodiments, the checkpoint modulator is an CD28 agonist. In some embodiments, the checkpoint modulator is an CD28 antagonist. In some embodiments, the immune checkpoint modulator is an CD28-binding protein (e.g., an antibody). In some embodiments, the immune checkpoint modulator is selected from the group consisting of TAB08 (TheraMab LLC), lulizumab (also known as BMS-931699, Bristol-Myers Squibb), and FR104 (OSE Immunotherapeutics). Additional CD28-binding proteins (e.g., antibodies) are known in the art and are disclosed, e.g., in U.S. Pat. Nos. 9,119,840, 8,709,414, 9,085,629, 8,034,585, 7,939,638, 8,389,016, 7,585,960, 8,454,959, 8,168,759, 8,785,604, 7,723,482; U.S. Patent Application Publication Nos. 2016/0017039, 2015/0299321, 2015/0150968, 2015/0071916, 2015/0376278, 2013/0078257, 2013/0230540, 2013/0078236, 2013/0109846, 2013/0266577, 2012/0201814, 2012/0082683, 2012/0219553, 2011/0189735, 2011/0097339, 2010/0266605, 2010/0168400, 2009/0246204, 2008/0038273; and PCT Publication Nos. WO 2015198147, WO 2016/05421, WO 2014/1209168, WO 2011/101791, WO 2010/007376, WO 2010/009391, WO 2004/004768, WO 2002/030459, WO 2002/051871, and WO 2002/047721, each of which is incorporated by reference herein.

CD40. Cluster of Differentiation 40 (CD40, also known as TNFRSF5) is found on a variety of immune system cells including antigen presenting cells. CD40L, otherwise known as CD154, is the ligand of CD40 and is transiently expressed on the surface of activated CD4$^+$ T cells. CD40 signaling is known to 'license' dendritic cells to mature and thereby trigger T-cell activation and differentiation (See, e.g., O'Sullivan et al. (2003) Crit. Rev. Immunol. 23 (1): 83-107. Multiple immune checkpoint modulators specific for CD40 have been developed and may be used as disclosed herein. In some embodiments, the immune checkpoint modulator is an agent that modulates the activity and/or expression of CD40. In some embodiments, the immune checkpoint modulator is an agent that binds to CD40 (e.g., an anti-CD40 antibody). In some embodiments, the checkpoint modulator is a CD40 agonist. In some embodiments, the checkpoint modulator is an CD40 antagonist. In some embodiments, the immune checkpoint modulator is a CD40-binding protein selected from the group consisting of dacetuzumab (Genentech/Seattle Genetics), CP-870,893 (Pfizer), bleselumab (Astellas Pharma), lucatumumab (Novartis), CFZ533 (Novartis; See, e.g., Cordoba et al. (2015) Am. J. Transplant. 15(11): 2825-36), RG7876 (Genentech Inc.), FFP104 (PanGenetics, B.V.), APX005 (Apexigen), BI 655064 (Boehringer Ingelheim), Chi Lob 7/4 (Cancer Research UK; See, e.g., Johnson et al. (2015) Clin. Cancer Res. 21(6): 1321-8), ADC-1013 (BioInvent International), SEA-CD40 (Seattle Genetics), XmAb 5485 (Xencor), PG120 (PanGenetics B.V.), teneliximab (Bristol-Myers Squibb; See, e.g., Thompson et al. (2011) Am. J. Transplant. 11(5): 947-57), and AKH3 (Biogen; See, e.g., International Publication No. WO 2016/028810). Additional CD40-binding proteins (e.g., antibodies) are known in the art and are disclosed, e.g., in U.S. Pat. Nos. 9,234,044, 9,266,956, 9,109,011, 9,090,696, 9,023,360, 9,023,361, 9,221,913, 8,945,564, 8,926,979, 8,828,396, 8,637,032, 8,277,810, 8,088,383, 7,820,170, 7,790,166, 7,445,780, 7,361,345, 8,961,991, 8,669,352, 8,957,193, 8,778,345, 8,591,900, 8,551,485, 8,492,531, 8,362,210, 8,388,971; U.S. Patent Application Publication Nos. 2016/0045597, 2016/0152713, 2016/0075792, 2015/0299329, 2015/0057437 2015/0315282, 2015/0307616, 2014/0099317, 2014/0179907, 2014/0349395, 2014/0234344, 2014/0348836, 2014/0193405, 2014/0120103, 2014/0105907, 2014/0248266, 2014/0093497, 2014/0010812, 2013/0024956, 2013/0023047, 2013/0315900, 2012/0087927, 2012/0263732, 2012/0301488, 2011/0027276, 2011/0104182, 2010/0234578, 2009/0304687, 2009/0181015, 2009/0130715, 2009/0311254, 2008/0199471, 2008/0085531, 2016/0152721, 2015/0110783, 2015/0086991, 2015/0086559, 2014/0341898, 2014/0205602, 2014/0004131, 2013/0011405, 2012/0121585, 2011/0033456, 2011/0002934, 2010/0172912, 2009/0081242, 2009/0130095, 2008/0254026, 2008/0075727, 2009/0304706, 2009/0202531, 2009/0117111, 2009/0041773, 2008/0274118, 2008/0057070, 2007/0098717, 2007/0218060, 2007/0098718, 2007/0110754; and PCT Publication Nos. WO 2016/069919, WO 2016/023960, WO 2016/023875, WO 2016/028810, WO 2015/134988, WO 2015/091853, WO 2015/091655, WO 2014/065403, WO 2014/070934, WO 2014/065402, WO 2014/207064, WO 2013/034904, WO 2012/125569, WO 2012/149356, WO 2012/111762, WO 2012/145673, WO 2011/123489, WO 2010/123012, WO 2010/104761, WO 2009/094391, WO 2008/091954, WO 2007/129895, WO 2006/128103, WO 2005/063289, WO 2005/063981, WO 2003/040170, WO 2002/011763, WO 2000/075348, WO 2013/164789, WO 2012/075111, WO 2012/065950, WO 2009/062054, WO 2007/124299, WO 2007/053661, WO 2007/053767, WO 2005/044294, WO 2005/044304, WO 2005/044306, WO 2005/044855, WO 2005/044854, WO 2005/044305, WO 2003/045978, WO 2003/029296, WO 2002/028481, WO 2002/028480, WO 2002/028904, WO 2002/028905, WO 2002/088186, and WO 2001/024823, each of which is incorporated by reference herein.

CD122. CD122 is the Interleukin-2 receptor beta sub-unit and is known to increase proliferation of CD8$^+$ effector T cells. See, e.g., Boyman et al. (2012) Nat. Rev. Immunol. 12 (3): 180-190. Multiple immune checkpoint modulators specific for CD122 have been developed and may be used as disclosed herein. In some embodiments, the immune checkpoint modulator is an agent that modulates the activity and/or expression of CD122. In some embodiments, the immune checkpoint modulator is an agent that binds to CD122 (e.g., an anti-CD122 antibody). In some embodiments, the checkpoint modulator is an CD122 agonist. In some embodiments, the checkpoint modulator is an CD122 antagonist. In some embodiments, the immune checkpoint modulator is humanized MiK-Beta-1 (Roche; See, e.g., Morris et al. (2006) Proc Nat'l. Acad. Sci. USA 103(2): 401-6, which is incorporated by reference). Additional CD122-binding proteins (e.g., antibodies) are known in the art and are disclosed, e.g., in U.S. Pat. No. 9,028,830, which is incorporated by reference herein.

OX40. The OX40 receptor (also known as CD134) promotes the expansion of effector and memory T cells. OX40 also suppresses the differentiation and activity of T-regulatory cells, and regulates cytokine production (See, e.g., Croft et al. (2009) Immunol. Rev. 229(1): 173-91). Multiple immune checkpoint modulators specific for OX40 have been developed and may be used as disclosed herein. In some embodiments, the immune checkpoint modulator is an agent that modulates the activity and/or expression of OX40. In some embodiments, the immune checkpoint modulator is an agent that binds to OX40 (e.g., an anti-OX40 antibody). In some embodiments, the checkpoint modulator is an OX40 agonist. In some embodiments, the checkpoint modulator is an OX40 antagonist. In some embodiments, the immune checkpoint modulator is a OX40-binding protein (e.g., an antibody) selected from the group consisting of MEDI6469 (AgonOx/Medimmune), pogalizumab (also known as MOXR0916 and RG7888; Genentech, Inc.), tavolixizumab (also known as MEDI0562; Medimmune), and GSK3174998 (GlaxoSmithKline). Additional OX-40-binding proteins (e.g., antibodies) are known in the art and are disclosed, e.g., in U.S. Pat. Nos. 9,163,085, 9,040,048, 9,006,396, 8,748,585, 8,614,295, 8,551,477, 8,283,450, 7,550,140; U.S. Patent Application Publication Nos. 2016/0068604, 2016/0031974, 2015/0315281, 2015/0132288, 2014/0308276, 2014/0377284, 2014/0044703, 2014/0294824, 2013/0330344, 2013/0280275, 2013/0243772, 2013/0183315, 2012/0269825, 2012/0244076, 2011/0008368, 2011/0123552, 2010/0254978, 2010/0196359, 2006/0281072; and PCT Publication Nos. WO 2014/148895, WO 2013/068563, WO 2013/038191, WO 2013/028231, WO 2010/096418, WO 2007/062245, and WO 2003/106498, each of which is incorporated by reference herein.

GITR. Glucocorticoid-induced TNFR family related gene (GITR) is a member of the tumor necrosis factor receptor (TNFR) superfamily that is constitutively or conditionally expressed on Treg, CD4, and CD8 T cells. GITR is rapidly upregulated on effector T cells following TCR ligation and activation. The human GITR ligand (GITRL) is constitutively expressed on APCs in secondary lymphoid organs and some nonlymphoid tissues. The downstream effect of GITR: GITRL interaction induces attenuation of Treg activity and enhances CD4$^+$ T cell activity, resulting in a reversal of Treg-mediated immunosuppression and increased immune stimulation. Multiple immune checkpoint modulators specific for GITR have been developed and may be used as disclosed herein. In some embodiments, the immune checkpoint modulator is an agent that modulates the activity and/or expression of GITR. In some embodiments, the immune checkpoint modulator is an agent that binds to GITR (e.g., an anti-GITR antibody). In some embodiments, the checkpoint modulator is an GITR agonist. In some embodiments, the checkpoint modulator is an GITR antagonist. In some embodiments, the immune checkpoint modulator is a GITR-binding protein (e.g., an antibody) selected from the group consisting of TRX518 (Leap Therapeutics), MK-4166 (Merck & Co.), MEDI-1873 (MedImmune), INCAGN1876 (Agenus/Incyte), and FPA154 (Five Prime Therapeutics). Additional GITR-binding proteins (e.g., antibodies) are known in the art and are disclosed, e.g., in U.S. Pat. Nos. 9,309,321, 9,255,152, 9,255,151, 9,228,016, 9,028,823, 8,709,424, 8,388,967; U.S. Patent Application Publication Nos. 2016/0145342, 2015/0353637, 2015/0064204, 2014/0348841, 2014/0065152, 2014/0072566, 2014/0072565, 2013/0183321, 2013/0108641, 2012/0189639; and PCT Publication Nos. WO 2016/054638, WO 2016/057841, WO 2016/057846, WO 2015/187835, WO 2015/184099, WO 2015/031667, WO 2011/028683, and WO 2004/107618, each of which is incorporated by reference herein.

ICOS. Inducible T-cell costimulator (ICOS, also known as CD278) is expressed on activated T cells. Its ligand is ICOSL, which is expressed mainly on B cells and dendritic cells. ICOS is important in T cell effector function. ICOS expression is up-regulated upon T cell activation (See, e.g., Fan et al. (2014) *J. Exp. Med.* 211(4): 715-25). Multiple immune checkpoint modulators specific for ICOS have been developed and may be used as disclosed herein. In some embodiments, the immune checkpoint modulator is an agent that modulates the activity and/or expression of ICOS. In some embodiments, the immune checkpoint modulator is an agent that binds to ICOS (e.g., an anti-ICOS antibody). In some embodiments, the checkpoint modulator is an ICOS agonist. In some embodiments, the checkpoint modulator is an ICOS antagonist. In some embodiments, the immune checkpoint modulator is a ICOS-binding protein (e.g., an antibody) selected from the group consisting of MEDI-570 (also known as JMab-136, Medimmune), GSK3359609 (GlaxoSmithKline/INSERM), and JTX-2011 (Jounce Therapeutics). Additional ICOS-binding proteins (e.g., antibodies) are known in the art and are disclosed, e.g., in U.S. Pat. Nos. 9,376,493, 7,998,478, 7,465,445, 7,465,444; U.S. Patent Application Publication Nos. 2015/0239978, 2012/0039874, 2008/0199466, 2008/0279851; and PCT Publication No. WO 2001/087981, each of which is incorporated by reference herein.

4-1BB. 4-1BB (also known as CD137) is a member of the tumor necrosis factor (TNF) receptor superfamily. 4-1BB (CD137) is a type II transmembrane glycoprotein that is inducibly expressed on primed CD4$^+$ and CD8$^+$ T cells, activated NK cells, DCs, and neutrophils, and acts as a T cell costimulatory molecule when bound to the 4-1BB ligand (4-1BBL) found on activated macrophages, B cells, and DCs. Ligation of the 4-1BB receptor leads to activation of the NF-κB, c-Jun and p38 signaling pathways and has been shown to promote survival of CD8$^+$ T cells, specifically, by upregulating expression of the antiapoptotic genes BcL-x(L) and Bfl-1. In this manner, 4-1BB serves to boost or even salvage a suboptimal immune response. Multiple immune checkpoint modulators specific for 4-1BB have been developed and may be used as disclosed herein. In some embodiments, the immune checkpoint modulator is an agent that modulates the activity and/or expression of 4-1BB. In some embodiments, the immune checkpoint modulator is an agent that binds to 4-1BB (e.g., an anti-4-1BB antibody). In some embodiments, the checkpoint modulator is an 4-1BB agonist. In some embodiments, the checkpoint modulator is an 4-1BB antagonist. In some embodiments, the immune checkpoint modulator is a 4-1BB-binding protein is urelumab (also known as BMS-663513; Bristol-Myers Squibb) or utomilumab (Pfizer). In some embodiments, the immune checkpoint modulator is a 4-1BB-binding protein (e.g., an antibody). 4-1BB-binding proteins (e.g., antibodies) are known in the art and are disclosed, e.g., in U.S. Pat. Nos. 9,382,328, 8,716,452, 8,475,790, 8,137,667, 7,829,088, 7,659,384; U.S. Patent Application Publication Nos. 2016/0083474, 2016/0152722, 2014/0193422, 2014/0178368, 2013/0149301, 2012/0237498, 2012/0141494, 2012/0076722, 2011/0177104, 2011/0189189, 2010/0183621, 2009/0068192, 2009/0041763, 2008/0305113, 2008/0008716; and PCT Publication Nos. WO 2016/029073, WO 2015/188047, WO 2015/179236, WO 2015/119923, WO 2012/032433, WO 2012/145183, WO 2011/031063, WO 2010/132389, WO 2010/042433, WO 2006/126835, WO 2005/035584, WO 2004/010947; and Martinez-Forero et al. (2013) *J. Immunol.* 190(12): 6694-706, and Dubrot et al. (2010) *Cancer Immunol. Immunother.* 59(8): 1223-33, each of which is incorporated by reference herein.

CD2. CD2 (cluster of differentiation 2) is a cell adhesion molecule found on the surface of T cells and natural killer (NK) cells. It has also been called T-cell surface antigen Ti i/Leu-5, LFA-2, LFA-3 receptor, erythrocyte receptor and rosette receptor. It interacts with other adhesion molecules, such as lymphocyte function-associated antigen-3 (LFA-3/CD58) in humans, or CD48 in rodents, which are expressed on the surfaces of other cells. In addition to its adhesive properties, CD2 also acts as a co-stimulatory molecule on T and NK cells. CD2 is a specific marker for T cells and NK cells, and can therefore be used in immunohistochemistry to identify the presence of such cells in tissue sections. The great majority of T cell lymphomas and leukaemias also express CD2, making it possible to use the presence of the antigen to distinguish these conditions from B cell neoplasms. In some embodiments, the immune checkpoint modulator is an agent that modulates the activity and/or expression of CD2. In some embodiments, the immune checkpoint modulator is an agent that binds to CD2 (e.g., an anti-CD2 antibody). In some embodiments, the checkpoint modulator is an CD2 agonist. In some embodiments, the checkpoint modulator is an CD2 antagonist.

ICAM-1. ICAM-1 (Intercellular Adhesion Molecule 1) also known as CD54 (Cluster of Differentiation 54) is a protein that in humans is encoded by the ICAM1 gene. This gene encodes a cell surface glycoprotein which is typically expressed on endothelial cells and cells of the immune system. It binds to integrins of type CD11a/CD18, or CD11b/CD18 and is also exploited by rhinovirus as a receptor. ICAM-1 is an endothelial- and leukocyte-associated transmembrane protein long known for its importance in stabilizing cell-cell interactions and facilitating leukocyte endothelial transmigration. More recently, ICAM-1 has been characterized as a site for the cellular entry of human rhinovirus. ICAM-1 ligation produces proinflammatory effects such as inflammatory leukocyte recruitment by signaling through cascades involving a number of kinases, including the kinase p56lyn. ICAM-1 has been implicated in subarachnoid hemorrhage (SAH). Levels of ICAM-1 are shown to be significantly elevated in patients with SAH over control subjects in many studies. While ICAM-1 has not been shown to be directly correlated with cerebral vasospasm, a secondary symptom that affects 70% of SAH patients, treatment with anti-ICAM-1 reduced the severity of vasospasm. In some embodiments, the immune checkpoint modulator is an agent that modulates the activity and/or expression of ICAM-1. In some embodiments, the immune checkpoint modulator is an agent that binds to ICAM-1 (e.g., an anti-ICAM-1 antibody). In some embodiments, the checkpoint modulator is an ICAM-1 agonist. In some embodiments, the checkpoint modulator is an ICAM-1 antagonist.

NKG2C. NKG2-C type II integral membrane protein is a protein that in humans is encoded by the KLRC2 gene. Natural killer (NK) cells are lymphocytes that can mediate lysis of certain tumor cells and virus-infected cells without previous activation. They can also regulate specific humoral and cell-mediated immunity. NK cells preferentially express several calcium-dependent (C-type) lectins, which have been implicated in the regulation of NK cell function. The group, designated KLRC (NKG2) are expressed primarily in natural killer (NK) cells and encodes a family of transmembrane proteins characterized by a type II membrane orientation (extracellular C terminus) and the presence of a C-type lectin domain. The KLRC (NKG2) gene family is located within the NK complex, a region that contains several C-type lectin genes preferentially expressed on NK cells. KLRC2 alternative splice variants have been described but their full-length nature has not been determined. In some embodiments, the immune checkpoint modulator is an agent that modulates the activity and/or expression of NKG2C. In some embodiments, the immune checkpoint modulator is an agent that binds to NKG2C (e.g., an anti-NKG2C antibody). In some embodiments, the checkpoint modulator is an NKG2C agonist. In some embodiments, the checkpoint modulator is an NKG2C antagonist.

SLAMF7. SLAM family member 7 is a protein that in humans is encoded by the SLAMF7 gene. The surface antigen CD319 (SLAMF7) is a robust marker of normal plasma cells and malignant plasma cells in multiple myeloma. In contrast to CD138 (the traditional plasma cell marker), CD319/SLAMF7 is much more stable and allows robust isolation of malignant plasma cells from delayed or even cryopreserved samples. In some embodiments, the immune checkpoint modulator is an agent that modulates the activity and/or expression of SLAMF7. In some embodiments, the immune checkpoint modulator is an agent that binds to SLAMF7 (e.g., an anti-SLAMF7 antibody). In some embodiments, the checkpoint modulator is an SLAMF7 agonist. In some embodiments, the checkpoint modulator is an SLAMF7 antagonist. In some embodiments, the immune checkpoint modulator is a SLAMF7-binding protein (e.g., an antibody) selected from the group consisting of elotuzumab (Bristol-Myers Squibb and AbbVie).

NKp80. NKp80 is also known as killer cell lectin-like receptor subfamily F, member 1. NKp80 surface expression was also detected in all CD3- and in 6/10 CD3$^+$ large granular lymphocyte expansions derived from patients with lymphoproliferative disease of granular lymphocytes. In polyclonal NK cells, mAb-mediated cross-linking of NKp80 resulted in induction of cytolytic activity and Ca' mobilization. A marked heterogeneity existed in the magnitude of the cytolytic responses of different NK cell clones to anti-NKp80 mAb. This heterogeneity correlated with the surface density of NKp46 molecules expressed by different NK clones. The mAb-mediated masking of NKp80 led to a partial inhibition of the NK-mediated lysis of appropriate allogeneic phytohemagglutinin-induced T cell blasts, while it had no effect on the lysis of different tumor target cells, including T cell leukemia cells. In some embodiments, the immune checkpoint modulator is an agent that modulates the activity and/or expression of NKp80. In some embodiments, the immune checkpoint modulator is an agent that binds to NKp80 (e.g., an anti-NKp80 antibody). In some embodiments, the checkpoint modulator is an NKp80 agonist. In some embodiments, the checkpoint modulator is an NKp80 antagonist.

CD30. CD30, also known as TNFRSF8, is a cell membrane protein of the tumor necrosis factor receptor family and tumor marker. This receptor is expressed by activated, but not by resting, T and B cells. TRAF2 and TRAF5 can interact with this receptor, and mediate the signal transduction that leads to the activation of NF-kappaB. It is a positive regulator of apoptosis, and also has been shown to limit the proliferative potential of autoreactive CD8 effector T cells and protect the body against autoimmunity. Two alternatively spliced transcript variants of this gene encoding distinct isoforms have been reported. CD30 is associated with anaplastic large cell lymphoma. It is expressed in embryonal carcinoma but not in seminoma and is thus a useful marker in distinguishing between these germ cell tumors. CD30 and CD15 are also expressed on classical Hodgkin Lymphoma Reed-Sternberg cells. In some embodiments, the immune checkpoint modulator is an agent that modulates the activity and/or expression of CD30. In some embodiments, the immune checkpoint modulator is an agent that binds to CD30 (e.g., an anti-CD30 antibody). In some embodiments, the checkpoint modulator is an CD30 agonist. In some embodiments, the checkpoint modulator is an CD30 antagonist. In some embodiments, the immune checkpoint modulator is a CD30-binding protein (e.g., an antibody) selected from the group consisting of brentuximab vedotin (Adcetris, Seattle Genetics).

BAFFR. BAFF receptor (B-cell activating factor receptor, BAFF-R), also known as tumor necrosis factor receptor superfamily member 13C (TNFRSF13C) and BLyS receptor 3 (BR3), is a membrane protein of the TNF receptor superfamily which recognizes BAFF. B-cell activating factor (BAFF) enhances B-cell survival in vitro and is a regulator of the peripheral B-cell population. The protein encoded by this gene is a receptor for BAFF and is a type III transmembrane protein containing a single extracellular phenylalanine-rich domain. It is thought that this receptor is the principal receptor required for BAFF-mediated mature B-cell survival. Overexpression of BAFF in mice results in mature B-cell hyperplasia and symptoms of systemic lupus erythematosus (SLE). Also, some SLE patients have increased levels of BAFF in serum. Therefore, it has been proposed that abnormally high levels of BAFF may contribute to the pathogenesis of autoimmune diseases by enhancing the survival of autoreactive B cells. In some embodiments, the immune checkpoint modulator is an agent that modulates the activity and/or expression of BAFFR. In some embodiments, the immune checkpoint modulator is an agent that binds to BAFFR (e.g., an anti-BAFFR antibody). In some embodiments, the checkpoint modulator is an BAFFR agonist. In some embodiments, the checkpoint modulator is an BAFFR antagonist.

HVEM. Herpesvirus entry mediator (HVEM), also known as tumor necrosis factor receptor superfamily member 14 (TNFRSF14), is a human cell surface receptor of the TNF-receptor superfamily. The protein encoded by this gene is a member of the TNF-receptor superfamily. This receptor was identified as a cellular mediator of herpes simplex virus (HSV) entry. Binding of HSV viral envelope glycoprotein D (gD) to this receptor protein has been shown to be part of the viral entry mechanism. The cytoplasmic region of this receptor was found to bind to several TRAF family members, which may mediate the signal transduction pathways that activate the immune response. In some embodiments, the immune checkpoint modulator is an agent that modulates the activity and/or expression of HVEM. In some embodiments, the immune checkpoint modulator is an agent that binds to HVEM (e.g., an anti-HVEM antibody). In some embodiments, the checkpoint modulator is an HVEM agonist. In some embodiments, the checkpoint modulator is an HVEM antagonist.

CD7. CD7 (Cluster of Differentiation 7) is a protein that in humans is encoded by the CD7 gene. This gene encodes a transmembrane protein which is a member of the immunoglobulin superfamily. This protein is found on thymocytes and mature T cells. It plays an essential role in T-cell interactions and also in T-cell/B-cell interaction during early lymphoid development. In some embodiments, the immune checkpoint modulator is an agent that modulates the activity and/or expression of CD7. In some embodiments, the immune checkpoint modulator is an agent that binds to CD7 (e.g., an anti-CD7 antibody). In some embodiments, the checkpoint modulator is an CD7 agonist. In some embodiments, the checkpoint modulator is an CD7 antagonist.

LIGHT. LIGHT, also known as tumor necrosis factor superfamily member 14 (TNFSF14), is a secreted protein of the TNF superfamily. It is recognized by herpesvirus entry mediator (HVEM), as well as decoy receptor 3. LIGHT stands for "homologous to lymphotoxin, exhibits inducible expression and competes with HSV glycoprotein D for binding to herpesvirus entry mediator, a receptor expressed on T lymphocytes". In the cluster of differentiation terminology it is classified as CD258. The protein encoded by this gene is a member of the tumor necrosis factor (TNF) ligand family. This protein is a ligand for TNFRSF14, which is a member of the tumor necrosis factor receptor superfamily, and which is also known as a herpesvirus entry mediator ligand (HVEML). This protein may function as a costimulatory factor for the activation of lymphoid cells and as a deterrent to infection by herpesvirus. This protein has been shown to stimulate the proliferation of T cells, and trigger apoptosis of various tumor cells. This protein is also reported to prevent tumor necrosis factor alpha mediated apoptosis in primary hepatocyte. Two alternatively spliced transcript variant encoding distinct isoforms have been reported. In some embodiments, the immune checkpoint modulator is an agent that modulates the activity and/or expression of LIGHT. In some embodiments, the immune checkpoint modulator is an agent that binds to LIGHT (e.g., an anti-LIGHT antibody). In some embodiments, the checkpoint modulator is an LIGHT agonist. In some embodiments, the checkpoint modulator is an LIGHT antagonist.

CD83. CD83 (Cluster of Differentiation 83) is a human protein encoded by the CD83 gene. CD83 is an integral membrane protein that belongs to the immunoglobulin superfamily. In immunology, this antigen has been extensively used for detecting activated/mature dendritic cells (DCs) since the original description of its expression selectivity toward these very efficient antigen-presenting cells. DCs are not the only cells that express CD83, which is also found transiently on a wide range of leukocytes. The protein encoded by this gene is a single-pass type I membrane protein and member of the immunoglobulin superfamily of receptors. The encoded protein may be involved in the regulation of antigen presentation. A soluble form of this protein can bind to dendritic cells and inhibit their maturation. Three transcript variants encoding different isoforms have been found for this gene. In some embodiments, the immune checkpoint modulator is an agent that modulates the activity and/or expression of CD83. In some embodiments, the immune checkpoint modulator is an agent that binds to CD83 (e.g., an anti-CD83 antibody). In some embodiments, the checkpoint modulator is an CD83 agonist. In some embodiments, the checkpoint modulator is an CD83 antagonist.

ii. Inhibitory Immune Checkpoint Molecules

ADORA2A. The adenosine A2A receptor (A2A4) is a member of the G protein-coupled receptor (GPCR) family which possess seven transmembrane alpha helices, and is regarded as an important checkpoint in cancer therapy. A2A receptor can negatively regulate overreactive immune cells (See, e.g., Ohta et al. (2001) *Nature* 414(6866): 916-20). Multiple immune checkpoint modulators specific for ADORA2A have been developed and may be used as disclosed herein. In some embodiments, the immune checkpoint modulator is an agent that modulates the activity and/or expression of ADORA2A. In some embodiments, the immune checkpoint modulator is an agent that binds to ADORA2A (e.g., an anti-ADORA2A antibody). In some embodiments, the immune checkpoint modulator is a ADORA2A-binding protein (e.g., an antibody). In some embodiments, the checkpoint modulator is an ADORA2A agonist. In some embodiments, the checkpoint modulator is an ADORA2A antagonist. ADORA2A-binding proteins (e.g., antibodies) are known in the art and are disclosed, e.g., in U.S. Patent Application Publication No. 2014/0322236, which is incorporated by reference herein.

B7-H3. B7-H3 (also known as CD276) belongs to the B7 superfamily, a group of molecules that costimulate or down-modulate T-cell responses. B7-H3 potently and consistently down-modulates human T-cell responses (See, e.g., Leitner et al. (2009) *Eur. J. Immunol.* 39(7): 1754-64). Multiple immune checkpoint modulators specific for B7-H3 have been developed and may be used as disclosed herein. In some embodiments, the immune checkpoint modulator is an agent that modulates the activity and/or expression of B7-H3. In some embodiments, the immune checkpoint modulator is an agent that binds to B7-H3 (e.g., an anti-B7-H3 antibody). In some embodiments, the checkpoint modulator is an B7-H3 agonist. In some embodiments, the checkpoint modulator is an B7-H3 antagonist. In some embodiments, the immune checkpoint modulator is an anti-B7-H3-binding protein selected from the group consisting of DS-5573 (Daiichi Sankyo, Inc.), enoblituzumab (MacroGenics, Inc.), and 8H9 (Sloan Kettering Institute for Cancer Research; See, e.g., Ahmed et al. (2015) *J. Biol. Chem.* 290(50): 30018-29). In some embodiments, the immune checkpoint modulator is a B7-H3-binding protein (e.g., an antibody). B7-H3-binding proteins (e.g., antibodies) are known in the art and are disclosed, e.g., in U.S. Pat. Nos. 9,371,395, 9,150,656, 9,062,110, 8,802,091, 8,501,471, 8,414,892; U.S. Patent Application Publication Nos. 2015/0352224, 2015/0297748, 2015/0259434, 2015/0274838, 2014/032875, 2014/0161814, 2013/0287798, 2013/0078234, 2013/0149236, 2012/02947960, 2010/0143245, 2002/0102264; PCT Publication Nos. WO 2016/106004, WO 2016/033225, WO 2015/181267, WO 2014/057687, WO 2012/147713, WO 2011/109400, WO 2008/116219, WO 2003/075846, WO 2002/032375; and Shi et al. (2016) *Mol. Med Rep.* 14(1): 943-8, each of which is incorporated by reference herein.

B7-H4. B7-H4 (also known as O8E, OV064, and V-set domain-containing T-cell activation inhibitor (VTCN1)), belongs to the B7 superfamily. By arresting cell cycle, B7-H4 ligation of T cells has a profound inhibitory effect on the growth, cytokine secretion, and development of cytotoxicity. Administration of B7-H4Ig into mice impairs antigen-specific T cell responses, whereas blockade of endogenous B7-H4 by specific monoclonal antibody promotes T cell responses (See, e.g., Sica et al. (2003) *Immunity* 18(6): 849-61). Multiple immune checkpoint modulators specific for B7-H4 have been developed and may be used as disclosed herein. In some embodiments, the immune checkpoint modulator is an agent that modulates the activity and/or expression of B7-H4. In some embodiments, the immune checkpoint modulator is an agent that binds to B7-H4 (e.g., an anti-B7-H4 antibody). In some embodiments, the immune checkpoint modulator is a B7-H4-binding protein (e.g., an antibody). In some embodiments, the checkpoint modulator is an B7-H4 agonist. In some embodiments, the checkpoint modulator is an B7-H4 antagonist. B7-H4-binding proteins (e.g., antibodies) are known in the art and are disclosed, e.g., in U.S. Pat. Nos. 9,296,822, 8,609,816, 8,759,490, 8,323,645; U.S. Patent Application Publication Nos. 2016/0159910, 2016/0017040, 2016/0168249, 2015/0315275, 2014/0134180, 2014/0322129, 2014/0356364, 2014/0328751, 2014/0294861, 2014/0308259, 2013/0058864, 2011/0085970, 2009/0074660, 2009/0208489; and PCT Publication Nos. WO 2016/040724, WO 2016/070001, WO 2014/159835, WO 2014/100483, WO 2014/100439, WO 2013/067492, WO 2013/025779, WO 2009/073533, WO 2007/067991, and WO 2006/104677, each of which is incorporated by reference herein.

BTLA. B and T Lymphocyte Attenuator (BTLA), also known as CD272, has HVEM (Herpesvirus Entry Mediator) as its ligand. Surface expression of BTLA is gradually downregulated during differentiation of human CD8$^+$ T cells from the naive to effector cell phenotype, however tumor-specific human CD8$^+$ T cells express high levels of BTLA (See, e.g., Derre et al. (2010) *J. Clin. Invest.* 120 (1): 157-67). Multiple immune checkpoint modulators specific for BTLA have been developed and may be used as disclosed herein. In some embodiments, the immune checkpoint modulator is an agent that modulates the activity and/or expression of BTLA. In some embodiments, the immune checkpoint modulator is an agent that binds to BTLA (e.g., an anti-BTLA antibody). In some embodiments, the immune checkpoint modulator is a BTLA-binding protein (e.g., an antibody). In some embodiments, the checkpoint modulator is an BTLA agonist. In some embodiments, the checkpoint modulator is an BTLA antagonist. BTLA-binding proteins (e.g., antibodies) are known in the art and are disclosed, e.g., in U.S. Pat. Nos. 9,346,882, 8,580,259, 8,563,694, 8,247,537; U.S. Patent Application Publication Nos. 2014/0017255, 2012/0288500, 2012/0183565, 2010/0172900; and PCT Publication Nos. WO 2011/014438, and WO 2008/076560, each of which is incorporated by reference herein.

CTLA-4. Cytotoxic T lymphocyte antigen-4 (CTLA-4) is a member of the immune regulatory CD28-B7 immunoglobulin superfamily and acts on naïve and resting T lymphocytes to promote immunosuppression through both B7-dependent and B7-independent pathways (See, e.g., Kim et al. (2016) *J. Immunol*. Res., Article ID 4683607, 14 pp.). CTLA-4 is also known as called CD152. CTLA-4 modulates the threshold for T cell activation. See, e.g., Gajewski et al. (2001) *J. Immunol.* 166(6): 3900-7. Multiple immune checkpoint modulators specific for CTLA-4 have been developed and may be used as disclosed herein. In some embodiments, the immune checkpoint modulator is an agent that modulates the activity and/or expression of CTLA-4. In some embodiments, the immune checkpoint modulator is an agent that binds to CTLA-4 (e.g., an anti-CTLA-4 antibody). In some embodiments, the checkpoint modulator is an CTLA-4 agonist. In some embodiments, the checkpoint modulator is an CTLA-4 antagonist. In some embodiments, the immune checkpoint modulator is a CTLA-4-binding protein (e.g., an antibody) selected from the group consisting of ipilimumab (Yervoy; Medarex/Bristol-Myers Squibb), tremelimumab (formerly ticilimumab; Pfizer/AstraZeneca), JMW-3B3 (University of Aberdeen), and AGEN1884 (Agenus). Additional CTLA-4 binding proteins (e.g., antibodies) are known in the art and are disclosed, e.g., in U.S. Pat. No. 8,697,845; U.S. Patent Application Publication Nos. 2014/0105914, 2013/0267688, 2012/0107320, 2009/0123477; and PCT Publication Nos. WO 2014/207064, WO 2012/120125, WO 2016/015675, WO 2010/097597, WO 2006/066568, and WO 2001/054732, each of which is incorporated by reference herein.

IDO. Indoleamine 2,3-dioxygenase (IDO) is a tryptophan catabolic enzyme with immune-inhibitory properties. Another important molecule is TDO, tryptophan 2,3-dioxygenase. IDO is known to suppress T and NK cells, generate and activate Tregs and myeloid-derived suppressor cells, and promote tumor angiogenesis. Prendergast et al., 2014, *Cancer Immunol Immunother.* 63 (7): 721-35, which is incorporated by reference herein. Multiple immune checkpoint modulators specific for IDO have been developed and may be used as disclosed herein. In some embodiments, the immune checkpoint modulator is an agent that modulates the activity and/or expression of IDO. In some embodiments, the immune checkpoint modulator is an agent that binds to IDO (e.g., an IDO binding protein, such as an anti-IDO antibody). In some embodiments, the checkpoint modulator is an IDO agonist. In some embodiments, the checkpoint modulator is an IDO antagonist. In some embodiments, the immune checkpoint modulator is selected from the group consisting of Norharmane, Rosmarinic acid, COX-2 inhibitors, alpha-methyl-tryptophan, and Epacadostat. In one embodiment, the modulator is Epacadostat.

MR. Killer immunoglobulin-like receptors (KIRs) comprise a diverse repertoire of MHCI binding molecules that negatively regulate natural killer (NK) cell function to protect cells from NK-mediated cell lysis. KIRs are generally expressed on NK cells but have also been detected on tumor specific CTLs. Multiple immune checkpoint modulators specific for KIR have been developed and may be used as disclosed herein. In some embodiments, the immune checkpoint modulator is an agent that modulates the activity and/or expression of KIR. In some embodiments, the immune checkpoint modulator is an agent that binds to KIR (e.g., an anti-KIR antibody). In some embodiments, the immune checkpoint modulator is a KIR-binding protein (e.g., an antibody). In some embodiments, the checkpoint modulator is an KIR agonist. In some embodiments, the checkpoint modulator is an KIR antagonist. In some embodiments the immune checkpoint modulator is lirilumab (also known as BMS-986015; Bristol-Myers Squibb). Additional KIR binding proteins (e.g., antibodies) are known in the art and are disclosed, e.g., in U.S. Pat. Nos. 8,981,065, 9,018,366, 9,067,997, 8,709,411, 8,637,258, 8,614,307, 8,551,483, 8,388,970, 8,119,775; U.S. Patent Application Publication Nos. 2015/0344576, 2015/0376275, 2016/0046712, 2015/0191547, 2015/0290316, 2015/0283234, 2015/0197569, 2014/0193430, 2013/0143269, 2013/0287770, 2012/0208237, 2011/0293627, 2009/0081240, 2010/0189723; and PCT Publication Nos. WO 2016/069589, WO 2015/069785, WO 2014/066532, WO 2014/055648, WO 2012/160448, WO 2012/071411, WO 2010/065939, WO 2008/084106, WO 2006/072625, WO 2006/072626, and WO 2006/003179, each of which is incorporated by reference herein.

LAG-3, Lymphocyte-activation gene 3 (LAG-3, also known as CD223) is a CD4-related transmembrane protein that competitively binds MHC II and acts as a co-inhibitory checkpoint for T cell activation (See, e.g., Goldberg and Drake (2011) Curr. Top. Microbiol. Immunol. 344: 269-78). Multiple immune checkpoint modulators specific for LAG-3 have been developed and may be used as disclosed herein. In some embodiments, the immune checkpoint modulator is an agent that modulates the activity and/or expression of LAG-3. In some embodiments, the immune checkpoint modulator is an agent that binds to LAG-3 (e.g., an anti-PD-1 antibody). In some embodiments, the checkpoint modulator is an LAG-3 agonist. In some embodiments, the checkpoint modulator is an LAG-3 antagonist. In some embodiments, the immune checkpoint modulator is a LAG-3-binding protein (e.g., an antibody) selected from the group consisting of Relatlimab (Bristol-Myers Squibb/Ono Pharmaceutical), Eftilagimod (also known as IMP321, Immutep), LAG525 (also known as IMP701, Immutep/Novartis), BI-754111 (Boehringer Ingelheim), TSR033 (AnaptysBio/Tesaro, Inc.), IMP-761 (Immutep/Prima Biomed), IBI110 (Cinda Biopharma), GSK-2831781 (also known as IMP731, Immutep/GlaxoSmithKline), MK-4280 (Merck & Co., Inc.) and REGN3767 (Regeneron/Sanofi). Additional LAG-3 binding proteins (e.g., antibodies) are known in the art and are disclosed, for example, in U.S. Pat. Nos. 10,266,591, 9,908, 936, 10, 358, 495, 10, 188, 730; U.S. Patent Application Publication Nos. 2019/233,513, 2019/169294; PCT Publication Nos. WO2019/141092, WO2017/220555, WO2019/129137, WO2018/069500, WO2014/008218, WO2017/037203, each of which is incorporated herein by reference.

PD-1. Programmed cell death protein 1 (PD-1, also known as CD279 and PDCD1) is an inhibitory receptor that negatively regulates the immune system. In contrast to CTLA-4 which mainly affects naïve T cells, PD-1 is more broadly expressed on immune cells and regulates mature T cell activity in peripheral tissues and in the tumor microenvironment. PD-1 inhibits T cell responses by interfering with T cell receptor signaling. PD-1 has two ligands, PD-L1 and PD-L2. Multiple immune checkpoint modulators specific for PD-1 have been developed and may be used as disclosed herein. In some embodiments, the immune checkpoint modulator is an agent that modulates the activity and/or expression of PD-1. In some embodiments, the immune checkpoint modulator is an agent that binds to PD-1 (e.g., an anti-PD-1 antibody). In some embodiments, the checkpoint modulator is an PD-1 agonist. In some embodiments, the checkpoint modulator is an PD-1 antagonist. In some embodiments, the immune checkpoint modulator is a PD-1-binding protein (e.g., an antibody) selected from the group consisting of pembrolizumab (Keytruda; formerly lambrolizumab; Merck & Co., Inc.), nivolumab (Opdivo; Bristol-Myers Squibb), pidilizumab (CT-011, CureTech), JS-001 (Shanghai Junshi Bioscience Co., Ltd.), SHR-1210 (Incyte/Jiangsu Hengrui Medicine Co., Ltd.), MEDI0680 (also known as AMP-514; Amplimmune Inc./Medimmune), PDR001 (Novartis), BGB-A317 (BeiGene Ltd.), TSR-042 (also known as ANB011; AnaptysBio/Tesaro, Inc.), REGN2810 (also known as cemiplimab, Regeneron Pharmaceuticals, Inc./Sanofi-Aventis), and PF-06801591 (Pfizer). Additional PD-1-binding proteins (e.g., antibodies) are known in the art and are disclosed, e.g., in U.S. Pat. Nos. 9,181,342, 8,927,697, 7,488,802, 7,029,674; U.S. Patent Application Publication Nos. 2015/0152180, 2011/0171215, 2011/0171220; and PCT Publication Nos. WO 2004/056875, WO 2015/036394, WO 2010/029435, WO 2010/029434, WO 2014/194302, each of which is incorporated by reference herein.

PD-L1/PD-L2. PD ligand 1 (PD-L1, also knows as B7-H1) and PD ligand 2 (PD-L2, also known as PDCD1LG2, CD273, and B7-DC) bind to the PD-1 receptor. Both ligands belong to the same B7 family as the B7-1 and B7-2 proteins that interact with CD28 and CTLA-4. PD-L1 can be expressed on many cell types including, for example, epithelial cells, endothelial cells, and immune cells. Ligation of PDL-1 decreases IFNγ, TNFα, and IL-2 production and stimulates production of IL10, an anti-inflammatory cytokine associated with decreased T cell reactivity and proliferation as well as antigen-specific T cell anergy. PDL-2 is predominantly expressed on antigen presenting cells (APCs). PDL2 ligation also results in T cell suppression, but where PDL-1-PD-1 interactions inhibits proliferation via cell cycle arrest in the G1/G2 phase, PDL2-PD-1 engagement has been shown to inhibit TCR-mediated signaling by blocking B7:CD28 signals at low antigen concentrations and reducing cytokine production at high antigen concentrations. Multiple immune checkpoint modulators specific for PD-L1 and PD-L2 have been developed and may be used as disclosed herein.

In some embodiments, the immune checkpoint modulator is an agent that modulates the activity and/or expression of PD-L1. In some embodiments, the immune checkpoint modulator is an agent that binds to PD-L1 (e.g., an anti-PD-L1 antibody). In some embodiments, the checkpoint modulator is an PD-L1 agonist. In some embodiments, the checkpoint modulator is an PD-L1 antagonist. In some embodiments, the immune checkpoint modulator is a PD-L1-binding protein (e.g., an antibody or a Fc-fusion protein) selected from the group consisting of durvalumab (also known as MEDI-4736; AstraZeneca/Celgene Corp./Medimmune), atezolizumab (Tecentriq; also known as MPDL3280A and RG7446; Genetech Inc.), avelumab (also known as MSB0010718C; Merck Serono/AstraZeneca); MDX-1105 (BMS-936559, Medarex/Bristol-Meyers Squibb), AMP-224 (Amplimmune, GlaxoSmithKline), LY3300054 (Eli Lilly and Co.), JS003 (Shanghai Junshi Bioscience Co., Ltd.), SHR-1316 (Jiangsu Hengrui Medicine Co., Ltd.), KN035 (Alphamab and 3D Medicines), or CK-301 (Checkpoint Therapeutics). Additional PD-L1-binding proteins are known in the art and are disclosed, e.g., in U.S. Patent Application Publication Nos. 2016/0084839, 2015/0355184, 2016/0175397, and PCT Publication Nos. WO 2014/100079, WO 2016/030350, WO2013181634, each of which is incorporated by reference herein.

In some embodiments, the immune checkpoint modulator is an agent that modulates the activity and/or expression of PD-L2. In some embodiments, the immune checkpoint modulator is an agent that binds to PD-L2 (e.g., an anti-PD-L2 antibody). In some embodiments, the checkpoint modulator is an PD-L2 agonist. In some embodiments, the checkpoint modulator is an PD-L2 antagonist. PD-L2-binding proteins (e.g., antibodies) are known in the art and are disclosed, e.g., in U.S. Pat. Nos. 9,255,147, 8,188,238; U.S. Patent Application Publication Nos. 2016/0122431, 2013/0243752, 2010/0278816, 2016/0137731, 2015/0197571, 2013/0291136, 2011/0271358; and PCT Publication Nos. WO 2014/022758, and WO 2010/036959, each of which is incorporated by reference herein.

TIM-3. T cell immunoglobulin mucin 3 (TIM-3, also known as Hepatitis A virus cellular receptor (HAVCR2)) is a A type I glycoprotein receptor that binds to 5-type lectin galectin-9 (Gal-9). TIM-3, is a widely expressed ligand on lymphocytes, liver, small intestine, thymus, kidney, spleen, lung, muscle, reticulocytes, and brain tissue. Tim-3 was originally identified as being selectively expressed on IFN-γ-secreting Th1 and Tc1 cells (Monney et al. (2002) Nature 415: 536-41). Binding of Gal-9 by the TIM-3 receptor triggers downstream signaling to negatively regulate T cell survival and function. Multiple immune checkpoint modulators specific for TIM-3 have been developed and may be used as disclosed herein. In some embodiments, the immune checkpoint modulator is an agent that modulates the activity and/or expression of TIM-3. In some embodiments, the immune checkpoint modulator is an agent that binds to TIM-3 (e.g., an anti-TIM-3 antibody). In some embodiments, the checkpoint modulator is an TIM-3 agonist. In some embodiments, the checkpoint modulator is an TIM-3 antagonist. In some embodiments, the immune checkpoint modulator is an anti-TIM-3 antibody selected from the group consisting of TSR-022 (AnaptysBio/Tesaro, Inc.) and MGB453 (Novartis). Additional TIM-3 binding proteins (e.g., antibodies) are known in the art and are disclosed, e.g., in U.S. Pat. Nos. 9,103,832, 8,552,156, 8,647,623, 8,841,418; U.S. Patent Application Publication Nos. 2016/0200815, 2015/0284468, 2014/0134639, 2014/0044728, 2012/0189617, 2015/0086574, 2013/0022623; and PCT Publication Nos. WO 2016/068802, WO 2016/068803, WO 2016/071448, WO 2011/155607, and WO 2013/006490, each of which is incorporated by reference herein.

VISTA. V-domain Ig suppressor of T cell activation (VISTA, also known as Platelet receptor Gi24) is an Ig super-family ligand that negatively regulates T cell responses. See, e.g., Wang et al., 2011, J. Exp. Med. 208: 577-92. VISTA expressed on APCs directly suppresses CD4+ and CD8+ T cell proliferation and cytokine production (Wang et al. (2010) J Exp Med. 208(3): 577-92). Multiple immune checkpoint modulators specific for VISTA have been developed and may be used as disclosed herein. In some embodiments, the immune checkpoint modulator is an agent that modulates the activity and/or expression of VISTA. In some embodiments, the immune checkpoint modulator is an agent that binds to VISTA (e.g., an anti-VISTA antibody). In some embodiments, the checkpoint modulator is an VISTA agonist. In some embodiments, the checkpoint modulator is an VISTA antagonist. In some embodiments, the immune checkpoint modulator is a VISTA-binding protein (e.g., an antibody) selected from the group consisting of TSR-022 (AnaptysBio/Tesaro, Inc.) and MGB453 (Novartis). VISTA-binding proteins (e.g., antibodies) are known in the art and are disclosed, e.g., in U.S. Patent Application Publication Nos. 2016/0096891; and PCT Publication Nos. WO 2014/190356, WO 2014/197849, WO 2014/190356 and WO 2016/094837, each of which is incorporated by reference herein.

CD160. CD160 is a 27 kDa glycoprotein which was initially identified with the monoclonal antibody BY55. Its expression is tightly associated with peripheral blood NK cells and CD8 T lymphocytes with cytolytic effector activity. The cDNA sequence of CD160 predicts a cysteine-rich, glycosylphosphatidylinositol-anchored protein of 181 amino acids with a single Ig-like domain weakly homologous to KIR2DL4 molecule. CD160 is expressed at the cell surface as a tightly disulfide-linked multimer. RNA blot analysis revealed CD160 mRNAs of 1.5 and 1.6 kb whose expression was highly restricted to circulating NK and T cells, spleen and small intestine. Within NK cells CD160 is expressed by CD56dimCD16+ cells whereas among circulating T cells its expression is mainly restricted to TCRgd bearing cells and to TCRab+CD8brightCD95+CD56+CD28-CD27-cells. In tissues, CD160 is expressed on all intestinal intraepithelial lymphocytes. CD160 shows a broad specificity for binding to both classical and nonclassical MHC class I molecules. CD160 is a ligand for HVEM, and considered a proposed immune checkpoint inhibitor with anti-cancer activity alongside with anti-PD-1 antibodies. CD160 has also been proposed as a potential new target in cases of human pathological ocular and tumor neoangiogenesis that do not respond or become resistant to existing antiangiogenic drugs. In some embodiments, the immune checkpoint modulator is an agent that modulates the activity and/or expression of CD160. In some embodiments, the immune checkpoint modulator is an agent that binds to CD160 (e.g., an anti-CD160 antibody). In some embodiments, the checkpoint modulator is an CD160 inhibitor. In some embodiments, the checkpoint modulator is an CD160 activator.

2B4. Natural Killer Cell Receptor 2B4 is also known as CD244 (Cluster of Differentiation 244), which is a human protein encoded by the CD244 gene. This gene encodes a cell surface receptor expressed on natural killer cells (NK cells) (and some T cells) mediating non-major histocompatibility complex (MHC) restricted killing. The interaction between NK-cell and target cells via this receptor is thought to modulate NK-cell cytolytic activity. Alternatively spliced transcript variants encoding different isoforms have been found for this gene. CD244 can also be expressed on non-lymphocytes such as eosinophils, mast cells and dendritic cells. In some embodiments, the immune checkpoint modulator is an agent that modulates the activity and/or expression of 2B4. In some embodiments, the immune checkpoint modulator is an agent that binds to 2B4 (e.g., an anti-2B4 antibody). In some embodiments, the checkpoint modulator is an 2B4 agonist. In some embodiments, the checkpoint modulator is an 2B4 antagonist.

TGF β. Transforming growth factor beta (TGF-β) is a multifunctional cytokine belonging to the transforming growth factor superfamily that includes four different isoforms (TGF-β1 to 4, HGNC symbols TGFB1, TGFB2, TGFB3, TGFB4) and many other signaling proteins produced by all white blood cell lineages.

In normal cells, TGF-β, acting through its signaling pathway, stops the cell cycle at the G1 stage to stop proliferation, induce differentiation, or promote apoptosis. In many cancer cells, parts of the TGF-β signaling pathway are mutated, and TGF-β no longer controls the cell. These cancer cells proliferate. The surrounding stromal cells (fibroblasts) also proliferate. Both cells increase their production of TGF-β. This TGF-β acts on the surrounding stromal cells, immune cells, endothelial and smooth-muscle cells. It causes immunosuppression and angiogenesis, which makes the cancer more invasive. TGF-β also converts effector T-cells, which normally attack cancer with an inflammatory (immune) reaction, into regulatory (suppressor) T-cells, which turn off the inflammatory reaction. Normal tissue integrity is preserved by feedback interactions between different cell types that express adhesion molecules and secrete cytokines. Disruption of these feedback mechanisms in cancer damages a tissue. When TGF-β signaling fails to control NF-κB activity in cancer cells, this has at least two potential effects: first, it enables the malignant tumor to persist in the presence of activated immune cells, and second, the cancer cell outlasts immune cells because it survives in the presence of apoptotic, and anti-inflammatory mediators. In some embodiments, the immune checkpoint modulator is an agent that modulates the activity and/or expression of TGF-β. In some embodiments, the immune checkpoint modulator is an agent that binds to TGF-β (e.g., an anti-TGF-β antibody). In some embodiments, the checkpoint modulator is an TGF-β agonist. In some embodiments, the checkpoint modulator is an TGF-β antagonist.

TIGIT. T cell immunoreceptor with Ig and ITIM domains (TIGIT) is an immune receptor present on some T cells and Natural Killer Cells (NK). It is also identified as WUCAM and Vstm3. TIGIT could bind to CD155(PVR) on dendritic cells (DCs), macrophages, etc. with high affinity, and also to CD112(PVRL2) with lower affinity.

TIGIT and PD-1 has been shown to be over expressed on tumor antigen-specific (TA-specific) CD8$^+$ T cells and CD8$^+$ tumor infiltrating lymphocytes (TILs) from individuals with melanoma. Chauvin et al., *J Clin Invest.* 125 (5): 2046-2058. Blockade of TIGIT and PD-1 led to increased cell proliferation, cytokine production, and degranulation of TA-specific CD8$^+$ T cells and TIL CD8$^+$ T cells. Co-blockade of TIGIT and PD-1 pathways elicits tumor rejection in pre-clinical murine models. Johnston et al., *Cancer Cell.* 26 (6): 923-937. In some embodiments, the immune checkpoint modulator is an agent that modulates the activity and/or expression of TIGIT. In some embodiments, the immune checkpoint modulator is an agent that binds to TIGIT (e.g., an anti-TIGIT antibody). In some embodiments, the checkpoint modulator is an TIGIT agonist. In some embodiments, the checkpoint modulator is an TIGIT antagonist.

LAIR1. Leukocyte-associated immunoglobulin-like receptor 1 (LAIR1) is a protein that in humans is encoded by the LAIR1 gene. LAIR1 has also been designated as CD305 (cluster of differentiation 305). The protein encoded by this gene is an inhibitory receptor found on peripheral mononuclear cells, including NK cells, T cells, and B cells. Inhibitory receptors regulate the immune response to prevent lysis of cells recognized as self. The gene is a member of both the immunoglobulin superfamily and the leukocyte-associated inhibitory receptor family. In some embodiments, the immune checkpoint modulator is an agent that modulates the activity and/or expression of LAIR1. In some embodiments, the immune checkpoint modulator is an agent that binds to LAIR1 (e.g., an anti-LAIR1 antibody). In some embodiments, the checkpoint modulator is an LAIR1 agonist. In some embodiments, the checkpoint modulator is an LAIR1 antagonist.

In some embodiments, the immune checkpoint molecule is PD-1, PD-L1, PD-L2, CTLA-4, TIM-3, LAG3, CD160, 2B4, TGF β, VISTA, BTLA, TIGIT or LAIR1 In some embodiments, the immune checkpoint molecule is OX40, CD2, CD27, ICAM-1, NKG2C, SLAMF7, NKp80, B7-H3, LFA-1, 1COS, 4-1BB, GITR, CD30, CD40, BAFFR, HVEM, CD7, LIGHT, or CD83. In a specific embodiment, the immune checkpoint molecule is PD-1. In a specific embodiment, the immune checkpoint molecule is PD-L1. In a specific embodiment, the immune checkpoint molecule is CTLA-4.

IV. Compositions

The present disclosure provides pharmaceutical compositions containing a MDM2 inhibitor disclosed herein, e.g., APG-115, for the treatment of cancer. The pharmaceutical composition of the present invention comprises one or more MDM2 inhibitors disclosed herein, or a pharmaceutically acceptable salt thereof, and a pharmaceutically acceptable carrier or diluent. The pharmaceutical composition of the present invention optionally comprises one or more modulators of immune checkpoint molecules disclosed in the present application.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present invention optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the *Handbook of Pharmaceutical Excipients* (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in *Remington's Pharmaceutical Sciences* (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

In some embodiments, the pharmaceutical composition for the combination therapy comprises a MDM2 inhibitor of the following structure known as APG-115

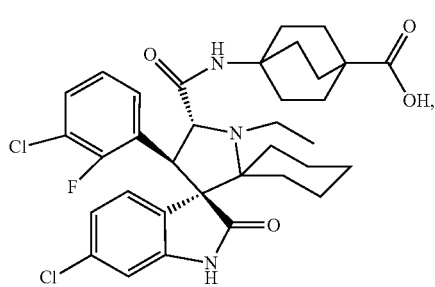 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt thereof. In some embodiments, the pharmaceutical composition is in a solid dose form. In some embodiments, the solid dose form is capsules. In some embodiments, the solid dose form is dry-filled capsules. In some embodiments, the solid dose form is dry-filled size 1 gelatin capsules. In some embodiments, the capsule comprises from about 10-500 mg of a MDM2 inhibitor, such as APG-115. In some embodiments, the pharmaceutical composition or capsule comprises silicified microcrystalline cellulose.

In some embodiments, the pharmaceutical composition or capsules comprises a MDM2, such as APG-115, in an amount of about 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 120 mg, 130 mg, 140 mg, 150 mg, 160 mg, 170 mg, 180 mg, 190 mg, 210 mg, 220 mg, 230 mg, 240 mg, 250 mg, 260 mg, 270 mg, 280 mg, 290 mg, or 300 mg.

V. Methods of Treatment

Provided herein are methods of treating a cancer in a subject in need thereof, comprising administering an effective amount of a MDM2 inhibitor of the present invention, and an effective amount of at least one modulator of an immune checkpoint molecule to the subject, such that the cancer is treated.

Also provided herein are methods of treating a cancer in a subject in need thereof, comprising administering an effective amount of a MDM2 inhibitor of the present invention to the subject, such that the cancer is treated. In certain embodiments, the cancer is selected from pancreatic cancer, adenoid cystic carcinoma, lung cancer, gastrointestinal stromal tumor, and breast cancer. In certain embodiments, the cancer is locally advanced or metastatic solid tumor or lymphoma. In certain embodiments, the subject is treatment-experienced and shows disease progression.

Provided herein are also methods of treating a cancer comprising administering to a subject in need thereof a therapeutically effective amount of a MDM2 inhibitor such as APG-115, wherein the method comprises at least one 28-day treatment cycle, wherein MDM2 inhibitor is administrated orally every other day for the first consecutive 3-weeks of the treatment cycle and is not administered during the forth week of the treatment cycle, wherein the therapeutically effective amount is from about 100 mg to about 200 mg of MDM2 inhibitor.

In certain embodiments, the therapeutically effective amount is about 100 mg of APG-115.

In other embodiment, the therapeutically effective amount is about 150 mg of APG-115

In another embodiment, the therapeutically effective amount is about 200 mg of APG-115.

In certain embodiments, the cancer is metastatic solid tumors, lymphomas, advanced soft tissue sarcoma, or adenoid cystic carcinoma.

MDM2 Inhibitors Compositions and Administration

The disclosure described herein apply to MDM2 inhibitor (e.g., APG-115) as a single agent treatment or as a co-agent in the combination therapy. In the methods of the invention, the MDM2 inhibitor (e.g., APG-115) can be administered in the form of a pharmaceutical composition, such as the compositions and formulations described herein. In some embodiments, the MDM2 inhibitor (e.g., APG-115) is administered in combination with the at least one immune checkpoint modulator is formulated for intravenous administration, administration by inhalation, topical administration, or oral administration.

In certain embodiments, the MDM2 inhibitor (e.g., APG-115) is administered in at least one dose per day. In certain embodiments, the MDM2 inhibitor (e.g., APG-115) is administered in at least two doses per day. In certain embodiments, the MDM2 inhibitor (e.g., APG-115) is administered in at least three dose per day. In certain embodiments, the MDM2 inhibitor (e.g., APG-115) is administered in one dose per day. In certain embodiments, the MDM2 inhibitor (e.g., APG-115) is administered in two doses per day. In certain embodiments, the MDM2 inhibitor (e.g., APG-115) is administered in three doses per day. Additional suitable treatment regimens for MDM2 inhibitor (e.g., APG-115) are provided, for example, in U.S. Pat. No. 9,745,314, the entire contents of which are expressly incorporated herein by reference.

One skilled in the art would be able, by routine experimentation, to determine what an effective, non-toxic amount of a MDM2 inhibitor (e.g., APG-115) would be for the purpose of treating cancers. For example, a therapeutically active amount of MDM2 inhibitor (e.g., APG-115) may vary according to factors such as the disease stage (e.g., stage I versus stage IV), age, sex, medical complications (e.g., immunosuppressed conditions or diseases) and weight of the subject, and the ability of the MDM2 inhibitor (e.g., APG-115) to elicit a desired response in the subject. The dosage regimen may be adjusted to provide the optimum therapeutic response. For example, several divided doses may be administered daily or administered by continuous infusion or the dose may be proportionally reduced as indicated by the exigencies of the therapeutic situation. In certain embodiments, a MDM2 inhibitor (e.g., APG-115) is administered in an amount that would be therapeutically effective if delivered alone, i.e., MDM2 inhibitor (e.g., APG-115) is administered and/or acts as a therapeutic anti-cancer agent, and not predominantly as an agent to ameliorate side effects of other chemotherapy or other cancer treatments.

In certain embodiments, a MDM2 inhibitor (e.g., APG-115) is administered in an amount that would be effective to improve or augment the immune response to the tumor, e.g., by augmenting the therapeutic effect of one or more immune checkpoint modulators. The dosages provided below may be used for any mode of administration of MDM2 inhibitor (e.g., APG-115), including topical administration, administration by inhalation, and intravenous administration (e.g. continuous infusion).

In certain embodiments, the subject is administered a dose of a MDM2 inhibitor (e.g., APG-115) in the range of about 0.5 mg/kg to about 10,000 mg/kg, about 5 mg/kg to about 5,000 mg/kg, about 10 mg/kg to about 3,000 mg/kg. In one embodiment, a MDM2 inhibitor (e.g., APG-115) is administered in the range of about 10 mg/kg to about 1,400 mg/kg. In one embodiment, MDM2 inhibitor (e.g., APG-115) is administered in the range of about 10 mg/kg to about 650 mg/kg. In one embodiment, a MDM2 inhibitor (e.g., APG-115) is administered in the range of about 10 mg/kg to about 200 mg/kg. In various embodiments, a MDM2 inhibitor (e.g., APG-115) is administered at a dose of about 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 120 mg/kg, 130 mg/kg, 140 mg/kg, 150 mg/kg, 160 mg/kg, 170 mg/kg, 180 mg/kg, 190 mg/kg, 210 mg/kg, 220 mg/kg, 230 mg/kg, 240 mg/kg, 250 mg/kg, 260 mg/kg, 270 mg/kg, 280 mg/kg, 290 mg/kg, or 300 mg/kg.

It should be understood that ranges having any one of these values as the upper or lower limits are also intended to be part of this invention, e.g., about 50 mg/kg to about 200 mg/kg, or about 650 mg/kg to about 1400 mg/kg. In one embodiment the administered dose is at least about 1 mg/kg, 2 mg/kg, at least about 5 mg/kg, at least about 10 mg/kg, at least about 12.5 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 60 mg/kg, at least about 65 mg/kg, at least about 70 mg/kg, at least about 75 mg/kg, at least about 80 mg/kg, at least about 85 mg/kg, at least about 90 mg/kg, at least about 95 mg/kg, at least about 100 mg/kg, at least about 104 mg/kg, at least about 125 mg/kg, at least about 150 mg/kg, at least about 175 mg/kg, at least about 200 mg/kg, at least about 250 mg/kg, at least about 300 mg/kg, or at least about 400 mg/kg.

In certain embodiments, the MDM2 inhibitor (e.g., APG-115) is administered at a dose of about 10 mg/kg/day (24 hours) to about 150 mg/kg/day (24 hours). In certain embodiments, the MDM2 inhibitor (e.g., APG-115) is administered at a dose selected from the group consisting of about 1 mg/kg/day (24 hours), about 2 mg/kg/day (24 hours), about 5 mg/kg/day (24 hours), about 10 mg/kg (24 hours), about 15 mg/kg/day (24 hours), about 20 mg/kg/day (24 hours), about 25 mg/kg/day (24 hours), about 30 mg/kg/day (24 hours), about 35 mg/kg/day (24 hours), about 40 mg/kg/day (24 hours), about 45 mg/kg/day (24 hours), about 50 mg/kg/day (24 hours), about 55 mg/kg/day (24 hours), about 60 mg/kg/day (24 hours), about 65 mg/kg/day (24 hours), 70 mg/kg/day (24 hours), about 75 mg/kg/day (24 hours), about 80 mg/kg/day (24 hours), about 85 mg/kg/day (24 hours), about 90 mg/kg/day (24 hours), about 95 mg/kg/day (24 hours), about 100 mg/kg/day (24 hours), about 105 mg/kg/day (24 hours), about 110 mg/kg/day (24 hours), about 120 mg/kg/day (24 hours), about 130 mg/kg/day (24 hours), about 140 mg/kg/day (24 hours), about 150 mg/kg/day (24 hours), about 160 mg/kg/day (24 hours), about 170 mg/kg/day (24 hours), about 180 mg/kg/day (24 hours), about 190 mg/kg/day (24 hours), about 200 mg/kg/day (24 hours), about 210 mg/kg/day (24 hours), about 220 mg/kg/day (24 hours), about 230 mg/kg/day (24 hours), about 240 mg/kg/day (24 hours), about 250 mg/kg/day (24 hours), about 260 mg/kg/day (24 hours), about 270 mg/kg/day (24 hours), about 280 mg/kg/day (24 hours), about 290 mg/kg/day (24 hours), and about 300 mg/kg/day (24 hours).

In certain embodiments, the MDM2 inhibitor (e.g., APG-115) is administered at a dose of about 10 mg/day (24 hours) to about 150 mg/day (24 hours). In certain embodiments, the MDM2 inhibitor (e.g., APG-115) is administered at a dose selected from the group consisting of about 1 mg/day (24 hours), about 2 mg/day (24 hours), about 5 mg/day (24 hours), about 10 mg/kg (24 hours), about 15 mg/day (24 hours), about 20 mg/day (24 hours), about 25 mg/day (24 hours), about 30 mg/day (24 hours), about 35 mg/kg/day (24 hours), about 40 mg/day (24 hours), about 45 mg/day (24 hours), about 50 mg/day (24 hours), about 55 mg/day (24 hours), about 60 mg/day (24 hours), about 65 mg/day (24 hours), 70 mg/day (24 hours), about 75 mg/day (24 hours), about 80 mg/day (24 hours), about 85 mg/day (24 hours), about 90 mg/day (24 hours), about 95 mg/day (24 hours), about 100 mg/day (24 hours), about 105 mg/day (24 hours), about 110 mg/day (24 hours), about 120 mg/day (24 hours), about 130 mg/day (24 hours), about 140 mg/day (24 hours), about 150 mg/day (24 hours), about 160 mg/day (24 hours), about 170 mg/day (24 hours), about 180 mg/day (24 hours), about 190 mg/day (24 hours), about 200 mg/day (24 hours), about 210 mg/day (24 hours), about 220 mg/day (24 hours), about 230 mg/day (24 hours), about 240 mg/day (24 hours), about 250 mg/day (24 hours), about 260 mg/day (24 hours), about 270 mg/day (24 hours), about 280 mg/day (24 hours), about 290 mg/day (24 hours), and about 300 mg/day (24 hours).

In certain embodiments, the MDM2 inhibitor (e.g., APG-115) is administered at a dose of about 10 mg/kg/week. In certain embodiments, the MDM2 inhibitor (e.g., APG-115) is administered at a dose of about 25 mg/kg/week. In certain embodiments, the MDM2 inhibitor (e.g., APG-115) is administered at a dose of about 50 mg/kg/week. In certain embodiments, the MDM2 inhibitor (e.g., APG-115) is administered at a dose of about 75 mg/kg/week. In certain embodiments, the MDM2 inhibitor (e.g., APG-115) is administered at a dose of about 100 mg/kg/week. In certain embodiments, the MDM2 inhibitor (e.g., APG-115) is administered at a dose of about 125 mg/kg/week. In certain embodiments, the MDM2 inhibitor (e.g., APG-115) is administered at a dose of about 150 mg/kg/week. In certain embodiments, the MDM2 inhibitor (e.g., APG-115) is administered at a dose selected from the group consisting of about 5 mg/kg/week, about 10 mg/kg/week, about 25 mg/kg/week, about 50 mg/kg/week, about 75 mg/kg/week, about 100 mg/kg/week, about 125 mg/kg/week, about 150 mg/kg/week, about 175 mg/kg/week, about 200 mg/kg/week, about 225 mg/kg/week, about 250 mg/kg/week, about 300 mg/kg/week, about 350 mg/kg/week, about 400 mg/kg week, about 450 mg/kg/week, about 500 mg/kg/week, about 550 mg/kg/week, about 600 mg/kg/week, about 650 mg/kg/week, and about 700 mg/kg/week.

In some embodiments, the MDM2 inhibitor (e.g., APG-115) is administered at a dosage that is different (e.g. lower) from the standard dosages of the MDM2 inhibitor used to treat the oncological disorder under the standard of care for treatment for a particular oncological disorder. In certain embodiments, the administered dosage of the MDM2 inhibitor (e.g., APG-115) is 5%, 10%, 20%, 30%, 40%, 50%, 60%, 70%, 80%, or 90% lower than the standard dosage of the MDM2 inhibitor (e.g., APG-115) molecule for a particular oncological disorder. In certain embodiments, the dosage administered of the MDM2 inhibitor (e.g., APG-115) molecule is 95%, 90%, 85%, 80%, 75%, 70%, 65%, 60%, 55%, 50%, 45%, 40%, 35%, 30%, 25%, 20%, 15%, 10% or 5% of the standard dosage of the MDM2 inhibitor (e.g., APG-115) molecule for a particular cancer.

In some embodiments, a MDM2 inhibitor, such as APG-115, or pharmaceutically acceptable salt thereof, is administered orally every other day (QOD). In some embodiments, the MDM2 inhibitor, such as APG-115, or pharmaceutically acceptable salt thereof, is administered orally in an amount from about 30 mg to about 250 mg every other day. In some embodiments, the MDM2 inhibitor, such as APG-115, or pharmaceutically acceptable salt thereof, is administered orally in an amount from about 50 mg to about 200 mg every other day. In some embodiments, the MDM2 inhibitor, such as APG-115, or pharmaceutically acceptable salt thereof, is administered orally in an amount of about 50 mg, 100 mg, 150 mg, or 200 mg every other day.

Notably, when a dose range from 10 mg/kg to 50 mg/kg for a MDM2 inhibitor (e.g., APG-115) was used in mice as disclosed in the examples provided herein, the corresponding clinically relevant doses are 48.8 and 244 mg/day for a 60 kg human, respectively. A factor of 12.3 was used for converting mouse dose to human equivalent dose (HED) here. To convert animal dose in mg/kg to HED mg/m², multiply by km⁺. See "Guidance for Industry Estimating the Maximum Safe Starting Dose in Initial Clinical Trials for Therapeutics in Adult Healthy Volunteers" U.S. Department of Health and Human Services, Food and Drug Administration, Center for Drug Evaluation and Research (CDER), July 2005, Pharmacology and Toxicology.

Modulators of Immune Checkpoint Molecules

Methods are provided for the treatment of cancers by administering a MDM2 inhibitor composition in combination with at least one immune checkpoint modulator to a subject. In certain embodiments, the immune checkpoint modulator stimulates the immune response of the subject. For example, in some embodiments, the immune checkpoint modulator stimulates or increases the expression or activity of a stimulatory immune checkpoint (e.g. CD28, CD122, ICOS, OX40, CD2, CD27, ICAM-1, NKG2C, SLAMF7, NKp80, B7-H3, LFA-1, 1COS, 4-1BB, GITR, CD30, CD40, BAFFR, HVEM, CD7, LIGHT, or CD83). In some embodiments, the immune checkpoint modulator inhibits or decreases the expression or activity of an inhibitory immune checkpoint (e.g. A2A4, B7-H3, B7-H4, IDO, KIR, PD-1, PD-L1, PD-L2, CTLA-4, TIM-3, LAG3, CD160, 2B4, TGF β, VISTA, BTLA, TIGIT or LAIR1).

In certain embodiments the immune checkpoint modulator targets an immune checkpoint molecule selected from the group consisting of OX40, CD2, CD27, ICAM-1, NKG2C, SLAMF7, NKp80, B7-H3, LFA-1, 1COS, 4-1BB, GITR, CD30, CD40, BAFFR, HVEM, CD7, LIGHT, and CD83. In certain embodiments the immune checkpoint modulator targets an immune checkpoint molecule selected from the group consisting of PD-1, PD-L1, PD-L2, CTLA-4, TIM-3, LAG3, CD160, 2B4, TGF β, VISTA, BTLA, TIGIT and LAIR1. In a particular embodiment, the immune checkpoint modulator targets an immune checkpoint molecule of PD-1. In a particular embodiment, the immune checkpoint modulator targets an immune checkpoint molecule of PD-L1. In a particular embodiment, the immune checkpoint modulator targets an immune checkpoint molecule of CTLA-4.

In certain embodiments, the immune checkpoint modulator is pembrolizumab, ipilimumab, nivolumab, atezolizumab, avelumab or durvalumab. In certain embodiments, the immune checkpoint modulator is AGEN-1884, BMS-986016, CS-1002, LAG525, MBG453, MEDI-570, OREG-103/BY40, lirilumab, or tremelimumab. In certain embodiments, the immune checkpoint modulator is pembrolizumab, nivolumab, AMP-224, AMP-514, BGB-A317, cemiplimab, JS001, CS1001, PDR-001, PF-06801591, IBI-308, pidilizumab, SHR-1210, or TSR-042. In certain embodiments, the immune checkpoint modulator is atezolizumab, avelumab, durvalumab, AMP-224, JS003, LY3300054, MDX-1105, SHR-1316, KN035, or CK-301.

In certain embodiments, the modulator of the immune checkpoint molecule restores anti-tumor T-cell activity. In certain embodiments, the modulator of the immune checkpoint molecule blocks T-cell-inhibitory cell activity. In certain embodiments, the modulator of the immune checkpoint molecule is an activator of the co-stimulatory checkpoint molecule, and the activator of co-stimulatory checkpoint molecule alters co-stimulatory signal required for full T-cell activation.

In some embodiments, more than one (e.g. 2, 3, 4, 5 or more) immune checkpoint modulator is administered to the subject. Where more than one immune checkpoint modulator is administered, the modulators may each target a stimulatory immune checkpoint molecule, or each target an inhibitory immune checkpoint molecule. In other embodiments, the immune checkpoint modulators include at least one modulator targeting a stimulatory immune checkpoint and at least one immune checkpoint modulator targeting an inhibitory immune checkpoint molecule.

In certain embodiments, the immune checkpoint modulator is a binding protein, for example, an antibody. The term "binding protein", as used herein, refers to a protein or polypeptide that can specifically bind to a target molecule, e.g. an immune checkpoint molecule. In some embodiments the binding protein is an antibody or antigen binding portion thereof, and the target molecule is an immune checkpoint molecule. In some embodiments the binding protein is a protein or polypeptide that specifically binds to a target molecule (e.g., an immune checkpoint molecule). In some embodiments the binding protein is a ligand. In some embodiments, the binding protein is a fusion protein. In some embodiments, the binding protein is a receptor. Examples of binding proteins that may be used in the methods of the invention include, but are not limited to, a humanized antibody, an antibody Fab fragment, a divalent antibody, an antibody drug conjugate, a scFv, a fusion protein, a bivalent antibody, and a tetravalent antibody.

The term "antibody", as used herein, refers to any immunoglobulin (Ig) molecule comprised of four polypeptide chains, two heavy (H) chains and two light (L) chains, or any functional fragment, mutant, variant, or derivation thereof. Such mutant, variant, or derivative antibody formats are known in the art. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody is a full-length antibody. In some embodiments, the antibody is a murine antibody. In some embodiments, the antibody is a human antibody. In some embodiments, the antibody is a humanized antibody. In some embodiments, the antibody is a monoclonal antibody. In other embodiments, the antibody is a chimeric antibody. Chimeric and humanized antibodies may be prepared by methods well known to those of skill in the art including CDR grafting approaches (See, e.g., U.S. Pat. Nos. 5,843,708; 6,180,370; 5,693,762; 5,585,089; and 5,530,101), chain shuffling strategies (See, e.g., U.S. Pat. No. 5,565,332; Rader et al. (1998) PROC. NAT'L. ACAD. SCI. USA 95: 8910-8915), molecular modeling strategies (U.S. Pat. No. 5,639,641), and the like.

The term "antigen-binding portion" or "antigen-binding fragment" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody.

Such antibody embodiments may also be bispecific, dual specific, or multi-specific formats; specifically binding to two or more different antigens. Examples of binding fragments encompassed within the term "antigen-binding portion" or "antigen-binding fragment" of an antibody include (i) a Fab fragment, a monovalent fragment consisting of the VL, VH, $C_L$ and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) NATURE 341: 544-546; and WO 90/05144 A1, the contents of which are herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al. (1988) SCIENCE 242:423-426; and Huston et al. (1988) PROC. NAT'L. ACAD. SCI. USA 85:5879-5883). Such single chain antibodies are also intended to be encompassed within the term "antigen-binding portion" or "antigen-binding fragment" of an antibody. Other forms of single chain antibodies, such as diabodies are also encompassed. Antigen binding portions can also be incorporated into single domain antibodies, maxibodies, minibodies, nanobodies, intrabodies, diabodies, triabodies, tetrabodies, v-NAR and bis-scFv (See, e.g., Hollinger and Hudson, Nature Biotechnology 23:1126-1136, 2005).

In some embodiment, the modulator of an immune checkpoint molecule is a monoclonal antibody or an antigen binding fragment thereof. As used herein, a "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (e.g., Fab, Fab', F(ab')$_2$, F$_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers found that certain sub-portions within Kabat CDRs adopt nearly identical peptide backbone conformations, despite having great diversity at the level of amino acid sequence (Chothia et al. (1987) J. MOL. BIOL. 196: 901-917, and Chothia et al. (1989) NATURE 342: 877-883). These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (1995) FASEB J. 9: 133-139, and MacCallum et al. (1996) J. MOL. BIOL. 262(5): 732-45. Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

The term "humanized antibody", as used herein refers to non-human (e.g., murine) antibodies that are chimeric immunoglobulins, immunoglobulin chains, or fragments thereof (such as Fv, Fab, Fab', F(ab')2 or other antigen-binding subsequences of antibodies) which contain minimal sequence derived from a non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, See Jones et al. (1986) NATURE 321: 522-525; Reichmann et al. (1988) NATURE 332: 323-329; and Presta (1992) CURR. OP. STRUCT. BIOL. 2: 593-596, each of which is incorporated by reference herein in its entirety.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate.

As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

A "bivalent antibody" refers to an antibody or antigen-binding fragment thereof that comprises two antigen-binding sites. The two antigen binding sites may bind to the same antigen, or they may each bind to a different antigen, in which case the antibody or antigen-binding fragment is characterized as "bispecific." A "tetravalent antibody" refers to an antibody or antigen-binding fragment thereof that comprises four antigen-binding sites. In certain embodiments, the tetravalent antibody is bispecific. In certain embodiments, the tetravalent antibody is multispecific, i.e. binding to more than two different antigens.

Fab (fragment antigen binding) antibody fragments are immunoreactive polypeptides comprising monovalent antigen-binding domains of an antibody composed of a polypeptide consisting of a heavy chain variable region ($V_H$) and heavy chain constant region 1 ($C_{H1}$) portion and a polypeptide consisting of a light chain variable ($V_L$) and light chain constant ($C_L$) portion, in which the $C_L$ and $CH_1$ portions are bound together, preferably by a disulfide bond between Cys residues.

In a particular embodiment, the immune checkpoint modulator is a fusion protein, for example, a fusion protein that modulates the activity of an immune checkpoint modulator. In one embodiment, the immune checkpoint modulator is a therapeutic nucleic acid molecule, for example a nucleic acid that modulates the expression of an immune checkpoint protein or mRNA. Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. In certain embodiments, the nucleic acid therapeutic is targeted against a nucleic acid sequence encoding an immune checkpoint protein.

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, See Dias, N. et al., (2002) Mol Cancer Ther 1:347-355. The antisense RNA molecule may have about 15-30 nucleotides that are complementary to the target mRNA. Patents directed to antisense nucleic acids, chemical modifications, and therapeutic uses include, for example: U.S. Pat. No. 5,898,031 related to chemically modified RNA-containing therapeutic compounds; U.S. Pat. No. 6,107,094 related methods of using these compounds as therapeutic agents; U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality of RNA nucleosides and at least one chemical modification. The entire contents of each of the patents listed in this paragraph are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (See, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in WO/2012/037254, and WO 2009/073809, the entire contents of each of which are incorporated herein by reference.

Immune checkpoint modulators may be administered at appropriate dosages to treat the oncological disorder, for example, by using standard dosages. One skilled in the art would be able, by routine experimentation, to determine what an effective, non-toxic amount of an immune checkpoint modulator would be for the purpose of treating cancers. Standard dosages of immune checkpoint modulators are known to a person skilled in the art and may be obtained, for example, from the product insert provided by the manufacturer of the immune checkpoint modulator. Examples of standard dosages of immune checkpoint modulators are provided in Table A below. In other embodiments, the immune checkpoint modulator is administered at a dosage that is different (e.g. lower) than the standard dosages of the immune checkpoint modulator used to treat the oncological disorder under the standard of care for treatment for a particular oncological disorder.

TABLE A

Exemplary Standard Dosages of Immune Checkpoint Modulators

| Immune Checkpoint Modulator | Immune Checkpoint Molecule | Exemplary Standard Dosage |
|---|---|---|
| Ipilimumab (Yervoy ®) | CTLA-4 | 3 mg/kg administered intravenously over 90 minutes every 3 weeks for a total of 4 doses. |
| Pembrolizumab (Keytruda ®) | PD-1 | 2 mg/kg administered as an intravenous infusion over 30 minutes every 3 weeks until disease progression or unacceptable toxicity. |
| Nivolumab (OPDIVO ®) | PD-1 | 3 mg/kg as an intravenous infusion over 60 minutes every 2 weeks. |
| Atezolizumab (Tecentriq ®) | PD-L1 | 1200 mg administered as an intravenous infusion over 60 minutes every 3 weeks |
| Avelumab (BAVENCIO ®) | PD-L1 | 10 mg/kg as an intravenous infusion over 60 minutes every 2 weeks. |
| Durvalumab (IMFINZI ®) | PD-L1 | 10 mg/kg as an intravenous infusion over 60 minutes every 2 weeks. |

In certain embodiments, the administered dosage of the immune checkpoint modulator is 5%, 10%, 20%, 30%, 40%, 50%, 60%, 70%, 80%, or 90% lower than the standard dosage of the immune checkpoint modulator for a particular cancer. In certain embodiments, the dosage administered of the immune checkpoint modulator is 95%, 90%, 85%, 80%, 75%, 70%, 65%, 60%, 55%, 50%, 45%, 40%, 35%, 30%, 25%, 20%, 15%, 10% or 5% of the standard dosage of the immune checkpoint modulator for a particular oncological disorder. In one embodiment, where a combination of immune checkpoint modulators are administered, at least one of the immune checkpoint modulators is administered at a dose that is lower than the standard dosage of the immune checkpoint modulator for a particular oncological disorder. In one embodiment, where a combination of immune checkpoint modulators are administered, at least two of the immune checkpoint modulators are administered at a dose that is lower than the standard dosage of the immune checkpoint modulators for a particular oncological disorder. In one embodiment, where a combination of immune checkpoint modulators are administered, at least three of the immune checkpoint modulators are administered at a dose that is lower than the standard dosage of the immune checkpoint modulators for a particular oncological disorder. In one embodiment, where a combination of immune checkpoint modulators are administered, all of the immune checkpoint modulators are administered at a dose that is lower than the standard dosage of the immune checkpoint modulators for a particular oncological disorder. In some embodiments, the immune checkpoint modulator is administered at a dose that is lower than the standard dosage of the immune checkpoint modulator, and the MDM2 inhibitor (e.g., APG-115) is administered at a dose that is lower than the standard dosage of the MDM2 inhibitor.

Co-Administration of a MDM2 Inhibitor and a Modulator of Immune Checkpoint Molecule As used herein, the term "co-administering" or "co-administration" refers to administration of a MDM2 inhibitor (e.g., APG-115) prior to, concurrently or substantially concurrently with, subsequently to, or intermittently with the administration of the immune checkpoint modulator. In certain embodiments, a MDM2 inhibitor (e.g., APG-115) is administered prior to administration of the immune checkpoint modulator. In certain embodiments, a MDM2 inhibitor (e.g., APG-115) is administered prior to and concurrently with the immune checkpoint modulator. In certain embodiments, a MDM2 inhibitor (e.g., APG-115) is administered prior to but not concurrently with the immune checkpoint modulator, i.e., a MDM2 inhibitor (e.g., APG-115) administration is discontinued prior to initiation of treatment with or administration of an immune checkpoint modulator. In certain embodiments, a MDM2 inhibitor (e.g., APG-115) is administered concurrently with the immune checkpoint modulator. In certain embodiments, a MDM2 inhibitor (e.g., APG-115) is administered after administration of the immune checkpoint modulator. In certain embodiments, a MDM2 inhibitor (e.g., APG-115) is administered concurrently with and after administration of the immune checkpoint modulator. In certain embodiments, a MDM2 inhibitor (e.g., APG-115) is administered after administration of the immune checkpoint modulator but not concurrently with the immune checkpoint modulator, i.e. administration of the immune checkpoint modulator is discontinued before initiating administration of a MDM2 inhibitor (e.g., APG-115).

A MDM2 inhibitor (e.g., APG-115) and/or pharmaceutical compositions thereof and the immune checkpoint modulator can act additively or, more preferably, synergistically. In one embodiment, the MDM2 inhibitor (e.g., APG-115) and immune checkpoint modulator act synergistically. In some embodiments the synergistic effects are in the treatment of the cancer. For example, in one embodiment, the combination of a MDM2 inhibitor (e.g., APG-115) and the immune checkpoint modulator improves the durability, i.e. extends the duration, of the immune response against the cancer that is targeted by the immune checkpoint modulator. In other embodiments the synergistic effects are in modulation of the toxicity associated with the immune checkpoint modulator. In one embodiment, a MDM2 inhibitor (e.g., APG-115) and the immune checkpoint modulator act additively.

The combination therapies of the present invention may be utilized for the treatment of cancers. In some embodiments, the combination therapy of a MDM2 inhibitor (e.g., APG-115) and an immune checkpoint modulator inhibits tumor cell growth. Accordingly, the invention further provides methods of inhibiting tumor cell growth in a subject, comprising administering a MDM2 inhibitor (e.g., APG-115) and at least one immune checkpoint modulator to the subject, such that tumor cell growth is inhibited. In certain embodiments, treating cancer comprises extending survival or extending time to tumor progression as compared to control, e.g., a population control. In certain embodiments, the subject is a human subject. In preferred embodiments, the subject is identified as having a tumor prior to administration of the first dose of a MDM2 inhibitor (e.g., APG-115) or the first dose of the immune checkpoint modulator. In certain embodiments, the subject has a tumor at the time of the first administration of a MDM2 inhibitor (e.g., APG-115) or at the time of first administration of the immune checkpoint modulator.

The immune checkpoint modulators are administered at a time relative to administration of the a MDM2 inhibitor (e.g., APG-115) such that the desired therapeutic effect, e.g. a therapeutic or synergistic effect, is achieved. For example, in certain embodiments a sufficient amount of time following administration of a MDM2 inhibitor (e.g., APG-115) may be desirable to effectively augment the efficacy of the immune checkpoint modulator relative to the efficacy of the immune checkpoint modulator alone, or to improve the durability of the effect. In certain embodiments, administration of a MDM2 inhibitor (e.g., APG-115) is initiated at least 2 hours, at least 4 hours, at least 6 hours, at least 8 hours, at least 12 hours, at least 18 hours, at least 24 hours, at least 36 hours, at least 48 hours, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, or at least 8 weeks prior to administration of the first dose of an immune checkpoint modulator. In particular embodiments of the methods of the invention, administration of the at least one immune checkpoint modulator may be initiated at least 24 hours after administration of a MDM2 inhibitor (e.g., APG-115) is initiated, one or more weeks after administration of a MDM2 inhibitor (e.g., APG-115) is initiated, two or more weeks after administration of a MDM2 inhibitor (e.g., APG-115) is initiated, three or more weeks after administration of a MDM2 inhibitor (e.g., APG-115) is initiated, four or more weeks after administration of a MDM2 inhibitor (e.g., APG-115) is initiated, five or more weeks after administration of a MDM2 inhibitor (e.g., APG-115) is initiated, six or more weeks after administration of a MDM2 inhibitor (e.g., APG-115) is initiated, seven or more weeks after administration of a MDM2 inhibitor (e.g., APG-115) is initiated, or eight or more weeks after administration of a MDM2 inhibitor (e.g., APG-115) is initiated. In some embodiments, administration of the at least one immune checkpoint modulator is initiated at least 24 hours after administration of a MDM2 inhibitor (e.g., APG-115) is initiated. In one embodiments administration of the at least one immune checkpoint modulator is initiated from 24 hours to 4 weeks after administration of a MDM2 inhibitor (e.g., APG-115) is initiated. In one embodiment, administration of the at least one immune checkpoint modulator is initiated from 24 hours to 1 week, from 1 to 2 weeks, from 1 to 3 weeks, or from 2 to 4 weeks after administration of a MDM2 inhibitor (e.g., APG-115) is initiated.

In one embodiment, administration of the at least one immune checkpoint modulator is initiated about 1 week after administration of a MDM2 inhibitor (e.g., APG-115) is initiated. In one embodiment, administration of the at least one immune checkpoint modulator is initiated about 2 weeks after administration of a MDM2 inhibitor (e.g., APG-115) is initiated. In one embodiment, administration of the at least one immune checkpoint modulator is initiated about 3 weeks after administration of a MDM2 inhibitor (e.g., APG-115) is initiated. In one embodiment, administration of the at least one immune checkpoint modulator is initiated about 4 weeks after administration of a MDM2 inhibitor (e.g., APG-115) is initiated. In one embodiment, administration of the at least one immune checkpoint modulator is initiated about 5 weeks after administration of a MDM2 inhibitor (e.g., APG-115) is initiated. In one embodiment, administration of the at least one immune checkpoint modulator is initiated about 6 weeks after administration of a MDM2 inhibitor (e.g., APG-115) is initiated. In one embodiment, administration of the at least one immune checkpoint modulator is initiated about 7 weeks after administration of a MDM2 inhibitor (e.g., APG-115) is initiated. In one embodiment, administration of the at least one immune checkpoint modulator is initiated about 8 weeks after administration of a MDM2 inhibitor (e.g., APG-115) is initiated.

In certain embodiments, a loading dose of a MDM2 inhibitor (e.g., APG-115) is administered prior to administration of the immune checkpoint modulator. In certain embodiments, a MDM2 inhibitor (e.g., APG-115) is administered to achieve a steady state level of a MDM2 inhibitor (e.g., APG-115) prior to administration of the immune checkpoint modulator. Where the combination therapy includes intravenous MDM2 inhibitor (e.g., APG-115) formulations, the subject is intravenously administered the a MDM2 inhibitor (e.g., APG-115) at as dose such that cancers are treated or prevented. In one embodiment, the subject is intravenously administered a MDM2 inhibitor (e.g., APG-115) such that response to the immune checkpoint modulator is improved, e.g., relative to treatment with the immune checkpoint modulator alone.

In one embodiment, the administration of a MDM2 inhibitor (e.g., APG-115) is discontinued before initiation of treatment with the immune checkpoint modulator, i.e., treatment with the immune checkpoint modulator excludes treatment with a MDM2 inhibitor (e.g., APG-115). In one embodiment, the administration of a MDM2 inhibitor (e.g., APG-115) is continued or resumed after initiation of treatment with the immune checkpoint modulator such that the a MDM2 inhibitor (e.g., APG-115) and immune checkpoint modulator are concurrently administered, e.g., for at least one cycle.

In some embodiments, the combination therapy for treating cancer comprises at least one 21-day treatment cycle, wherein the MDM2 inhibitor, or pharmaceutically acceptable salt thereof, is administered orally every other day in a patient in need thereof for the first two consecutive weeks of a 21-day treatment cycle and is not administered during the third week of the treatment cycle.

In some embodiments, the MDM2 inhibitor, such as APG-115, or pharmaceutically acceptable salt thereof, is administered orally in the patient on day 1, 3, 5, 7, 9, 11, and 13 of the 21-day treatment cycle.

In some embodiments, the MDM2 inhibitor, such as APG-115, or pharmaceutically acceptable salt thereof, is not administered on day 14-21 of the 21-day treatment cycle.

In some embodiments, the MDM2 inhibitor, such as APG-115, or pharmaceutically acceptable salt thereof, is administered orally in the patient in an amount from about 50 mg to about 200 mg on day 1, 3, 5, 7, 9, 11, and 13 of the 21-day treatment cycle.

In some embodiments, the MDM2 inhibitor, such as APG-115, or pharmaceutically acceptable salt thereof, is administered orally in the patient in an amount of about 50 mg on day 1, 3, 5, 7, 9, 11, and 13 of the 21-day treatment cycle.

In some embodiments, the MDM2 inhibitor, such as APG-115, or pharmaceutically acceptable salt thereof, is administered orally in the patient in an amount of about 100 mg on day 1, 3, 5, 7, 9, 11, and 13 of the 21-day treatment cycle.

In some embodiments, the MDM2 inhibitor, such as APG-115, or pharmaceutically acceptable salt thereof, is administered orally in the patient in an amount of about 150 mg on day 1, 3, 5, 7, 9, 11, and 13 of the 21-day treatment cycle.

In some embodiments, the MDM2 inhibitor, such as APG-115, or pharmaceutically acceptable salt thereof, is administered orally in the patient in an amount of about 200 mg on day 1, 3, 5, 7, 9, 11, and 13 of the 21-day treatment cycle.

In some embodiments, PD-1 modulator is administered via intravenous infusion in an amount of 200 mg on day 1 of the 21-day treatment cycle.

In some embodiments, the combination therapy comprises at least 1, 2, 3, 4, 5, 6, 7, 8, 9, 10, 11, or 12 of the 21-day treatment cycle. In some embodiments, the combination therapy continues until disease progression or unacceptable toxicity.

In certain embodiments, at least 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

It should be noted that more than one immune checkpoint modulator e.g., 2, 3, 4, 5, or more immune checkpoint modulators, may be administered in combination with a MDM2 inhibitor (e.g., APG-115). For example, in one embodiment, two immune checkpoint modulators may be administered in combination with a MDM2 inhibitor (e.g., APG-115). In one embodiment, three immune checkpoint modulators may be administered in combination with a MDM2 inhibitor (e.g., APG-115). In one embodiment, four immune checkpoint modulators may be administered in combination with a MDM2 inhibitor (e.g., APG-115). In one embodiment, five immune checkpoint modulators may be administered in combination with a MDM2 inhibitor (e.g., APG-115). In some embodiments, the two or more immune checkpoint modulators target the same immune checkpoint molecule. In some embodiments, the two or more immune checkpoint modulators each target different immune checkpoint molecules.

In general, the combination therapy including a MDM2 inhibitor (e.g., APG-115) and the immune checkpoint modulators described herein or the MDM2 inhibitor (e.g., APG-115) as a single therapy may be used to therapeutically treat cancers. In various embodiments the oncological disorder is selected from the group consisting of leukemia, a lymphoma, a melanoma, a carcinoma, and a sarcoma. In a particular embodiment, the combination therapy is used to treat solid tumors. In various embodiments of the invention, the combination therapy is used for treatment or prevention of cancer cancer is selected from the group consisting of adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, head and neck cancer, Hodgkin disease, Kaposi sarcoma, kidney cancer, laryngeal and hypopharyngeal cancer, leukemia—acute lymphocytic (ALL) in adults, leukemia—acute myeloid (AML), leukemia—chronic lymphocytic (CLL), leukemia—chronic myeloid (CML), leukemia—chronic myelomonocytic (CMML), leukemia in children, liver cancer, lung cancer—non-small cell, lung cancer—small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer—basal and squamous cell, skin cancer—melanoma, small intestine cancer, stomach cancer, testicular cancer, thymus cancer, thyroid cancer, uterine sarcoma, vaginal cancer, vulvar cancer, Waldenstrom macroglobulinemia, and Wilms Tumor. In one embodiment, the combination therapy is used to treat cancer selected from the group consisting of melanoma, Hodgkin lymphoma, lung cancer, kidney cancer, bladder cancer, head and neck cancer, Merkel cell carcinoma, urothelial carcinoma, Solid tumors that are microsatellite instability—high or mismatch repair-deficient, sarcoma, colon cancer, prostate cancer, choriocarcinoma, breast cancer, retinoblastoma, stomach carcinoma, acute myeloid leukemia, lymphoma, multiple myeloma, or leukemia. In one embodiment, the combination therapy or the single therapy may be used to treat hepatoma. In one embodiment, the combination therapy or the single therapy may be used to treat colorectal cancer. In one embodiment, the combination therapy or the single therapy may be used to treat tumors with high PD-L1 expression, which are suitable for anti-PD-1/L1 therapy and tumors with high tumor mutation burdens (TMB). In one embodiment, the combination therapy or the single therapy may be used to treat a cancer selected from the group of cancer that are currently approved for anti-PD-1/L1 therapy. In certain embodiments, combination therapy or the single therapy may be used to treat a cancer selected from pancreatic cancer, adenoid cystic carcinoma, lung cancer, gastrointestinal stromal tumor, and breast cancer. In certain embodiments, the cancer is locally advanced or metastatic solid tumor or lymphoma. In certain embodiments, the subject is treatment-experienced and shows disease progression. "Treatment-experienced" as used herein means that the subject has been treated with an anti-cancer therapy. Disease progression can be characterized by a sign of reduced responsiveness to the previous treatment, for example, increase in tumor size, increase in tumor cell number, or tumor growth.

However, treatment using combination therapies or the single therapy of the invention is not limited to the foregoing types of cancers. Examples of cancers amenable to treatment with the combination therapies include, but are not limited to, for example, glioma, glioblastoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, skin cancer, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. In one embodiment, a MDM2 inhibitor (e.g., APG-115) may be used in combination with an immune checkpoint modulator to treat or prevent various types of skin cancer (e.g., Squamous cell Carcinoma or Basal Cell Carcinoma), pancreatic cancer, breast cancer, prostate cancer, liver cancer, or bone cancer. In one embodiment, the combination therapy including a MDM2 inhibitor (e.g., APG-115) is used for treatment of a skin oncological disorder including, but not limited to, squamous cell carcinomas (including SCCIS (in situ) and more aggressive squamous cell carcinomas), basal cell carcinomas (including superficial, nodular and infiltrating basal cell carcinomas), melanomas, or actinic keratosis.

In some embodiments, the combination therapy is for treating patients suffering from unresectable or metastatic melanoma. In some embodiments, the combination therapy is for treating patients who is refractory or relapse of PD-1 therapy. In some embodiments, the combination therapy is for treating patients suffering from unresectable or metastatic melanoma who is refractory or relapse of PD-1 therapy. In some embodiments, the combination therapy is for treating the patient who is resistant to anti-PD-1 therapy.

In some embodiments, this disclosure provides a method for treating hyper-progression in a patient receiving anti-PD-1/PD-L1 therapy for the treatment of cancer, wherein the method comprises administering to the patient in need thereof a therapeutically effective amount of a MDM2 inhibitor, wherein a MDM2 inhibitor, such as APG-115, or a pharmaceutically acceptable salt thereof, wherein the cancer is melanoma, unresectable or metastatic melanomas, advance solid tumors comprising lung, renal, colorectal, head and neck, breast, brain, cervical, endometrial, and other cancers.

In certain embodiments, the effect that the combination therapy including a MDM2 inhibitor (e.g., APG-115) may have on cancer cells may depend, in part, on the various states of metabolic and oxidative flux exhibited by the cancer cells. The MDM2 inhibitor (e.g., APG-115) may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the development of a cancer cell. In some embodiments, the interaction of a MDM2 inhibitor (e.g., APG-115) with glycolytic and oxidative flux factors may enhance the ability of a MDM2 inhibitor (e.g., APG-115) to exert its restorative apoptotic effect in cancer.

In one embodiment, administration of a MDM2 inhibitor (e.g., APG-115) and the immune checkpoint modulator as described herein results in one or more of, reducing tumor size, weight or volume, increasing time to progression, inhibiting tumor growth and/or prolonging the survival time of a subject having an oncological disorder. In certain embodiments, administration of a MDM2 inhibitor (e.g., APG-115) and the immune checkpoint modulator reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject that is administered a MDM2 inhibitor (e.g., APG-115) alone or the immune checkpoint modulator alone. In certain embodiments, administration of a MDM2 inhibitor (e.g., APG-115) and the immune checkpoint modulator reduces tumor size, weight or volume, increases time to progression, inhibits tumor growth and/or prolongs the survival time of a population of subjects afflicted with an oncological disorder by at least 1%, 2%, 3%, 4%, 5%, 10%, 20%, 30%, 40%, 50%, 60%, 70%, 80%, 90%, 100%, 200%, 300%, 400% or 500% relative to a corresponding population of control subjects afflicted with the oncological disorder that is administered a MDM2 inhibitor (e.g., APG-115) alone or the immune checkpoint modulator alone. In other embodiments, administration of a MDM2 inhibitor (e.g., APG-115) and the immune checkpoint modulator stabilizes the oncological disorder in a subject with a progressive oncological disorder prior to treatment.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

EXEMPLIFICATION

While we have described a number of embodiments of this invention, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

| ABBREVIATIONS AND SPECIALIST TERMS | |
|---|---|
| bid | Twice a day |
| biw | Twice a week |
| BW | Body weight |
| BWL | Body weight loss |
| CR | Complete (tumor) regression (i.e., tumors become impalpable after treatment) |
| DMA | N,N-Dimethylaniline |
| FSC | Forward Scatter |
| h, hr, hrs | Hour(s) |
| HPMC | Hydroxypropyl methyl cellulose |
| HP-β-CD | Hydroxypropyl-β-Cyclodextrin |
| IDO1 | Indoleamine 2,3-Dioxygenase 1 |
| i.p. | Intraperitoneal injection |
| MDM2 | Mouse double minute 2 homolog |
| Mean ± SD | Mean ± standard deviation |
| Mean ± SEM | Mean ± Standard error mean |
| MDSC | Myeloid-derived suppressor cell |
| mg/kg | Milligram per kilogram |
| MSD | Meso Scale Discovery |
| n | Number |
| PK | Pharmacokinetic/Pharmacokinetics |
| PO or p.o. | Oral administration |
| PBS | Phosphate buffer saline |
| PR | Partial (tumor) regression (i.e., tumor volumes become smaller compared to before treatment) |
| PD-1 | programmed death 1 |
| PD-L1 | programmed death-ligand 1 |
| qd | Once a day |
| q2d | Once every two days |
| QOD | Every other day |
| Response rate | % of responsive animals in each treatment group, including CR, PR and SD |
| RTV | Relative Tumor Volume (RTV = $V_t/V_1$; $V_1$ and $V_t$ are the average tumor volumes on the first day of treatment (day 1) and the average tumor volumes on a certain time point (day T) |
| SD | Stable disease |
| SEM | Standard error of mean |
| SPF | Specific-pathogen-free |
| SPSS | Statistical Product and Service Solutions |
| Synergy score/ratio | Synergy score = ((A/C) × (B/C))/(AB/C); A = response to treatment A; B = response to treatment B; C = response to vehicle control; AB = combination of treatment A and B. |
| T/C (%) | T/C (%) = ($T_{RTV}/C_{RTV}$) × 100%; $T_{RTV}$ is RTV of the treatment group and $C_{RTV}$ is RTV of the control group. |
| TIL | Tumor infiltrating lymphocyte |
| TV | Tumor volume |
| W, WK or wk | Week |

Chemical Reagents and Materials

HPMC was purchased from Sigma-Aldrich (St. Louis, MO). Phosphate buffered solution (PBS) was purchased from Genom Biotech (Hangzhou, China). HP-β-CD was purchased from Seebio Biotech (Shanghai, China). DMA was purchased from Sigma-Aldrich (St. Louis, MO). Reagents, including manufacturers, catalog numbers and/or distributors used in the TIL analysis study were summarized in Table 1.

TABLE 1

Reagents used in analysis of TIL study

| Reagents | Manufacturer | Catalog number | Lot number | Distributor |
|---|---|---|---|---|
| Collagenase, type IV | Sigma | C5138 | 057M4030V | Merck |
| Hyaluronidase, Type V | Sigma | H6254 | SLBT4776 | Merck |
| DNase 1 | Sigma | D5025 | SLBV6757 | Merck |
| MACS Buffer | Miltenyi | 130-091-221 | 5160704558 | Fcmacs Biotech |

TABLE 1-continued

Reagents used in analysis of TIL study

| Reagents | Manufacturer | Catalog number | Lot number | Distributor |
|---|---|---|---|---|
| ACK lysis buffer | Life technology | A1049201 | 1902192 | Thermofisher |
| FcR Blocking Reagent, mouse | Miltenyi | 130-092-575 | 5171120429 | Fcmacs Biotech |
| Cytofix/cytoperm with golgistop kit | BD | 554715 | 7193740 | Fcmacs Biotech |
| Brilliant Stain Buffer | BD | 563794 | 6274713 | Fcmacs Biotech |
| CD4-BV605 | BD | 563151 | 7167854 | Fcmacs Biotech |
| CD4-PE-Cy7 | BD | 552775 | 7159622 | Fcmacs Biotech |
| CD25-BV421 | BD | 564370 | 717941 | Fcmacs Biotech |
| PD-1-APC | BD | 562671 | 7020605 | Fcmacs Biotech |
| PD-L1 BV711 | BD | 563369 | 7265615 | Fcmacs Biotech |
| Gr-1-BV605 | Biolend | 108439 | B219337 | Fcmacs Biotech |
| CD44-AF700 | BD | 560567 | 7146632 | Fcmacs Biotech |
| CD3-FITC | Thermofisher | 11-0032-82 | 4320569 | Thermofisher |
| CD8-PerCP-Cy5.5 | Thermofisher | 45-0081-82 | 4291993 | Thermofisher |
| Live/dead NIR | Thermofisher | L34976 | 1917885 | Thermofisher |
| CD62L-PE-Cy7 | Thermofisher | 25-0621-82 | 4277103 | Thermofisher |
| CD25-BV421 | BD | 564370 | 717941 | Fcmacs Biotech |
| CD45-e506 | Thermofisher | 69-0451-82 | 4306080 | Thermofisher |
| CD4-BV605 | BD | 563151 | 7167854 | Thermofisher |
| MHCII-FITC | Thermofisher | 11-5321-82 | 4322171 | Thermofisher |
| F4/80-APC | Thermofisher | 17-4801-82 | 4306323 | Thermofisher |
| CD3-AF700 | Thermofisher | 56-0032-82 | 4336536 | Thermofisher |
| CD206-PE | Thermofisher | 12-2061-82 | 1919876 | Thermofisher |
| CD4-PE-Cy7 | BD | 552775 | 7159622 | Fcmacs Biotech |
| CD11b-e450 | Thermofisher | 48-0112-82 | 4329941 | Thermofisher |
| CD11b-PerCP-Cy5.5 | Thermofisher | 45-0112-82 | 1929457 | Thermofisher |
| CD11c-PE | Thermofisher | 12-0114-82 | 4302534 | Thermofisher |
| B220-PE-Cy7 | Thermofisher | 25-0452-82 | 4317673 | Thermofisher |
| CD49b-e450 | Thermofisher | 48-5971-82 | 1946509 | Thermofisher |

Cell Culture

MH-22A murine hepatoma cells and MC38 colon cancer cells were maintained in vitro as a suspension culture in DMEM medium or RPMI1640 medium supplemented with 10% fetal bovine serum, 100 U/mL penicillin and 100 μg/mL streptomycin, and L-glutamine (2 mM) at 37° C. in an atmosphere of 5% $CO_2$ in air. The tumor cells were routinely passaged twice weekly. The cells growing in an exponential growth phase were harvested and counted for tumor inoculation.

Formulation

Formulations of test articles were prepared as detailed in Table 2. The formulations were used within 3 days under appropriate storage conditions.

TABLE 2

The dosing material preparation

| Compounds (Manufacturer) | Preparation | Concentration (mg/mL) | Storage |
|---|---|---|---|
| APG-115 Vehicle | 0.2% HPMC | — | 4° C. |
| epacadostat Vehicle | 10.31% HP-β-CD | — | 4° C. |
| APG-115 | Grinded appropriate amount of APG-115 in 0.2% HPMC solution. Then bring to final volume. The resulting mixture was suspension, light-shielded. Mixed well before dosing. | 1 | 4° C. |
| APG-115 | Grinded appropriate amount of APG-115 in 0.2% HPMC solution. Then bring to final volume. The resulting mixture was suspension, light-shielded. Mixed well before dosing. | 5 | 4° C. |
| Epacadostat (Selleck Chemicals) | Weight out appropriate amount of epacadostat in the brown bottle, add 3% DMA, stirring to make a solution. Then add 97% epacadostat vehicle to make a solution. | 10 | 4° C. |
| Anti-PD-1 (BioXcell) | Dilute 1.810 mL anti-PD-1 stock solution (6.63 mg/ml) with 10.190 mL PBS to make 1 mg/mL dosing solution | 1 | 4° C. |
| Anti-PD-1 (BioXcell) | Dilute 0.339 mL anti-PD-1 stock solution with 4.161 mL PBS to make 0.5 mg/mL dosing solution | 0.5 | 4° C. |
| Anti-PD-1 Isotype control (BioXcell) | Dilute 0.094 mL isotype control stock solution (7.96 mg/ml) with 1.406 mL PBS to make 0.5 mg/mL dosing solution | 0.5 | 4° C. |
| Anti-CD4 (BioXcell) | Dilute 0.426 mL anti-CD4 stock solution (7.05 mg/ml) with 1.974 mL PBS to make 1.25 mg/mL dosing solution | 1.25 | 4° C. |
| Anti-CD8 (BioXcell) | Dilute 0.427 mL anti-CD8 stock solution (7.03 mg/ml) with 1.973 mL PBS to make 1.25 mg/mL dosing solution | 1.25 | 4° C. |

TABLE 2-continued

The dosing material preparation

| Compounds (Manufacturer) | Preparation | Concentration (mg/mL) | Storage |
| --- | --- | --- | --- |
| Anti-CD4/Anti-CD8 Isotype control(BioXcell) | Dilute 0.1020 mL isotype control stock solution (7.35 mg/ml) with 1.398 mL PBS to make 0.5 mg/mL dosing solution | 0.5 | 4° C. |

Formulation was homogenous immediately before use by gently turning the tube up and down.

Observations and Data Collection

After tumor cell inoculation, the animals were checked daily for morbidity and mortality. At the time of routine monitoring, the animals were checked for any effects of tumor growth and treatments on normal behavior such as mobility, visual estimation of food and water consumption, body weight gain/loss (body weights were measured twice weekly), eye/hair matting and any other abnormal effect. Death and observed clinical signs were recorded on the basis of the numbers of animals within each subset. The entire procedures of dosing as well as tumor and body weight measurement were conducted in a Laminar Flow Cabinet.

Tumor volumes were measured twice weekly in two dimensions using a caliper, and the volume was expressed in $mm^3$ using the formula:

$$\text{Tumor Volume}(mm^3) = 0.5 a \times b^2$$

where a and b are the long and short diameters of the tumor, respectively.

Relative tumor volume (RTV) was calculated using the following formula:

$$RTV = V_t / V_1$$

Where $V_1$ and $V_t$ are the average tumor volumes on the first day of treatment (day 1) and the average tumor volumes on a certain time point (day t).

Synergy score was calculated using the following formula (Clarke R, Breast Cancer Research & Treatment, 1997, 46(2-3):255-278):

$$\text{Synergy score} = ((A/C) \times (B/C))/(AB/C);$$

A: response to treatment A; B: response to treatment B; C: response to vehicle control; AB: combination of treatment A and B.

Standard NCI procedures were used to calculate tumor parameters. Percent tumor growth inhibition (% T/C) was calculated as the mean RTV of treated tumors (T) divided by the mean RTV of control tumors (C)×100%. The percentage T/C value is an indication of antitumor effectiveness: a value of T/C<42% is considered significant antitumor activity by the NCI. A T/C value <10% is considered to indicate highly significant antitumor activity, and is the level used by the NCI to justify a clinical trial if toxicity and certain other requirements are met (termed DN-2 level activity). A body weight loss nadir (mean of group) of greater than 20%, or greater than 20% of drug deaths are considered to indicate an excessively toxic dosage.

Flow Cytometry

The live/dead fixable dye (Invitrogen) was used to exclude dead cells. The FOXP3 kit from eBioscience was used for FOXP3 staining. Cells were washed and stained for 30 min on ice with indicated antibodies in MACS buffer or Brilliant staining buffer. Samples were than analyzed on Life Technology Attune NxT flow cytometer.

PK Analysis

The quantitative LC/MS/MS analysis was conducted using an Exion HPLC system (AB Sciex, Ontario, Canada) coupled to an API 5500 mass spectrometer (AB Sciex, Ontario, Canada) equipped with an API electrospray ionization (ESI) source. The Phenomenex Titank phenyl-Hexyl column (50 mm×2.1 mm, 5 μm particle size) was used to achieved HPLC separation. The injection volume was 2 μl and the flow rate was kept constantly at 0.5 ml/min. Chromatography was performed with mobile phase A, acetonitrile:water:formic (5:95:0.1, by volume) and B, acetonitrile:water:formic (95:5:0.1, by volume). The mass spectrometer was operated at ESI positive ion mode for APG-115 while ESI negative mode for epacadostat. The detection of the ions was performed in the multiple reaction monitoring (MRM) mode, monitoring the transition of m/z 642.0→246.1 and 271.1→172.0 for APG-115 and IS (tolbutamide) in positive mode, 435.9→338.8 and 269.2→169.2 for epacadostat and IS (tolbutamide) in negative mode, respectively. Compounds parameters, declustering potential (DP), collision energy (CE) were 51, 61 V, 80, 18 V for APG-115 and IS in positive mode, −61, −15 V and −90, −23.5 V for epacadostat and IS in negative mode, respectively.

Data Analysis

Tumor growth curves were plotted with the observation time on the X-axis, and corresponding tumor volume (geometric mean) on the Y-axis. One-way ANOVA was performed to compare the tumor volume among groups, and when a significant F—statistics (a ratio of treatment variance to the error variance) was obtained, comparisons between groups were carried out with Games-Howell test. All data were analyzed in SPSS (Statistical Product and Service Solutions) version 18.0 (IBM, Armonk, NY, U.S.). Prism version 6 (GraphPad Software Inc., San Diego, CA) was used for graphic presentation. Life technology Attune Nxt flow cytometer was used for analyzing the TIL. Data acquisition and quantitation of PK were performed using Analyst Software version 1.6.3 (AB Sciex, Ontario, Canada).

Compliance

The protocol and any amendment (s) or procedures involving the care and use of animals in this study were reviewed and approved by the Institutional Animal Care and Use Committee (IACUC) of GenePharma prior to conduct. During the study, the care and use of animals was conducted in accordance with the regulations of the Association for Assessment and Accreditation of Laboratory Animal Care (AAALAC).

Example 1: Immunomodulatory Effects of APG-115 In Vitro 1.1 Activation of $CD4^+$ T Cells by APG-115

MDM2 inhibitor APG-115 was prepared using the one or more procedures described in U.S. Pat. No. 9,745,314, and Aguilar et al. *J. Med. Chem.* 2017(60) 2819-2839.

Effector T cells play a critical role in antitumor immunity. To investigate whether APG-115 influenced T cell function, CD4+ T cells isolated from mouse spleens were exposed to APG-115 or solvent control DMSO. Under the treatment with 250 nM of APG-115, caspase 3 cleavage was not detected in T cells, indicating that APG-115 did not induce T cell apoptosis. Notably, the treatment with 250 nM of APG-115 led to a rapid increase in CD25$^{high}$CD62L$^{low}$ cell populations, and increase in cell size of stimulated CD4+ T cells, implicating for T cell activation (FIG. 1).

Specifically, CD4+ T cells were positively selected from mouse spleens using magnetic beads and stimulated with 5 μg/ml plate-bound anti-CD3 and 2 μg/ml anti-CD28 in the presence of APG-115 (250 nM) or DMSO for 24 h (Day 1) or 48 h (Day 2). The percentages of CD25-expressing and CD62L-expressing populations (top panel), and FSC (lower panel) were determined by flow cytometry.

1.2 Induction of Cytokine Production in Stimulated Mouse T Cells by APG-115

The effect of APG-115 on cytokine production in stimulated mouse splenocytes was investigated. Mouse splenocytes freshly isolated from mice were stimulated with 5 μg/ml plate-bound anti-CD3 and 2 μg/ml anti-CD28 in the presence of APG-115 (250 nM) or DMSO for 24 h. After the treatment, supernatants were collected from the cell cultures and then cytokines were measured by MSD V-PLEX kit which enabled to test 10 cytokines. The expression levels of additional cytokines, i.e., IL-1β, IL-5, KC/GRO, IL-12p70, were below detection limit.

Figure 2:
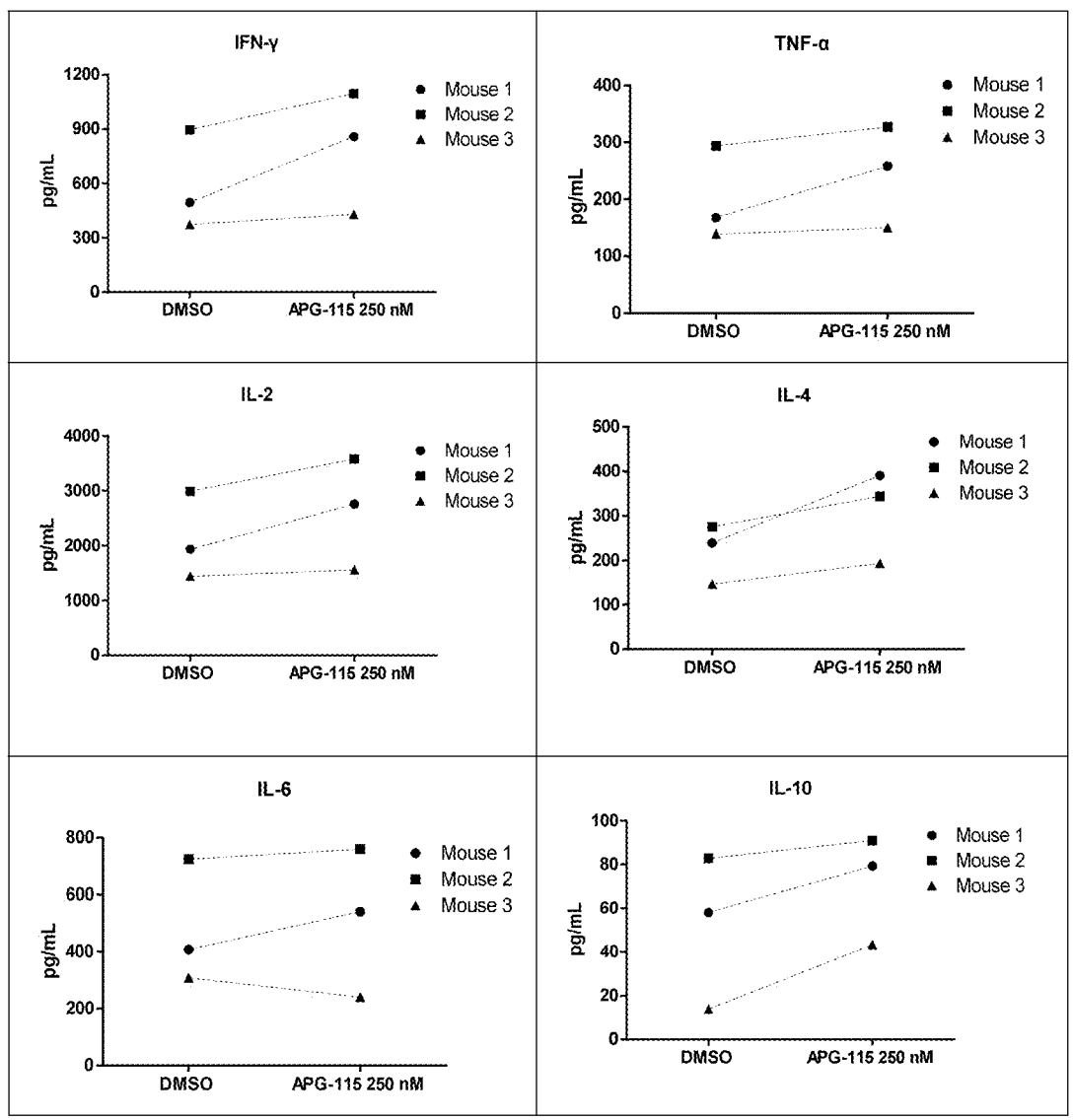
FIG. 2 shows that APG-115 increased cytokines production in stimulated mouse T cells.

The treatment with 250 nM of APG-115 caused upregulation of inflammatory cytokines in stimulated mouse T cells, including IFN-γ, IL-2, TNF-α, IL-10 and IL-4 (FIG. 2). The results indicate that a general activation enhancing effect of APG-115 on T cells. These cytokines may contribute to successful immune-mediated cancer eradication.

1.3 Upregulation of PD-L1 Expression on Tumor Cells by APG-115

Transcription factor p53 is involved in the regulation of PD-L1 expression (Cortez M A, 2015), which might serve as an indicator of the efficacy of anti-PD-1/PD-L1 treatment. Besides the effects on T cells, how APG-115 effects PD-L1 expression on MH-22A tumor cells was also investigated in vitro.

MH-22A cells were treated with indicated doses of APG-115 for 72 h. The expression levels of MDM2, p53, total STAT3 (t-STAT3), phosphorylated STAT3 (p-STAT3), PD-L1, and β-actin (loading control) expression were determined by Western blotting. PD-L1 expression levels which were reflected by fluorescence intensity were determined by flow cytometry.

The results demonstrated that, after the treatment with APG-115, the expression of TP53 and pSTAT3 proteins were upregulated in a dose-dependent manner (FIGS. 3A and 3B). Flow cytometry analysis further revealed that the treatment of tumor cells with APG-115 resulted in a dose-dependent increase in the surface expression of PD-L1. The data suggest that the induction of PD-L1-expressing tumor cells by APG-115 may make the tumor cells more vulnerable to the treatment with anti-PD-1 therapy.

Example 2: Enhanced Antitumor Activity of PD-1 Blockade by APG-115 in Trp53 Wild-Type MH-22A Syngeneic Model 2.1 In Vivo Efficacy Study in MH-22A Model Each mouse was inoculated subcutaneously at the right flank region with MH-22A tumor cells (5×10$^6$) in 0.2 mL of PBS for tumor development. The treatments were initiated when the mean tumor size reached ~65 mm$^3$. The test articles were administered to the tumor-bearing mice according to the regimen shown in the experimental design Table 3. The day of start dosing was defined as d1.

TABLE 3

Study design of efficacy study in MH-22A model

| Group | Animals | Treatment | Dose (mg/kg) | Dosing Route | Schedule |
|---|---|---|---|---|---|
| 1 | 10 | APG-115 vehicle | 0 | p.o. | qd × 16 d |
| 2 | 10 | APG-115 | 10 | p.o. | qd × 16 d |
| 3 | 10 | APG-115 | 50 | p.o. | qd × 16 d |
| 4 | 10 | Anti-PD-1 | 10 | i.p. | biw × 21 d |
| 5 | 10 | epacadostat | 100 | p.o. | bid × 16 d |
| 6 | 10 | APG-115 | 10 | p.o. | qd × 21 d |
|   |   | Anti-PD-1 | 10 | i.p. | biw × 21 d |
| 7 | 10 | APG-115 | 50 | p.o. | qd × 21 d |
|   |   | Anti-PD-1 | 10 | i.p. | biw × 21 d |
| 8 | 10 | epacadostat | 100 | p.o. | bid × 21 d |
|   |   | Anti-PD-1 | 10 | i.p. | biw × 21 d |

Note:
Dosing volume: 10 ul/g

Blood and tumor samples were collected from 5 mice/group in group-1, group-2, group-3 and group-5 4 hrs after the final dose on d16. Blood samples were collected from 5 mice/group in group-4, group-6, group-7 and group-8 4 hrs after the final dose on d29. Approximately 100 μl blood were collected in EDTA-2K tube and 50 μl plasma were collected for PK analysis. All samples were stored at −80° C. until analysis.

In this study, epacadostat (an IDO1 inhibitor) was included for a comparison reason because it has been proven to be a strong immune modulator in preclinical studies; however, its mechanism of action is completely different from APG-115.

Figure 4:
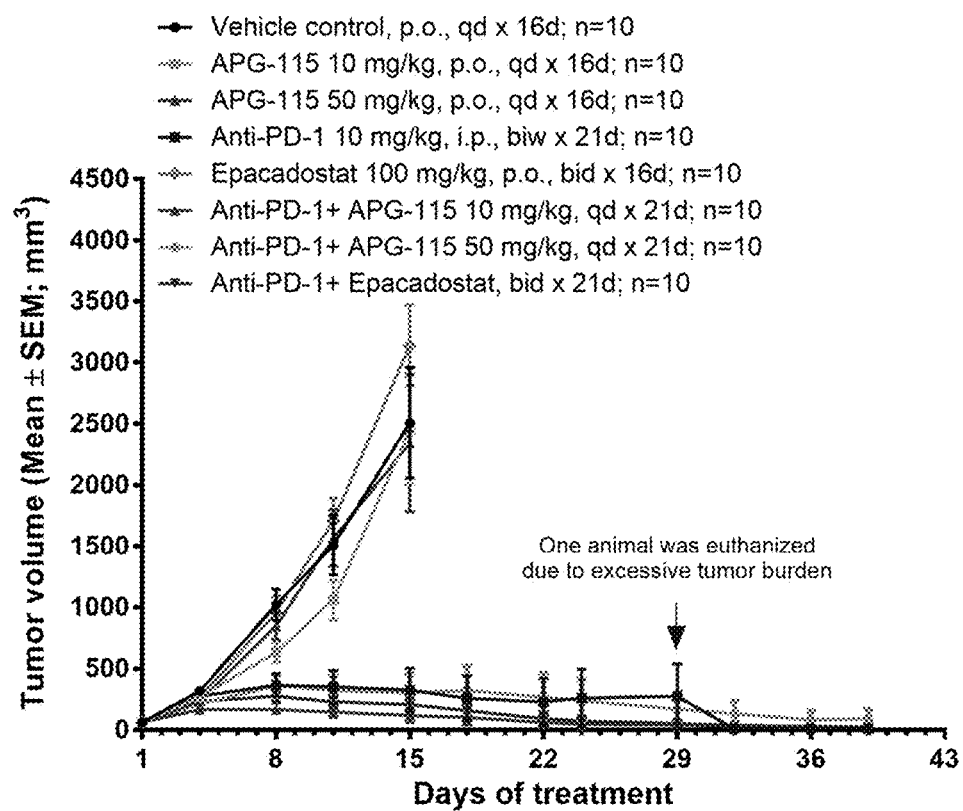
FIG. 4 demonstrates enhanced antitumor activity of anti-PD-1 therapy by combination with APG-115 in a syngeneic tumor model derived from MH-22A mouse hepatoma cells.

As shown in FIG. 4 and Table 4, treatment with the epacadostat or APG-115 as single agents did not exert antitumor activity. Treatment with anti-PD-1 alone at 10 mg/kg showed significant antitumor activity, with a T/C value of 13% (p<0.05 vs. vehicle) on d15. Combination treatment with anti-PD-1 and APG-115 at 10 mg/kg or 50 mg/kg exhibited greater antitumor activity, resulting in T/C values of 5% (P<0.01 vs. vehicle; P<0.001 vs. APG-115) and 12% (P<0.05 vs. vehicle; P<0.01 vs. APG-115), respectively on day 15. Combination treatment with anti-PD-1 and epacadostat at 100 mg/kg also produced significant antitumor activity, with a T/C value of 8% (p<0.01 vs. vehicle).

Mice in vehicle, APG-115 10 mg/kg and 50 mg/kg and epacadostat single agent groups were euthanized at d15 due to oversized tumors. On d29, one animal carrying an oversized tumor in the anti-PD-1 group was also terminated, leading to a sharp reduction of the average tumor volume in this group.

In FIG. 4, tumor growth curves were presented as mean±SEM of tumor volumes at various time points (n=10). Anti-PD-1 antibody at 10 mg/kg was administered intraperitoneally (i.p.) twice a week (biw) for 3 weeks (wk). APG-115 was administered orally (p.o.) on daily (qd) basis for 14 or 21 days. Mice in vehicle, epacadostat, and two APG-115 treatment groups were euthanized on day 15 because the average tumor volume reached humane endpoint. One animal that did not respond to the treatment with anti-PD-1 single agent and carried an oversized tumor was terminated on d29, resulting in a sharp reduction of the average tumor volume.

Figure 5:
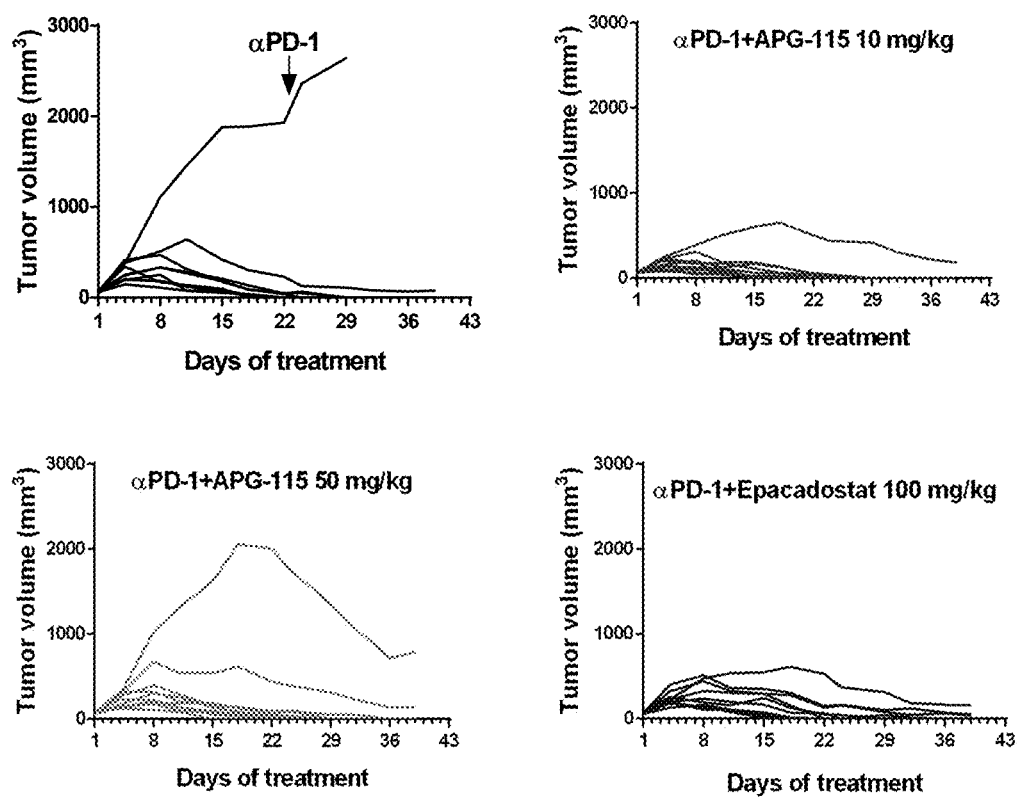
FIG. 5 illustrates tumor growth curves of individual animals treated with the indicated agents in the confirmation experiment.

Tumor growth curves of individual animals in anti-PD-1 alone and combination groups were illustrated in FIG. 5. Consistent with the experiment described early, 1 out of 10 tumors in anti-PD-1 single agent treatment group failed to respond to the treatment and showed as a progressive disease (indicated by an arrow). However, in the combination treatment groups, APG-115 or epacadostat was able to sensitize the resistant tumor as evidenced by the tumor growth inhibition in all treated animals.

Figure 6:
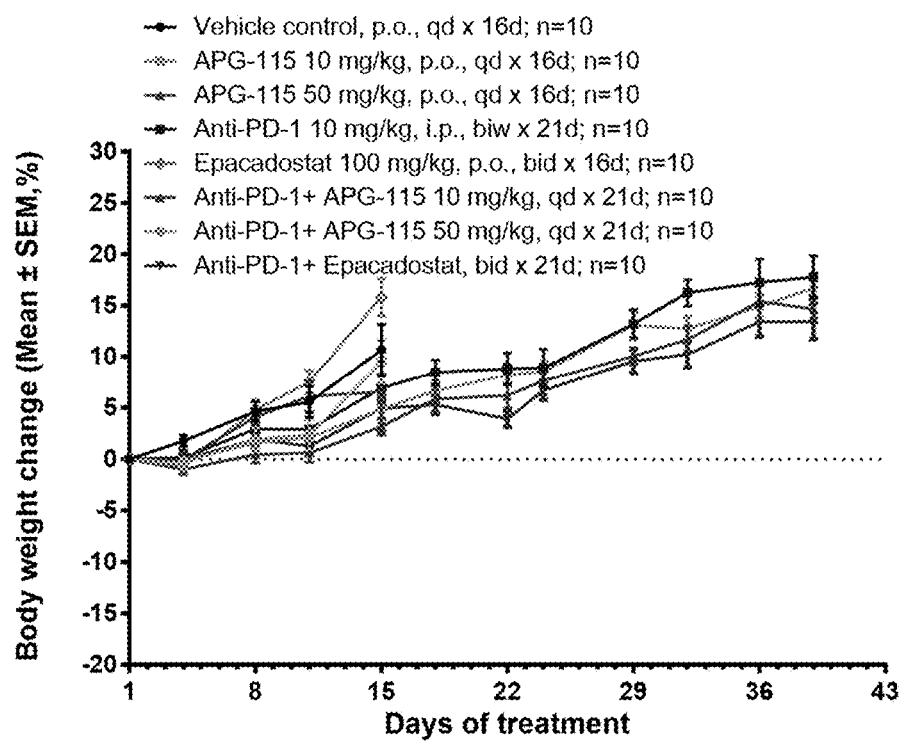
FIG. 6 illustrates body weight change (%) of experimental animals bearing MH-22A murine liver cancer syngeneic model under the treatment with APG-115 in combination with anti-PD-1.

As shown in Table 4, on d15, while 1 out of 10 animals (response rate, 10%) exhibited PR in anti-PD-1 single arm, 1 CR and 5 PR (60%) were achieved in the combination with 10 mg/kg of APG-115, 1 CR and 1 PR (20%) in the combination with 50 mg/kg of APG-115, and 3 PR (30%) in the combination with epacadostat. On d22, 5 CR and 3 PR (80%) were observed in anti-PD-1 single arm, 7 CR and 2 PR (90%) in the combination with 10 mg/kg of APG-115, 2 CR and 5 PR (70%) in the combination with 50 mg/kg of APG-115, and 5 CR and 1 PR (60%) in the combination with epacadostat. At the end point (d39), 8 CR (80%) were observed in anti-PD-1 single arm, 9 CR (90%) in the combination with 10 mg/kg of APG-115, 8 CR (80%) in the combination with 50 mg/kg of APG-115, and 7 CR and 2 PR (90%) in the combination with epacadostat. No body weight loss was observed under all treatments (FIG. 6).

Collectively, compared with anti-PD-1 single agent and the combination with epacadostat, the combination with APG-115 achieved an early on-set of CR and more CR responders. Additionally, like epacadostat, APG-115 was able to sensitize the resistant tumors.

inoculating MH-22A cells subcutaneously. Mice in re-challenge study were re-inoculated subcutaneously at the left upper flank with MH-22A tumor cells ($5 \times 10^6$/mouse) in 0.2 mL PBS for tumor development. No treatments were given after cell re-inoculation.

TABLE 5

Study Design of re-challenge study

| Group | N | Mice |
|---|---|---|
| 1 | 5 | Naïve mice |
| 2 | 5 | Anti-PD-1 treatment for 3 weeks and dosing suspension for 3 weeks from group-4 in Example 2.1 |
| 3 | 5 | APG-115 10 mg/kg + Anti-PD-1 treatment for 3 weeks and dose suspension for 3 weeks from group-6 in Example 2.1 |
| 4 | 5 | APG-115 50 mg/kg + Anti-PD-1 treatment for 3 weeks and dose suspension for 3 weeks from group-7 in Example 2.1 |
| 5 | 5 | epacadostat 100 mg/kg + Anti-PD-1 treatment for 3 weeks and dose suspension for 3 weeks from group-8 in Example 2.1 |

Figure 7:
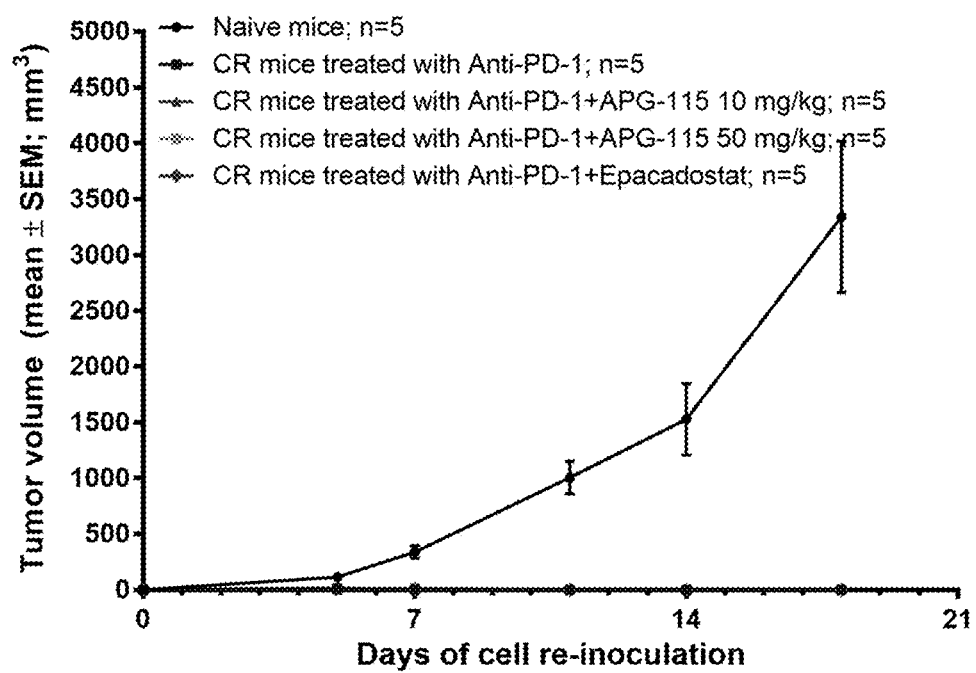
FIG. 7 illustrates tumor growth curves after re-challenge in pre-treated CR mice and naïve mice.

As shown in the FIG. 7, regrowth of syngeneic tumors in naive mice showed a fast growth kinetics, whereas the cured mice developed palpable tumors after cell inoculation and these small tumors regressed completely rapidly. By day 11, they became unmeasurable. These data confirmed that the CR responders treated with anti-PD-1, or the combinations with APG-115 or epacadostat developed antitumor immu-

TABLE 4

Efficacy of APG-115 in combination with anti-PD-1 antibody in MH-22A murine hepatoma syngeneic models in C3H mice

| Treatment | RTV (Mean ± SEM) d15 | T/C (%) d15 | Synergy score d15 | Response rate (%) d15 | Response rate (%) d22 | Response rate (%) d39 |
|---|---|---|---|---|---|---|
| Vehicle | 38.5 ± 7.0 | — | — | 0% | — | — |
| APG-115 10 mg/kg | 37.8 ± 6.8 | 98 | — | 0% | — | — |
| APG-115 50 mg/kg | 36.2 ± 8.7 | 94 | — | 0% | — | — |
| Anti-PD-1 10 mg/kg | 5.1 ± 2.8* | 13 | — | 10% (1/10 PR) | 80% (5/10 CR, 3/10 PR) | 80% (8/10 CR) 1/10 Euthanize |
| epacadostat 100 mg/kg | 49.1 ± 5.8 | 128 | — | 0% | — | — |
| Anti-PD-1 + APG-115 10 mg/kg | 1.9 ± 0.9**,### | 5 | 2.64 | 60% (1/10 CR, 5/10 PR) | 90% (7/10 CR, 2/10 PR) | 90% (9/10 CR) |
| Anti-PD-1 + APG-115 50 mg/kg | 4.5 ± 2.2*,## | 12 | 1.07 | 20% (1/10 CR, 1/10 PR) | 70% (2/10 CR, 5/10 PR) | 80% (8/10 CR) |
| Anti-PD-1 + epacadostat 100 mg/kg | 3.1 ± 0.8**,&&& | 8 | 2.10 | 30% (3/10 PR) | 60% (5/10 CR, 1/10 PR) | 90% (7/10 CR, 2/10 PR) |

*p < 0.05 vs. Vehicle Control;
**p < 0.01 vs. Vehicle Control;
p < 0.01 vs. APG-115;
p < 0.001 vs. APG-115;
&&&p < 0.001 vs. epacadostat.
Synergy scores: > 1 represents synergistic, = 1 represents additive, < 1 represents antagonistic.

2.2 Re-Challenge Study in MH-22A Model

Figure 8:
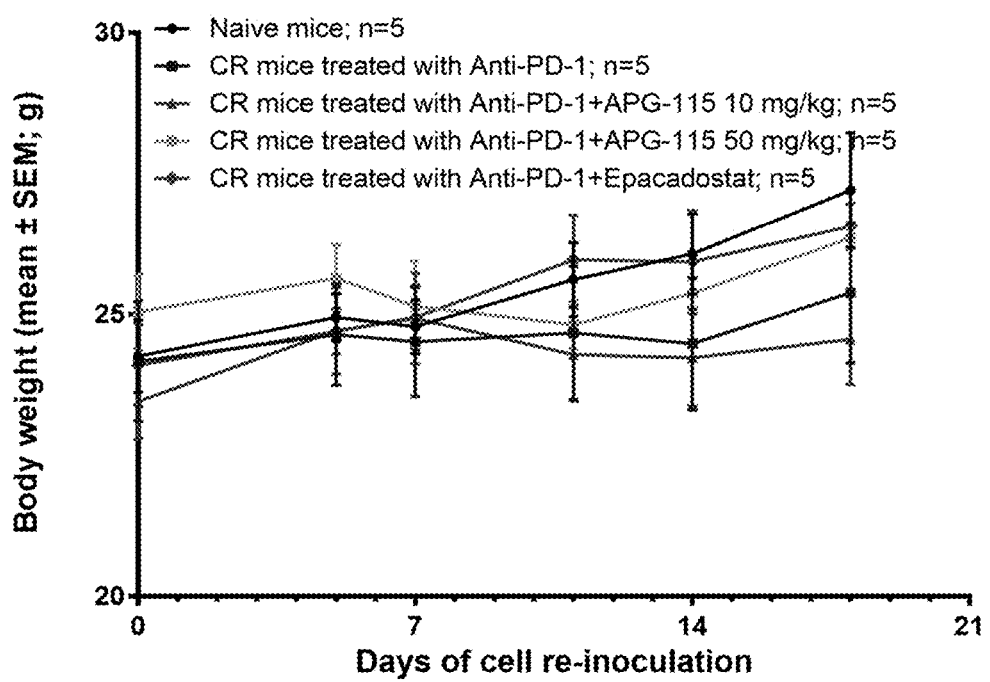
FIG. 8 illustrates body weight change (%) of mice in re-challenge study.

To further confirm the development of immune memory in treated animals, three weeks after the final dose, 5 cured mice (i.e., CR) randomly selected from each group of anti-PD-1, anti-PD-1 plus 10 mg/kg or 50 mg/kg of APG-115, anti-PD-1 plus epacadostat treatments, along with 5 naïve mice as controls (Table 5), were re-challenged by nity that enabled to eradicate re-engrafted tumor cells. No body weight loss was observed under all treatments (FIG. 8).

2.3 TIL Analysis in MH-22A Model

Each mouse was inoculated subcutaneously at the right flank region with MH-22A tumor cells ($5 \times 10^6$) in 0.2 mL of PBS for tumor development. The treatments were started when the mean tumor size reached 60 mm³. The test articles were administered to the tumor-bearing mice according to the regimen shown in the experimental design Table 6. The day of start dosing was defined as d1.

TABLE 6

Study design of TIL analysis

| Group | Animals | Treatment | Dose (mg/kg) | Dosing Route | Schedule |
|---|---|---|---|---|---|
| 1 | 5 | Isotype control | 5 | i.p. | biw × 6 d |
|   |   | APG-115 vehicle | 0 | p.o. | q2d × 6 d |
| 2 | 5 | APG-115 | 10 | p.o. | q2d × 6 d |
| 3 | 5 | Anti-PD-1 | 5 | i.p. | biw × 6 d |
| 4 | 5 | epacadostat | 100 | p.o. | bid × 6 d |
| 5 | 5 | Anti-PD-1 | 5 | i.p. | biw × 6 d |
|   |   | APG-115 | 10 | p.o. | q2d × 6 d |
| 6 | 5 | Anti-PD-1 | 5 | i.p. | biw × 6 d |
|   |   | epacadostat | 100 | p.o. | bid × 6 d |

Mice were euthanized on day 7, and tumors were mechanically dissociated and digested with Collagenase IV (Sigma), hyaluronic acid (Sigma) and DNase (Sigma). Single-cell suspensions were prepared and stained against the indicated markers for flow cytometry analysis. Tumor samples were collected 24 hrs post last dosing.

Mice bearing MH-22A murine hepatoma tumors were treated with various agent(s) under different regimens as indicated. Isotype control antibody was included in the control.

Figure 10:
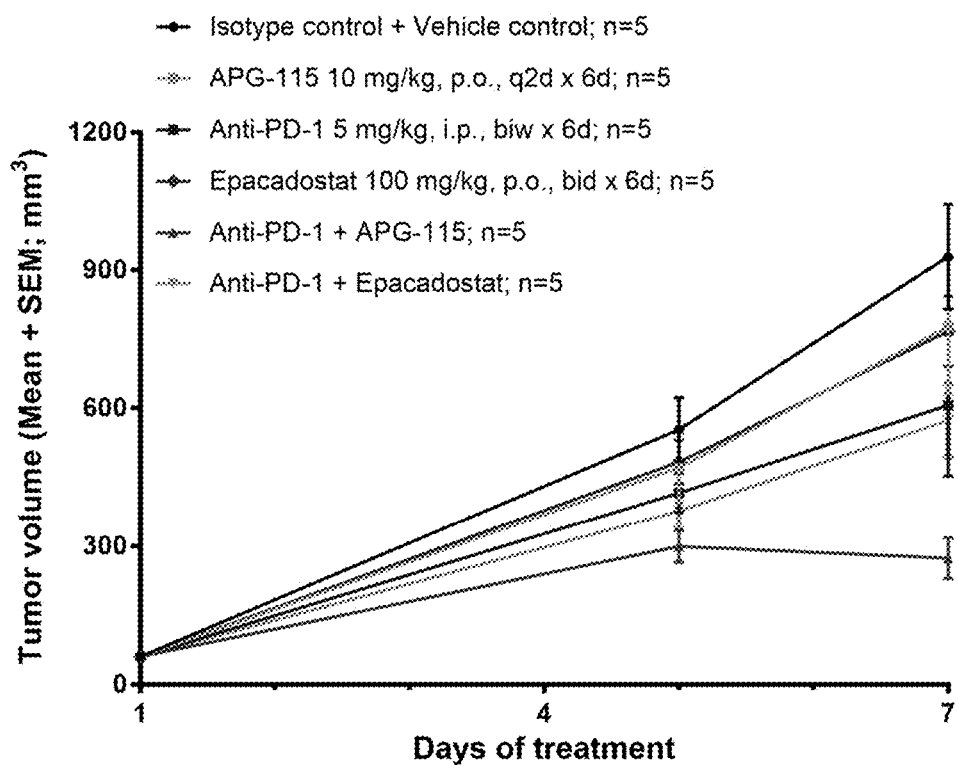
FIG. 10 illustrates tumor growth curves in the in vivo study designated for TIL analysis.
Figure 11:
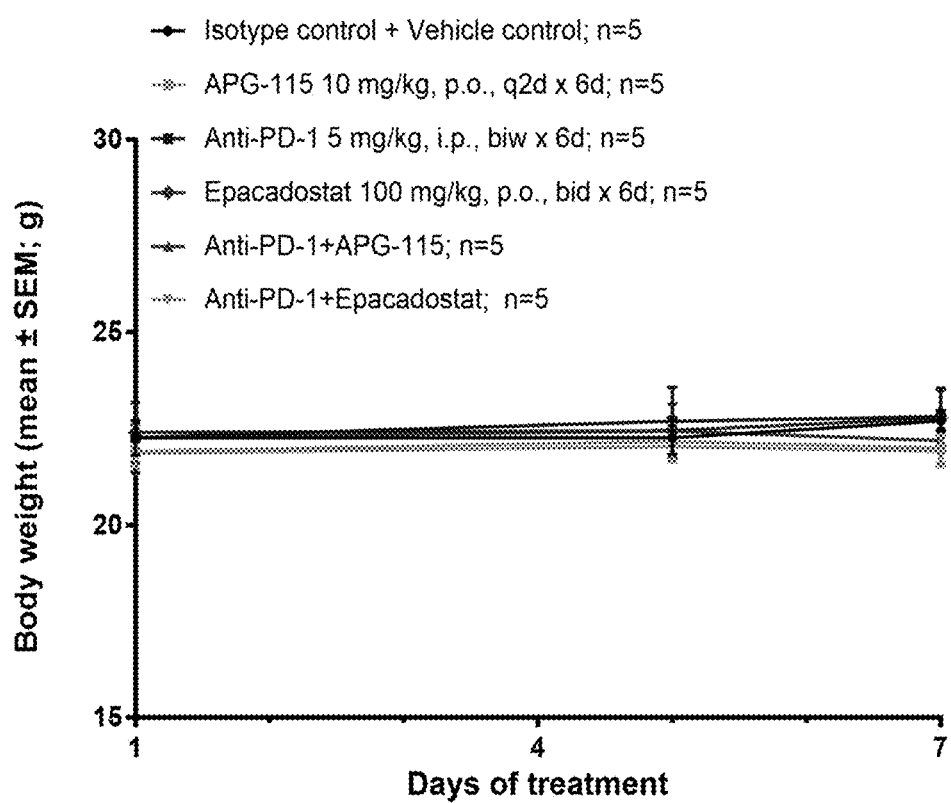
FIG. 11 illustrates body weight change (%) of experimental animals in TIL study.

As shown in FIG. 10 and Table 7, combination treatment with 10 mg/kg of APG-115 and 5 mg/kg of anti-PD-1 consistently exerted synergistic antitumor activity, leading to a T/C value of 29% (p<0.01 vs. control; synergy score, 1.8). In contrast, the combination treatment with epacadostat failed to exhibit such a synergistic effect after the short period of treatment. No body weight loss was observed under all treatments (FIG. 11).

TABLE 7

Efficacy of APG-115 in combination with anti-PD-1 in MH-22A syngeneic tumor model at d7

| Treatment | RTV (Mean ± SEM) | T/C (%) | Synergy score |
|---|---|---|---|
| Isotype control+ Vehicle | 15.5 ± 2.1 | — | — |
| APG-115 10 mg/kg | 12.8 ± 2.4 | 83 | — |
| Anti-PD-1 5 mg/kg | 10.1 ± 2.5 | 65 | — |
| epacadostat 100 mg/kg | 12.7 ± 1.2 | 82 | — |
| Anti-PD-1 + APG-115 | 4.6 ± 0.8**# | 29 | 1.8 |
| Anti-PD-1 + epacadostat | 9.7 ± 1.6 | 62 | 0.9 |

**p < 0.01 vs. Vehicle control;
p < 0.05 vs. APG-115;
Synergy scores: >1 represents synergistic, =1 represents additive, <1 represents antagonistic.

TIL Analysis by Flow Cytometry

On d7, when the mean tumor volume reached approximately 300-500 mm3, syngeneic tumors were collected and processed for TIL analysis. In p53 wt MH-22A syngeneic tumors, in comparison with the control, treatment with anti-PD-1 alone only slightly increased the frequency of CD45+ cells, CD3+ T cells, and cytotoxic CD8+ T cells (P>0.05, FIG. 12A), whereas the combined therapy exerted a more significant effect of increasing infiltration of these cells (p<0.01). There were approximately a 1.5 to 2-fold increase relative to the control. The frequency of M1 macrophages was significantly increased by either anti-PD-1 antibody or combined therapy in comparison with the control (P<0.01); however, no significant difference between these two treatments (P>0.05). Most strikingly, the frequency of M2 macrophages was reduced by the combined therapy in comparison with both control (P<0.01) and anti-PD-1 single agent groups (P<0.05).

Figure 12:
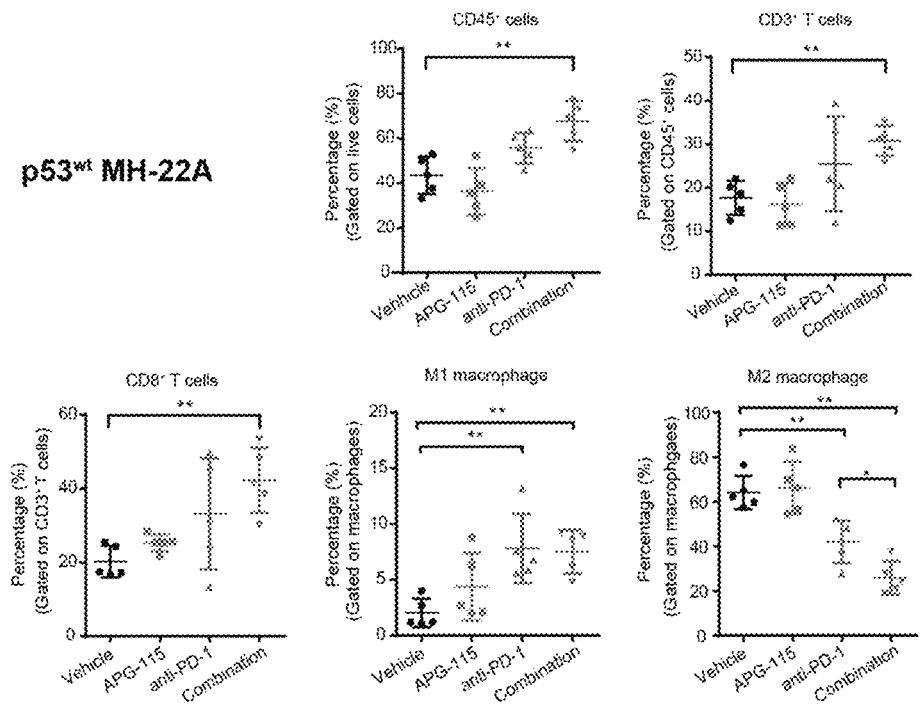
FIG. 12 shows substantial increases in tumor infiltrating CD45$^+$, CD3$^+$ and cytotoxic CD8$^+$ cell populations, as well as significantly decrease in M2 macrophages in syngeneic tumors after the combination treatment with APG-115 and anti-PD-1 antibody.
Figure 12:
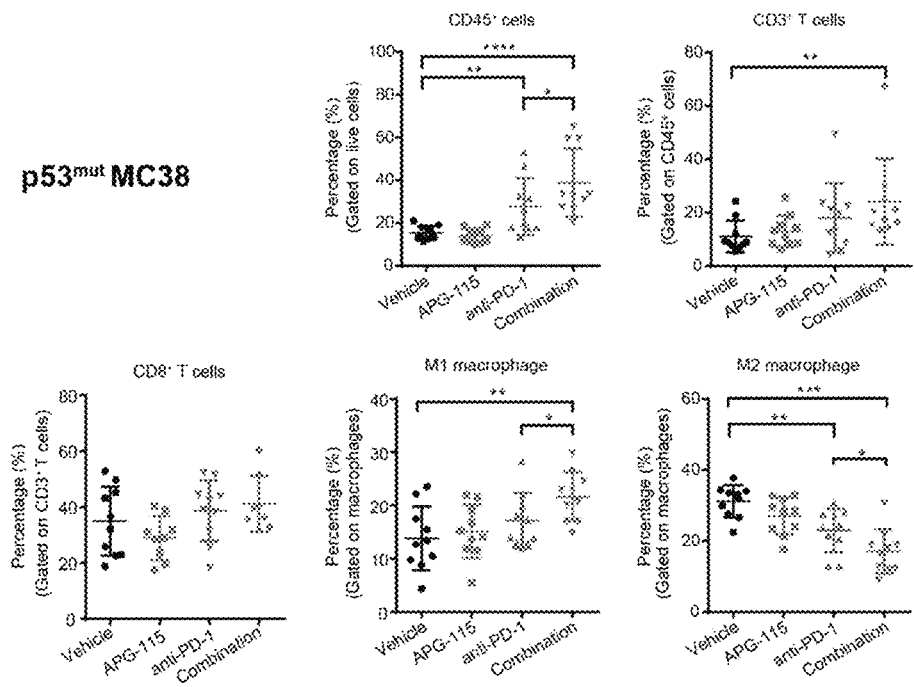
Figure 13:
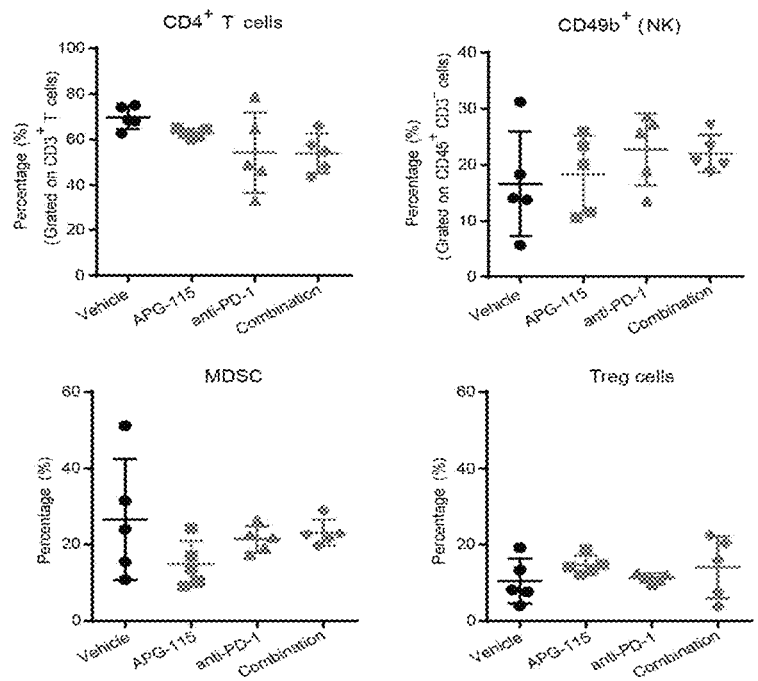
FIG. 13 shows no significant changes in the percentage of MDSC and Treg cells.
Figure 13:
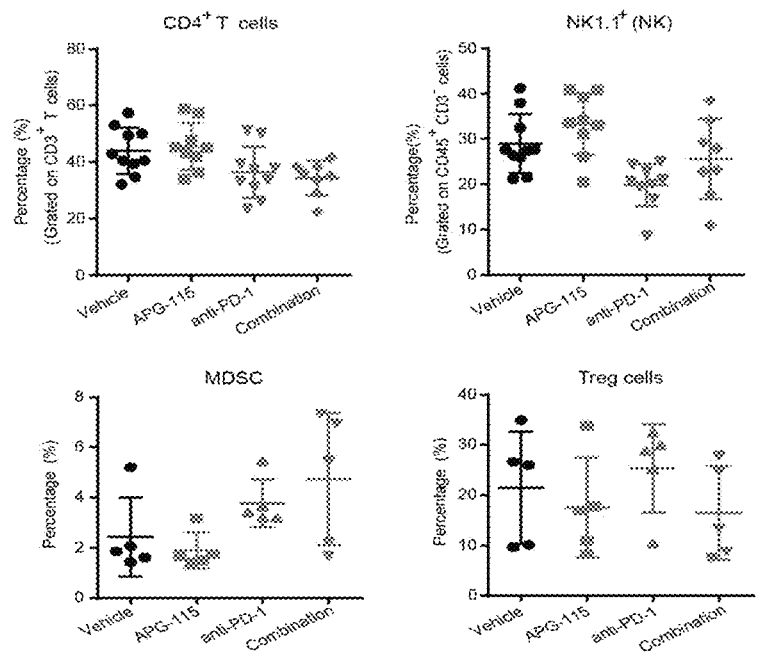

In p53mut MC38 tumors, in comparison with the control, treatment with anti-PD-1 alone slightly increased the frequency of CD3+ T cells, cytotoxic CD8+ T cells, and M1 macrophages compared with the control (P>0.05), whereas the frequency of CD45+ cells (P<0.001), CD3+ T cells (P<0.01), and M1 macrophages (P<0.01), but not CD8+ T cells (P>0.05), was significantly increased by the combined therapy (FIG. 12B). Importantly, the frequency of CD45+ cells and M1 macrophages was substantially increased by the combined therapy compared with anti-PD-1 single agent (P<0.05). In contrast, the frequency of M2 macrophages was remarkably reduced by the combined therapy compared with both control (P<0.001) and anti-PD-1 single agent groups (P<0.05). In both p53 wt MH-22A and p53mut MC38 syngeneic tumors, phenotype analysis of CD4+ T cells, NK cells, MDSCs, and regulatory T (Treg) cells showed no significant changes after treatment with APG-115, anti-PD-1 antibody, or the combination (FIG. 13).

2.4 T Cell Depletion Study in MH-22A Model

TIL analysis showed that there was a statistically significant increase of tumor infiltrating cytotoxic CD8+ T cells after the combination treatment with APG-115 and anti-PD-1. These results indicate that a robust effector T cell response is elicited with the combination treatment of APG-115 and anti-PD-1. To further elucidate the cellular mechanisms of action, the depletion of immune cells using specific CD4 or CD8 targeting antibodies was undertaken.

Each mouse was inoculated subcutaneously at the right flank region with MH-22A tumor cells (5×10$^6$) in 0.2 mL of PBS for tumor development. The treatments of anti-CD4 and anti-CD8 were started when the mean tumor size reached 60 mm$^3$. The combination treatments of APG-115 and anti-PD-1 were given one day later. The test articles were administered to the tumor-bearing mice according to the regimen shown in the experimental design Table 8. The day of start dosing was defined as d1.

TABLE 8

T cell depletion study design in MH-22A model

| Group | Animals | Treatment | Dose (mg/kg) | Dosing Route | Schedule |
|---|---|---|---|---|---|
| 1 | 8 | Isotype controls | 5 | i.p. | biw × 11 d |
|   |   | APG-115 vehicle | 0 | p.o. | q2d × 11 d |
| 2 | 8 | APG-115 | 10 | p.o. | q2d × 11 d |
|   |   | Anti-PD-1 | 5 | i.p. | biw × 11 d |
| 3 | 8 | APG-115 | 10 | p.o. | q2d × 11 d |
|   |   | Anti-PD-1 | 5 | i.p. | biw × 11 d |
|   |   | Anti-CD4 | 12.5 | i.p. | biw × 11 d |
| 4 | 8 | APG-115 | 10 | p.o. | q2d × 11 d |
|   |   | Anti-PD-1 | 5 | i.p. | biw × 11 d |
|   |   | Anti-CD8 | 12.5 | i.p. | biw × 11 d |

Figure 14:
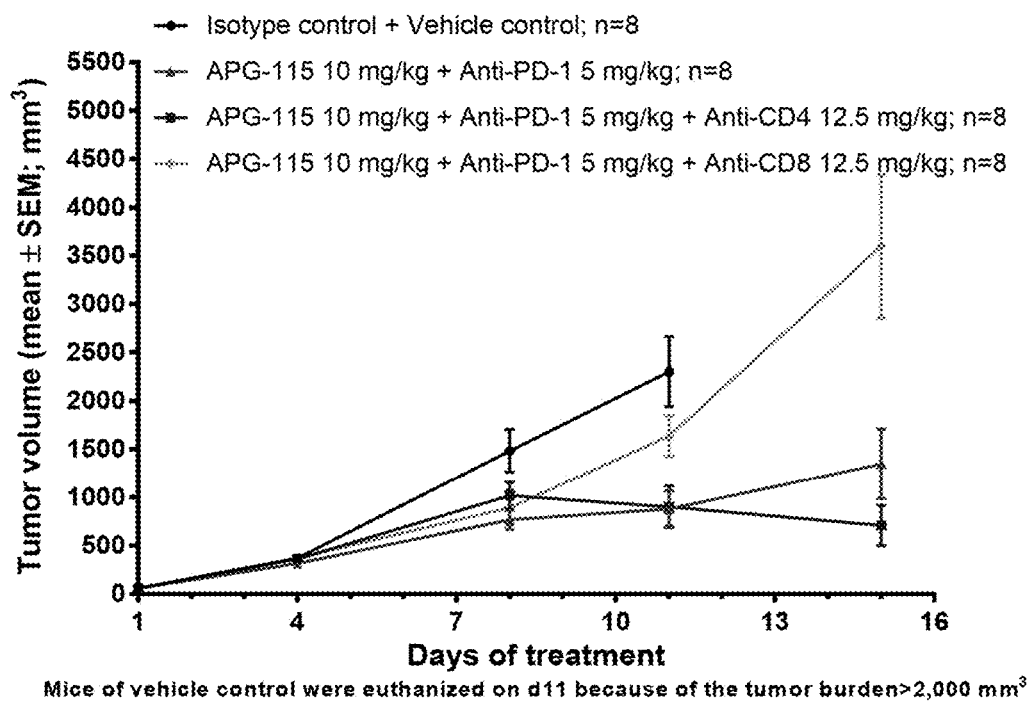
FIG. 14 demonstrates that CD8$^+$ T cells are required for synergy between APG-115 and anti-PD-1 for the treatment of MH-22A syngeneic liver tumor.
Figure 15:
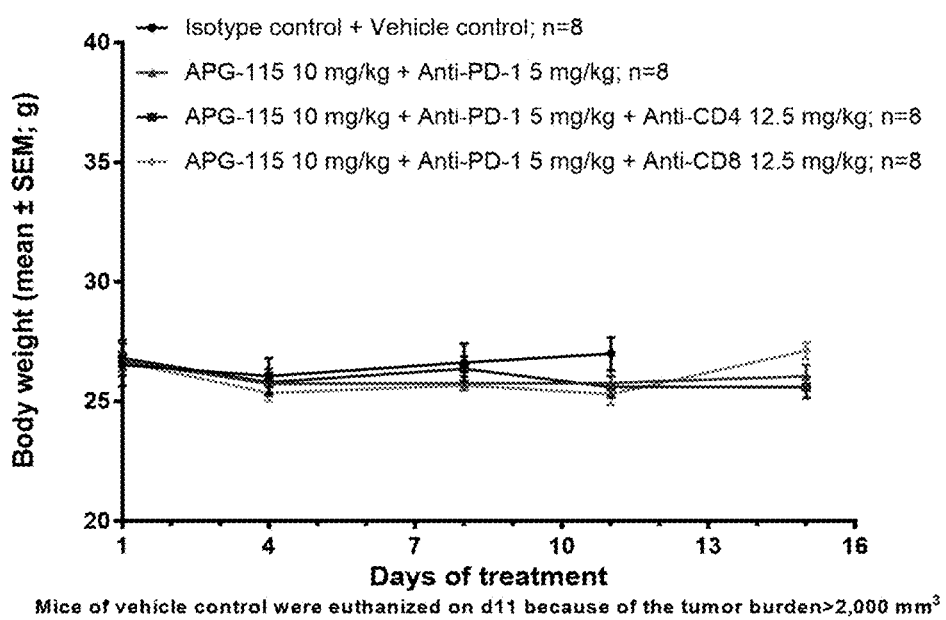
FIG. 15 illustrates body weight change (%) of experimental animals in T cell depletion study.

In this study, combination treatment with APG-115 and anti-PD-1 consistently showed potent anti-tumor activity, with a T/C value of 38% on d11 (p<0.05 vs. vehicle control group) and mean tumor volume of 1347 mm$^3$ on day 15 (FIG. 14 and Table 9). However, the therapeutic efficacy induced by the combination therapy was almost completely abrogated on depletion of CD8+ T cells. Interestingly, the depletion of CD4+ T cell resulted in a T/C value of 39% on d11 and mean TV of 709 mm$^3$ on d15 with the combination treatment of APG-115 and anti-PD-1 antibody. The results suggest that CD4+ T cells are not required for efficacy of the combined treatment. No body weight changes were observed under all treatment (FIG. 15).

In summary, these results suggest that cytotoxic CD8+ T cells, but not CD4+ T cells, are required for the enhance antitumor activity of the combination treatment with APG-115 and anti-PD-1 antibody.

TABLE 9

Efficacy of combination treatment with APG-115 and anti-PD-1 was blocked by CD8+ T cell depletion.

| Treatment | RTV@ D8 | T/C(%)@ D8 | RTV@D11 | T/C(%) @ D11 | Mean TV (mm³) on D15 (Mean ± SEM) |
|---|---|---|---|---|---|
| Isotype + Vehicle | 24.7 ± 3.6 | — | 38.3 ± 5.8 | — | — |
| APG-115 + Anti-PD-1 | 12.8 ± 1.7 | 52 | 14.7 ± 3.0** | 38 | 1347 ± 362 |
| APG-115 + Anti-PD-1 + Anti-CD4 | 17.0 ± 2.4 | 69 | 15.1 ± 3.7** | 39 | 709 ± 209 |
| APG-115 + Anti-PD-1 + Anti-CD8 | 15.0 ± 3.2* | 61 | 27.4 ± 3.6 | 71 | 3597 ± 744 |

*p < 0.05 vs. vehicle control group;
**p < 0.01 vs. vehicle control group 2.5 Pharmacokinetic (PK) Analysis In efficacy study of Example 2.1, mice in vehicle, APG-115 10 mg/kg and 50 mg/kg, and epacadostat single-agent groups were euthanized on d15 as described above. To assess PK characteristics of APG-115 and epacadostat in this study, plasma and tissue samples were collected 4 h after the last dosing on d15.

Figure 9:
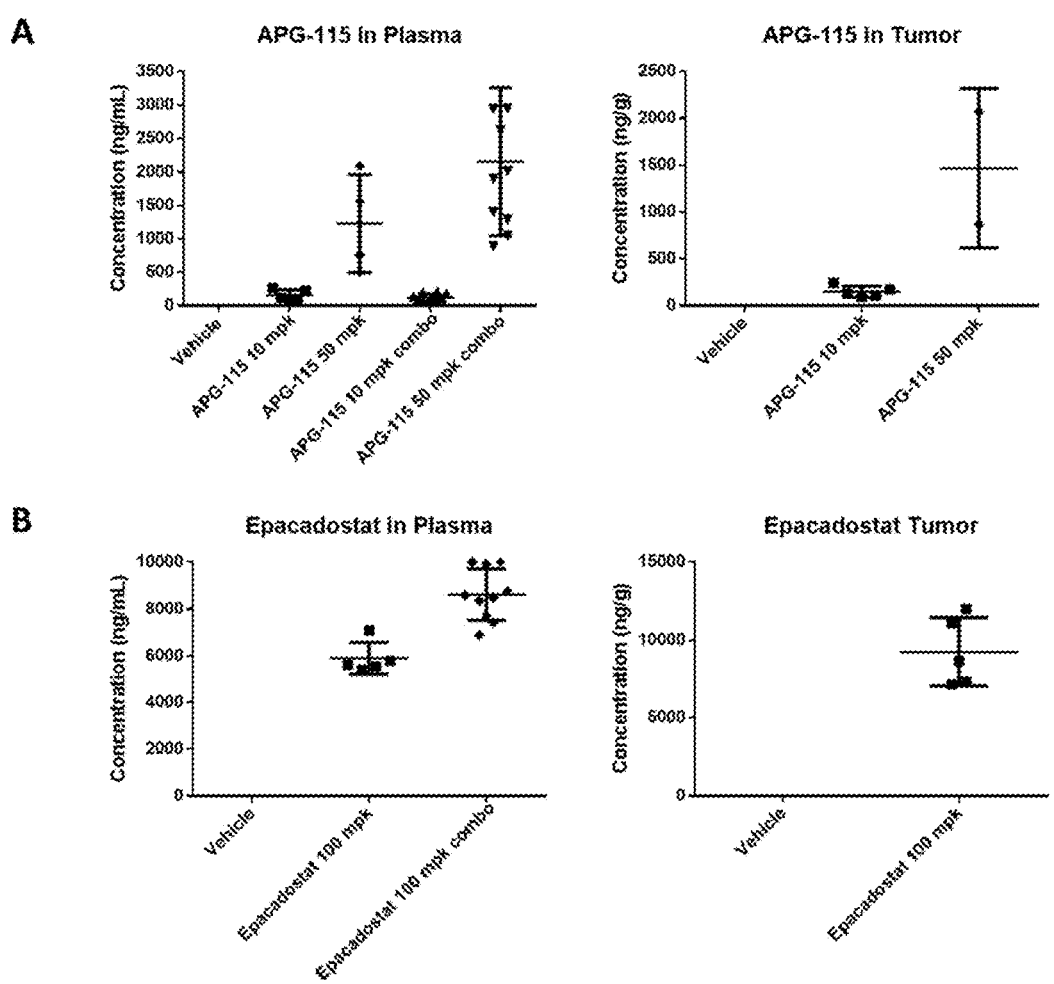
FIG. 9 illustrates exposure of APG-115 and epacadostat in plasma and tumor tissue.

As shown in FIG. 9, after daily, oral administration of APG-115 at 10 mg/kg, 50 mg/kg for 15 days, the plasma concentrations of APG-115 were 157.4 and 1228.0 ng/mL, respectively. The plasma concentration of APG-115 at 10 mg/kg or 50 mg/kg in combination with anti-PD-1 were 120.1 and 2152.4 ng/mL, respectively. Correspondingly, APG-115 concentrations in tumor tissues were 152.2 and 1469.0 ng/g, respectively, when dosed at 10 mg/kg or 50 mg/kg as single agent. In addition, after daily oral administration of epacadostat at 100 mg/kg alone or combine with anti-PD-1, the plasma of epacadostat were 5894.0 and 8619.0 ng/mL, respectively. Correspondingly, the epacadostat concentrations in tumor were 9256.0 ng/g at 100 mg/kg dosed alone. Overall, the results confirmed the appropriate systemic exposure and tissue distribution of APG-115 and epacadostat after dosing. The increases in systemic exposure and tissue distribution were approximately dose proportional. Furthermore, it appears that was no apparent pharmacokinetic interaction between anti-PD-1 antibody and APG-115 or epacadostat, erasing the concerns of drug-drug interaction.

Example 3: Enhanced Antitumor Activity of PD-1 Blockade by APG-115 in Trp53 Mutant MC38 Syngeneic Model 3.1 In Vivo Efficacy Study in MC38 Model Each mouse was inoculated subcutaneously at the right flank region with MC38 tumor cells (5×10⁵) in 0.1 mL of PBS for tumor development. The treatments were initiated when the mean tumor size reached ~63 mm³. The test articles were administered to the tumor-bearing mice according to the regimen shown in the experimental design Table 10. The day of start dosing was defined as d1.

TABLE 10

Study design of efficacy in MC38 model

| Group | Animals | Treatment | Dose (mg/kg) | Dosing Route | Schedule |
|---|---|---|---|---|---|
| 1 | 10 | Isotype control | 5 | i.p. | biw × 17 d |
|   |    | APG-115 vehicle | 0 | p.o. | q2d × 17 d |
| 2 | 10 | APG-115 | 10 | p.o. | q2d × 17 d |
| 3 | 10 | APG-115 | 50 | p.o. | q2d × 17 d |
| 4 | 10 | Anti-PD-1 | 5 | i.p. | biw × 17 d |
| 5 | 10 | APG-115 | 10 | p.o. | q2d × 17 d |
|   |    | Anti-PD-1 | 5 | i.p. | biw × 17 d |
| 6 | 10 | APG-115 | 50 | p.o. | q2d × 17 d |
|   |    | Anti-PD-1 | 5 | i.p. | biw × 17 d |

Efficacy of combination treatment with APG-115 plus anti-PD-1 antibody was further evaluated in a Trp53 mutant MC38 syngeneic mouse tumor model on a C57BL/6 background.

Figure 16:
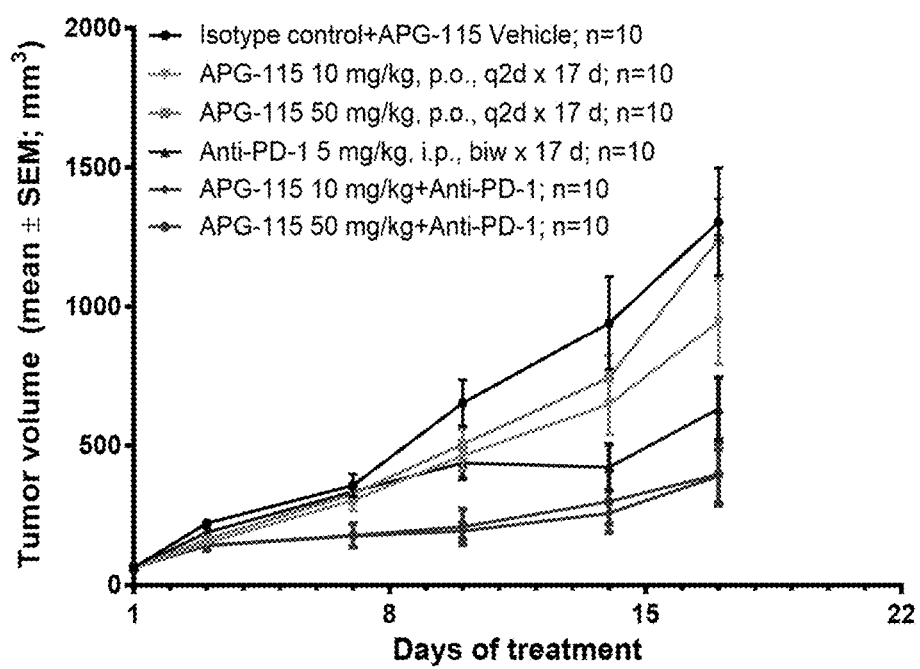
FIG. 16 demonstrates that APG-115 synergizes with anti-PD-1 therapy for the treatment of Trp53 mutant MC38 syngeneic mouse tumor. Tumor growth curves were presented as mean±SEM of tumor volumes at various time points (n=10). Anti-PD-1 antibody at 10 mg/kg was administered intraperitoneally (i.p.) twice a week (biw) for 17 days. APG-115 was administered orally (p.o.) once every two days (q2d) basis for 17 days.
Figure 17:
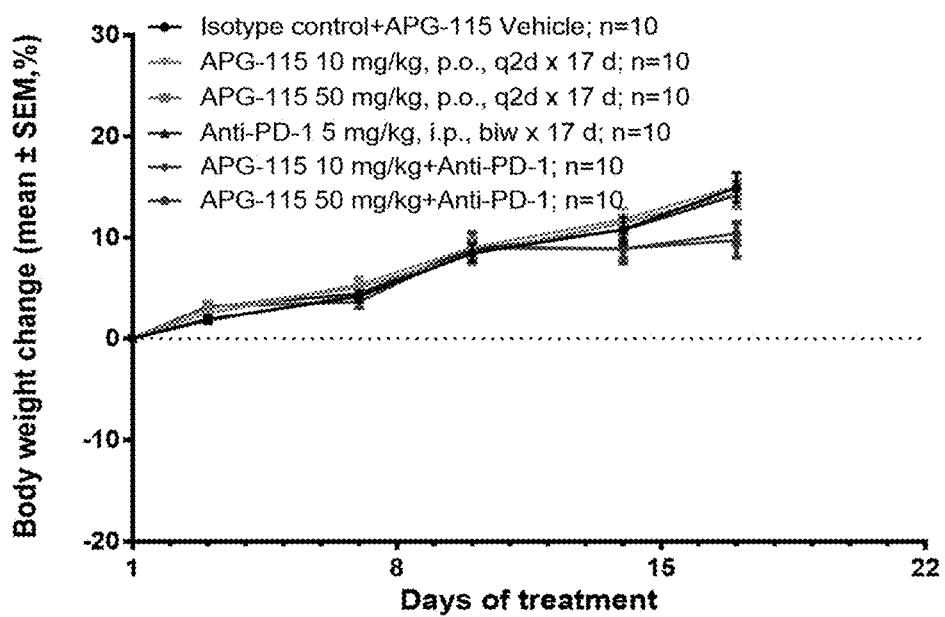
FIG. 17 illustrates body weight change (%) of experimental animals bearing MC38 murine colon cancer syngeneic model under the treatment with APG-115 in combination with anti-PD-1 antibody.

As shown in FIG. 16 and Table 11, treatment with APG-115 as single agent exerted minimal antitumor activity. Treatment with anti-PD-1 alone at 5 mg/kg exhibited antitumor activity, with a T/C value of 48% (P<0.01 vs. vehicle) on day 17. Combination treatment with anti-PD-1 and APG-115 at 10 mg/kg or 50 mg/kg exhibited greater antitumor activity, resulting in T/C values of 29% (P<0.001 vs. vehicle) and 31% (P<0.001 vs. vehicle; P<0.01 vs. APG-115), respectively on day 17. No body weight loss was observed under all treatments (FIG. 17).

TABLE 11

Efficacy of APG-115 in combination with anti-PD-1 antibody in Trp53 mutant MC38 syngeneic murine colon tumor in C57BL/6 mice

| Treatment | RTV (Mean ± SEM) d17 | T/C (%) d17 | Synergy score d17 |
|---|---|---|---|
| Vehicle | 21.0 ± 3.3 | — | — |
| APG-115 10 mg/kg | 15.3 ± 2.7 | 73 | — |
| APG-115 50 mg/kg | 19.8 ± 2.2 | 94 | — |
| Anti-PD-1 5 mg/kg | 10.1 ± 1.8** | 48 | — |
| Anti-PD-1+APG-115 10 mg/kg | 6.2 ± 1.5*** | 29 | 1.2 |
| Anti-PD-1+APG-115 50 mg/kg | 6.4 ± 1.9***## | 31 | 1.5 |

**p < 0.0 vs. Vehicle control;
***p < 0.001 vs. Vehicle control;
p < 0.01 vs. APG-115;
Synergy scores: >1 represents synergistic, =1 represents additive, <1 represents antagonistic.

The data provided herein demonstrate that a MDM2 inhibitor (e.g., APG-115) combining with PD-1 blockade exerts enhance antitumor activity in both wild-type and mutant Trp53 tumors. Besides its role in tumor targeting activity, the MDM2 inhibitor may function as an immune modulator to synergize with immunotherapy for cancers. Thus, the results support further clinical investigation of the synergy in human cancers, regardless of their p53 mutation status.

Example 4: The Combinatory Effect

Figure 18:
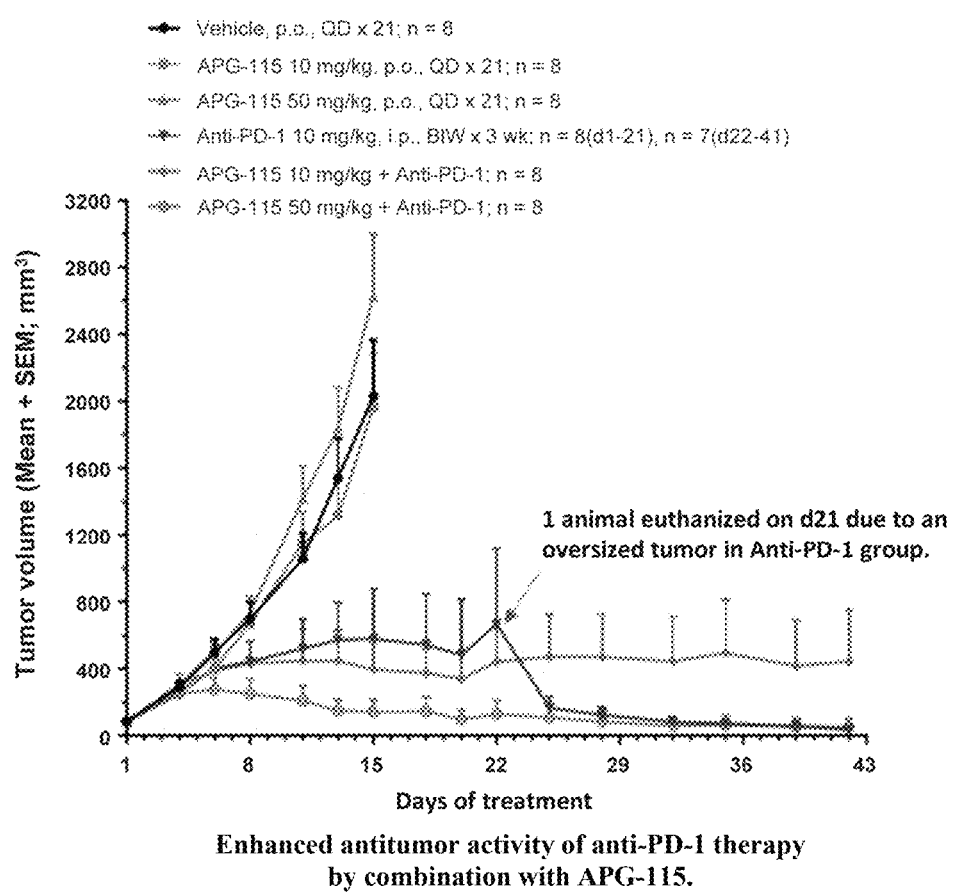
FIG. 18 illustrates enhanced antitumor activity of anti-PD-1 therapy by combination with APG-115.

The combinatory effect of the combination treatment with APG-115 plus anti-PD-1 therapy was explored extensively both in vitro and in vivo. In vitro studies revealed that APG-115 treatment enhanced murine CD4+ T cell activation and led to upregulation of inflammatory cytokines (including IFN-γ, IL-2, TNF-α, IL-10 and IL-4) in a syngeneic murine tumor model. The increased surface expression of PD-L1 on tumor cells was also detected after treatment of APG-115. In vivo efficacy studies demonstrated that, in a syngeneic model derived from MH22A murine hepatoma cells, while anti-PD-1 therapy substantially inhibited tumor growth and led to complete regression (CR) or partial regression (PR) in a large fraction of tumor bearing animals, the addition of APG-115 was able to expand CR fraction, accelerate the therapeutic effect and, importantly, convert the remaining non-responders into responders (FIG. 18).

Sequential re-challenge studies confirmed that CR mice treated with the combination therapy efficiently rejected re-engrafting of MH22A tumor cells, implicating for the successful development of immune memory.

Furthermore, tumor infiltrating lymphocyte (TIL) analysis revealed that CD45+ cells, CD3+ T cells, and CD8+ T cells were significantly increased after the combination therapy in comparison with anti-PD-1 monotherapy.

Pharmacokinetics (PK) analysis revealed that systemic exposure and tumor exposure of APG-115 was dose proportionally.

Mechanistically, in addition to the role of APG-115 in direct T cell activation, cytokine release in T cells and upregulation of PD-L1 expression in tumor cells, a substantial increase in tumor infiltrating cytotoxic CD8+ T cells and decrease in immune suppressive dendritic cells in the tumor microenvironment may play a crucial role in enhancement of antitumor activity in combination treatment.

Taken together, the preclinical data have demonstrated that APG-115 would act as an immune modulator in both P53 wild type and mutant P53 tumors, which provide a new approach for treatment of cancer patients who are either hyper-progression with, or relapse or refractory to anti-PD-1/PD-L1 monotherapy.

Example 5 APG-115 in Patients with Advanced Solid Tumors

Patients with advanced soft tissue sarcoma (STS), adenoid cystic carcinoma (ACC) or other solid tumors in China (CTR20170975) were treated with APG-115. In dose escalation, patients received APG-115 (100-200 mg) orally QOD for first 21 days of a 28-day cycle, until disease progression. Study objectives include safety (primary endpoint), pharmacokinetics (PK), pharmacodynamics (PD), and antitumor activity assessed every 8 weeks.

Result: 13 patients (8 STSs, 2 ACCs and 2 osteosarcoma) had been treated in 3 cohorts of APG-115 (100 mg, 150 mg, 200 mg). The median number of prior systemic anticancer therapies was 2 (range 0-4). The patients received a median of 2 cycles of APG-115 (range 0-3). DLT was observed in one patient during cycle 1 at 200 mg, included thrombocytopenia and febrile neutropenia. The most common AEs (reported in ≥10% of pts) included: anaemia, thrombocytopenia, vomiting, hypercholesterolaemia, and leukopenia. SAE occurred in 7 pts (54%). The most common Grade 3 or 4 TRAEs were anaemia (38.5%), thrombocytopenia (38.5%), leukopenia (30.8%), and neutropenia (23.1%). One partial response was observed in 1 liposarcoma patient with MDM2 amplification and TP53 wt at the 150 mg dose, 5 patients had SD as the best overall response. PK analysis indicated an approximately dose proportional increase in Cmax and AUC0-t following a single or multiple oral administration across dose levels from 100 to 200 mg, with median Tmax ranging from 4 to 6 hours. Preliminary pharmacodynamic results showed that serum MIC-1 levels were elevated from individual baseline starting from APG-115 doses ≥100 mg, suggesting a potential mechanistic PD relationship (p53 activation). As expected from mechanism of action, MIC-1 increase was exposure dependent within the dose range tested in pts with solid tumors.

Conclusions: APG-115 had activity in MDM2 amplification liposarcoma. The AE profiles were consistent with other drugs in the MDM2-targeting drug class.

Example 6: Clinical Study

An open label, multi-center two-part phase Ib/II study comprises two parts. Part 1 is the dose escalation of APG-115 in combination with the label dose of pembrolizumab. Part 2 is phase II design on APG-115 at recommended phase II dose (RP2D) in combination with pembrolizumab in the patients with PD1/PD-L1 refractory/relapse melanoma. In Part 1, a standard "3+3" design will be employed to determine the maximum tolerated dose (MTD) of APG-115 by assessing the dose limiting toxicity (DLT) of APG-115 in combination with pembrolizumab. Four dose levels of APG-115 will be tested: 50, 100, 150, and 200 mg. APG-115 will be administered orally every other day (QOD) for a consecutive 2 weeks (i.e. dosed at Day 1, 3, 5, 7, 9, 11, and 13), with one week dosing off as 3-weeks a cycle. Pembrolizumab (PD-1 blockade) is administrated following FDA approved label dose, i.e.: 200 mg intravenous infusion at Day 1 of every 3 weeks as a cycle. Dose and schedule of APG-115 may be modified depending on the toxicity. In Part 2, at RP2D of APG-115 in combination with pembrolizumab, approximately 43 patients will be treated with the combination until disease progression, unacceptable toxicity, or another discontinuation criteria is met. Safety, tolerability, and determination of the MTD and RP2D are primary objectives of Part 1; overall response rate is the primary objective of Part 2. PK, PD, other anti-tumor assessments, etc. are the secondary objectives. In part 2, Simon's two-stage design (Simon R (1989). Controlled Clinical Trials 10: 1-10.) will be used. The null hypothesis that the true response rate is 10% or lower will be tested against a one-sided alternative.

Inclusion Criteria:

Male or non-pregnant, non-lactating female patients age 18 years on day of signing the informed consent Part 1:
1. Histologically confirmed, unresectable or metastatic melanoma or advanced solid tumor patients who failed standard of care therapy;
2. ECOG PS 0-2
3. No CNS metastases Part 2:
1. Histologically confirmed, unresectable or metastatic melanoma, and refractory or relapse after PD1 antibody treatment and ineligible for other standard of care therapy;
2. ECOG PS 0-2;
3. Measurable disease according to irRECIST and RECIST 1.1, Lesions situated in a previously irradiated area, or an area subject to other loco-regional therapy (e.g. intralesional injections) should be considered non-measurable Life expectancy≥3 months Continuance of treatment related toxicities (except alopecia) due to prior radiotherapy or chemotherapy agents or biological therapy (including PD1/PDL1 antibodies) must-≤Grade 1 at the time of dosing.

Adequate bone marrow and organ function as indicated by: the following laboratory values without continuous supportive treatment (such as blood transfusion, coagulation factors and/or platelet infusion, red/white blood cell growth factor administration, or albumin infusion) as assessed by laboratory for eligibility QTc interval (mean of 3)≤450 ms in males, and ≤470 ms in females Left ventricular ejection fraction (LVEF)≥lower limit of institutional normal (LLN) as assessed by echocardiogram (ECHO) or multigated acquisition (MUGA) scan Exclusion Criteria:

Any prior systemic MDM2-p53 inhibitor treatment. Received chemotherapy within 21 days (42 days for nitrosoureas or mitomycin C) prior to first dose.

Prior loco-regional treatment with intralesional therapy (e.g. talimogene laherparepvec) for unresectable or metastatic melanoma in the last 6 months prior to start of study treatment.

Received hormonal and biologic (<1 half-lives), small molecule targeted therapies or other anti-cancer therapy within 21 days prior to first dose. Radiation or surgery within 14 days of study entry, thoracic radiation within 28 days prior to first dose.

Has known active central nervous (CNS) metastases and/or carcinomatous meningitis. Or has neurologic instability per clinical evaluation due to tumor involvement of the CNS.

Requirement for corticosteroid treatment, with the exception of megestrol, local use of steroid: i.e.: topical corticosteroids, inhaled corticosteroids for reactive airway disease, ophthalmic, intraarticular, and intranasal steroids.

Concurrent treatment with an investigational agent or device within 28 days prior to the first dose of therapy.

human plasma. Reversed-phase HPLC separation was achieved with an XBridge, C18, (50×2.1 mm, 3.5 micron). MS/MS detection was set at mass transitions of m/z 642.3→246.3 for APG-115 and m/z 647.4→246.1 for D5-APG-115 (IS) in TIS positive mode.

For Safety study of APG-115, the safety evaluation included vital signs, electrocardiogram (ECG) parameters, Easter Cooperative Oncology Group (ECOG) performance status data, clinical laboratory tests and adverse event data. Safety assessments were performed in each treatment cycle.

For Efficacy study of APG-115, patients with solid tumors will be evaluated for response every two cycles (i.e., 8 weeks), according to the current version of response evaluation criteria in solid tumors: revised RECIST Guideline, version 1.1 (Eisenhauer, 2009).

APG-115 is a second generation MDM2 inhibitor that can block the interaction of MDM2-p53, thus stabilizing the p53 protein and allowing it to resume its transcriptional regulation function for the cell cycle and apoptosis.

The primary objective of the study was to determine the safety and tolerability of APG-115, identify Dose Limiting Toxicity (DLT), maximum tolerated dose (MTD)/recommended phase II dose (RP2D). The secondary objective of the study was to determine the PK, PD, anti-tumor effects of APG-115.

Single dose escalation study was conducted. A standard "3+3" design was employed to determine the maximum tolerated dose (MTD) of APG-115 by assessing the dose limiting toxicity (DLT) of APG-115. Five dose levels of APG-115 was tested: 10, 20, 50, 100, 200, and 300 mg. APG-115 was administrated orally every other day (QOD) for a consecutive 3 weeks (i.e. dosed at Day 1, 3, 5, 7, 9, 11, 13, 15, 17, 19, and 21), with one week dosing off as 4-weeks a cycle. 3 patients were enrolled per dose level, and if no patient shows DLT, then 3 patients were enrolled at the next dose level. The scheme of the trial design is provided below.

Phase I dose escalation study-accelerated dose escalation, then standard "3+3" design:

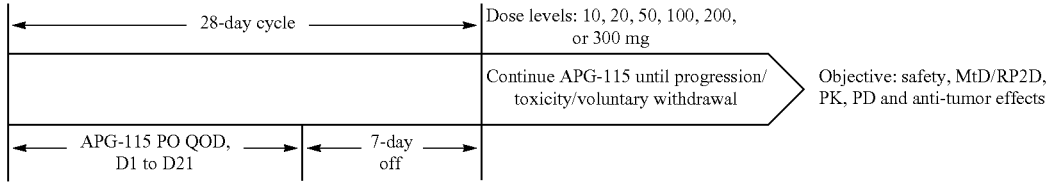

Example 7: A Phase I Study of a APG-115 in Patients with Advanced Solid Tumors

APG-115 is a potent and orally active small-molecule MDM2 protein inhibitor. Binding to MDM2 protein, APG-115 restores p53 tumor suppressive function via induction of apoptosis in tumor cells retaining wild-type p53. In addition, enhanced antitumor activity was demonstrated in the syngeneic tumor models after APG-115 combined with PD-1 blockade.

This Phase I study (APG-115-US-001) was designed to assess safety, toxicity, pharmacokinetics (PK), pharmacodynamics (PD), and antitumor activity of APG-115 orally in patients with advanced solid tumors in US (NCT02935907).

For PK study of APG-115, APG-115 in K$_2$EDTA human plasma was determined using an LC/MS/MS method using D5-APG-115 as the internal standard (IS). APG-115 and the IS were extracted using protein precipitation extraction from Inclusion Criteria for Patient Enrollment are:
1. Age 18 years;
2. (ECOG) Performance Status 1;
3. Adequate hematologic or bone marrow, renal and liver functions
4. Confirmed locally advanced or metastatic solid tumors or lymphoma who have disease progression after treatment with available therapies that are known to confer clinical benefit Exclusion Criteria for Patient Enrollment are:
1. Receiving concurrent anti-cancer therapy; or any investigational therapy within 14 days prior to the first dose of study drug;
2. Use of therapeutic doses of anti-coagulants is excluded, along with anti-platelet agents;
3. Neurologic instability per clinical evaluation due to tumor involvement of the central nervous system (CNS);

4. Uncontrolled concurrent illness.

Baseline characteristics of pateints are shown in Tables 12(a) and 12(b)

TABLE 12

Patient demographics and characteristics at baseline

Table 12 (a)

| Characteristic, n (%) | APG-115 (N = 29) |
|---|---|
| Age, median (range) | 64.0(36; 87) |
| Male sex | 17(58.6) |
| ECOG PS | |
| 0 | 9 |
| 1 | 20 |
| Prior systemic cancer therapies (0-15) | |
| 0 | 3 |
| 2-5 | 20 |
| ≥6 | 6 |

TABLE 12-continued

Patient demographics and characteristics at baseline

Table 12 (b)

| Primary Cancer, n (%) | APG-115 (N = 29) |
|---|---|
| Adenoid Cystic Carcinoma | 2 (6.8%) |
| Ampulla Of adenocarcinoma | 1 (3.4%) |
| Breast Cancer | 2 (6.9%) |
| Colon Cancer | 3 (10.3%) |
| Esophageal Squamous Cell Carcinoma | 1 (3.4%) |
| Gastrointestinal Stromal Tumor | 1 (3.4%) |
| Intrahepatic Cholangiocarcinoma | 1 (3.4%) |
| Leiomyosarcoma | 1 (3.4%) |
| Liposarcoma | 2 (6.9%) |
| Lung cancer | 5 (17.2%) |
| Ovarian Cancer | 4(13.8%) |
| Pancreatic Cancer | 2 (6.9%) |
| Prostate Cancer | 2 (6.9%) |
| Rectaladenocarcinoma | 1 (3.4%) |
| Osteosarcoma | 1 (3.4%) |

The safety study results are shown in Tables 12 (c) and 12(d). Till Apr. 19, 2019, total 29 patients were treated with APG-115 at various doses (10-300 mg). APG-115 was well tolerated and had manageable adverse events. Most common TRAEs (>10%): fatigue, nausea, vomiting, decreased appetite, diarrhea, neutrophil count decreased, platelet count decreased, white blood cell count decreased. Platelet count decreased, fatigue, and nausea were determined as DLTs.

TABLE 12 c

| Patient disposition (by dose level) | 10 mg (n = 1) | 20 mg (n = 1) | 50 mg (n = 1) | 100 mg (n = 15) | 200 mg (n = 6) | 300 mg (n = 5) | ALL (n = 29) |
|---|---|---|---|---|---|---|---|
| # of pts completed the 1# cycle treatment | 1 | 1 | 1 | 12 | 6 | 2 | 23 |
| # of pts discontinued treatment | 1 | 1 | 1 | 14 | 6 | 5 | 29 |
| Adverse Event | 0 | 0 | 0 | 1 | 1 | 1 | 3 |
| Disease progression | 1 | 1 | 0 | 8 | 2 | 2 | 14 |
| Lack of efficacy | 0 | 0 | 1 | 4 | 0 | 0 | 5 |
| Subject withdrawal | 0 | 0 | 0 | 0 | 1 | 2 | 3 |
| Other reason (clinical PD) | 0 | 0 | 0 | 2 | 2 | 0 | 4 |

Treatment Related AEs (all Grades)

TABLE 12 d

| Preferred Term, n(%) | 10 mg (n = 1) | 20 mg (n = 1) | 50 mg (n = 1) | 100 mg (n = 15) | 200 mg (n = 6) | 300 mg (n = 5) | Overall (n = 29) |
|---|---|---|---|---|---|---|---|
| Nausea | 0 | 1 (100.0%) | 0 | 8 (53.3%) | 1 (16.7%) | 3 (60.0%) | 13 (44.8%) |
| Fatigue | 0 | 1 (100.0%) | 0 | 6 (40.0%) | 2 (33.3%) | 3 (60.0%) | 12 (41.4%) |
| Vomiting | 0 | 0 | 0 | 5 (33.3%) | 2 (33.3%) | 2 (40.0%) | 9 (31.0%) |
| Decreased appetite | 0 | 0 | 1 (100.0%) | 3 (20.0%) | 1 (16.7%) | 1 (20.0%) | 6 (20.7%) |
| Platelet count decreased | 0 | 0 | 0 | 1 (6.7%) | 2 (33.3%) | 2 (40.0%) | 5 (17.2%) |
| Diarrhoea | 0 | 0 | 0 | 2 (13.3%) | 2 (33.3%) | 0 | 4 (13.8%) |
| Neutrophil count decreased | 0 | 0 | 0 | 0 | 2 (33.3%) | 1 (20.0%) | 3 (10.3%) |
| White blood cell count decreased | 0 | 0 | 0 | 0 | 2 (33.3%) | 1 (20.0%) | 3 (10.3%) |
| Anaemia | 0 | 0 | 0 | 1 (6.7%) | 1 (16.7%) | 0 | 2 (6.9%) |
| Dyspepsia | 0 | 0 | 0 | 2 (13.3%) | 0 | 0 | 2 (6.9%) |
| Alopecia | 0 | 0 | 0 | 0 | 1 (16.7%) | 0 | 1 (3.4%) |

TABLE 12 d-continued

| Preferred Term, n(%) | 10 mg (n = 1) | 20 mg (n = 1) | 50 mg (n = 1) | 100 mg (n = 15) | 200 mg (n = 6) | 300 mg (n = 5) | Overall (n = 29) |
|---|---|---|---|---|---|---|---|
| Constipation | 0 | 0 | 0 | 1 (6.7%) | 0 | 0 | 1 (3.4%) |
| Cystitis | 0 | 0 | 0 | 1 (6.7%) | 0 | 0 | 1 (3.4%) |
| Dehydration | 0 | 0 | 0 | 0 | 1 (16.7%) | 0 | 1 (3.4%) |
| Dry mouth | 0 | 0 | 1 (100.0%) | 0 | 0 | 0 | 1 (3.4%) |
| Dysgeusia | 0 | 0 | 0 | 1 (6.7%) | 0 | 0 | 1 (3.4%) |
| Haematuria | 0 | 0 | 0 | 1 (6.7%) | 0 | 0 | 1 (3.4%) |
| Hyponatraemia | 0 | 0 | 0 | 1 (6.7%) | 0 | 0 | 1 (3.4%) |
| Myalgia | 0 | 0 | 0 | 1 (6.7%) | 0 | 0 | 1 (3.4%) |
| Non-cardiac chest pain | 0 | 0 | 0 | 1 (6.7%) | 0 | 0 | 1 (3.4%) |
| Presyncope | 0 | 0 | 0 | 0 | 1 (16.7%) | 0 | 1 (3.4%) |
| Rash maculopapular | 0 | 0 | 0 | 1 (6.7%) | 0 | 0 | 1 (3.4%) |

Four DLTs were observed during cycle 1, including one G3 PLT decreased at 300 mg, one G3 nausea at 300 mg, and two G3 fatigue at 100 mg and 300 mg respectively (see Table 12(e)).

Figure 19:
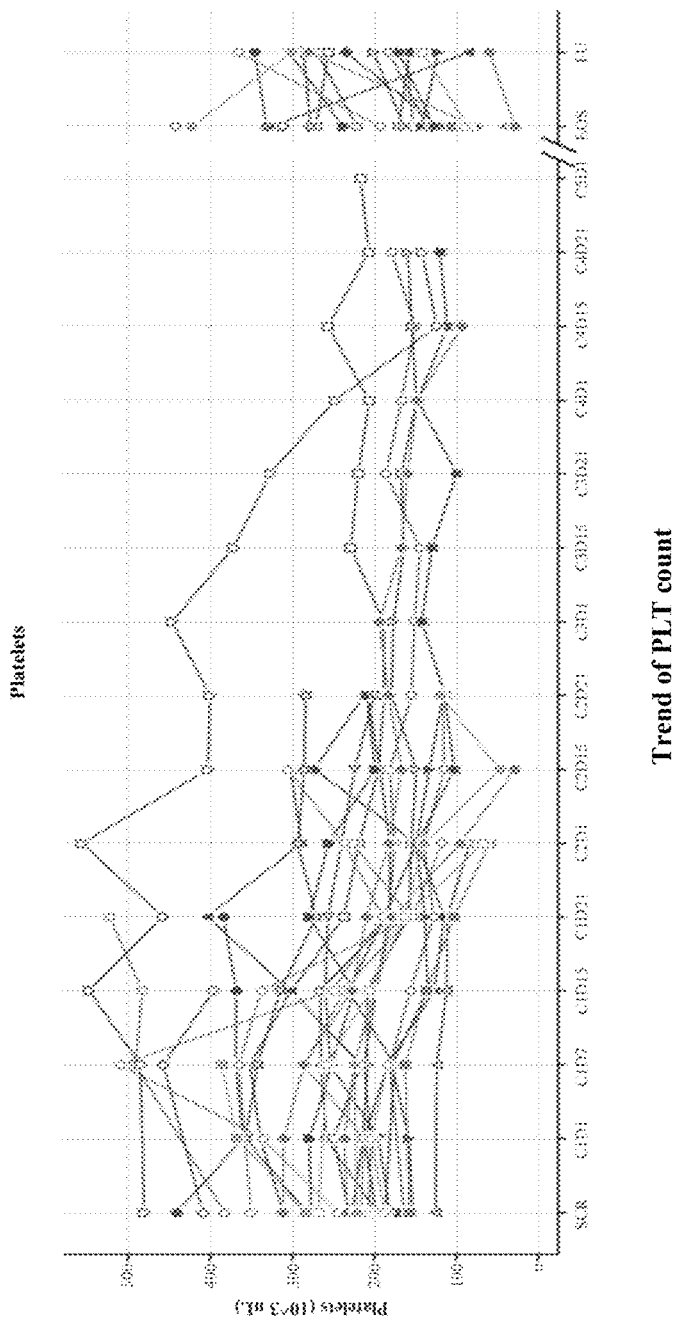
FIG. 19 illustrates the trend of PLT count change as one of the treatment related AEs.
Figure 20:
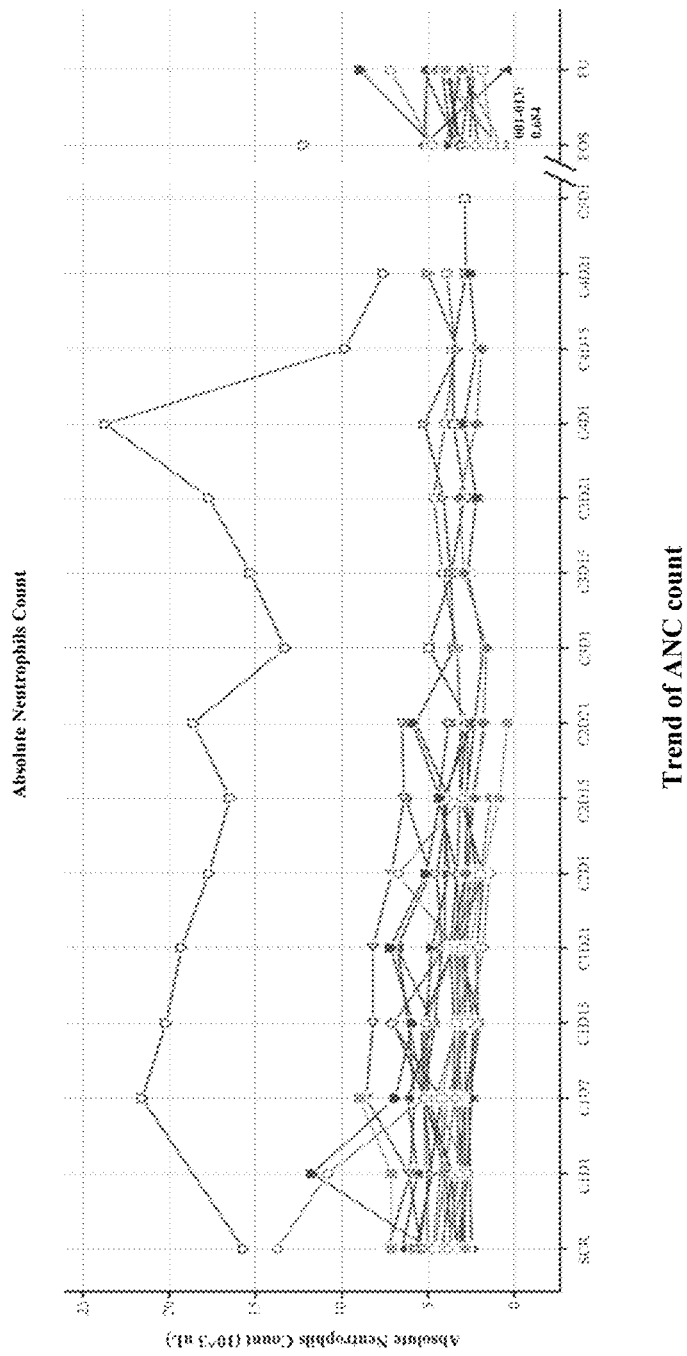
FIG. 20 illustrates trend of ANC count change as a one of the treatment related AEs.

FIG. 19 showed that two patients at 300 mg, two patients at 200 mg, and one patient at 100 mg had PLT count decreased (less than 100×10^3/uL) after C2D1. FIG. 20 showed that three patients had Absolute neutrophil count decreased (less than 1.00×10^3/uL) after C2D21. The MTD/RP2D of APG-115 monotherapy was determined as 100 mg.

Treatment Related AEs (at Least Grade 3)

TABLE 12 e

| Preferred Term, n(%) | 10 mg (n = 1) | 20 mg (n = 1) | 50 mg (n = 1) | 100 mg (n = 15) | 200 mg (n = 6) | 300 mg (n = 5) | Overall (n = 29) |
|---|---|---|---|---|---|---|---|
| Platelet count decreased | 0 | 0 | 0 | 1 (6.7%) | 1 (16.7%) | 2 (40.0%) | 4 (13.8%) |
| Fatigue | 0 | 0 | 0 | 1 (6.7%) | 1 (16.7%) | 1 (20.0%) | 3 (10.3%) |
| Neutrophil count decreased | 0 | 0 | 0 | 0 | 2 (33.3%) | 1 (20.0%) | 3 (10.3%) |
| White blood cell count decreased | 0 | 0 | 0 | 0 | 2 (33.3%) | 1 (20.0%) | 3 (10.3%) |
| Nausea | 0 | 0 | 0 | 0 | 0 | 2 (40.0%) | 2 (6.9%) |
| Anaemia | 0 | 0 | 0 | 0 | 1 (16.7%) | 0 | 1 (3.4%) |

Figure 21:
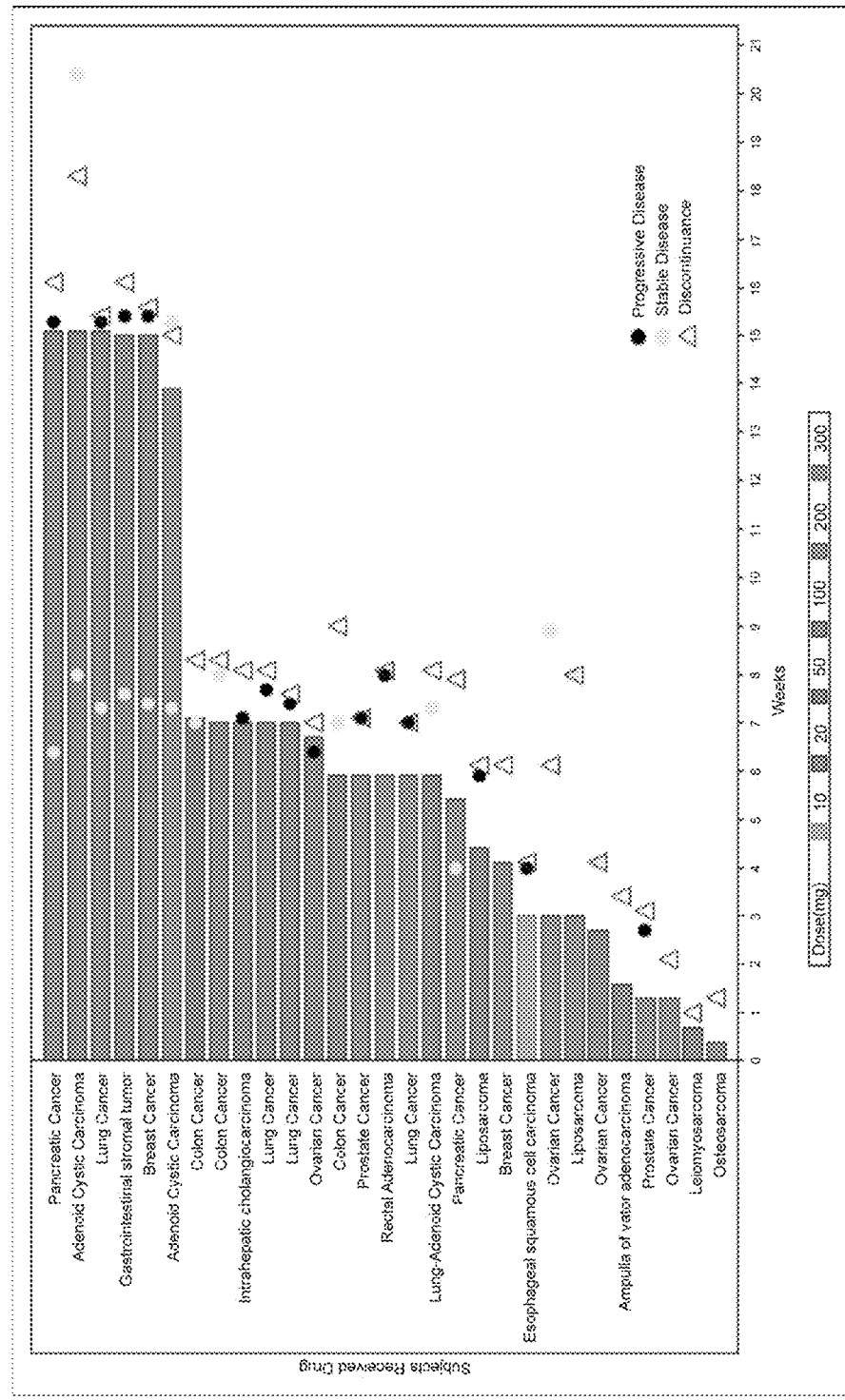
FIG. 21 illustrates treatment duration and response in various cancer patients.

The preliminary anti-tumor activity is shown in FIG. 21.

Figure 22:
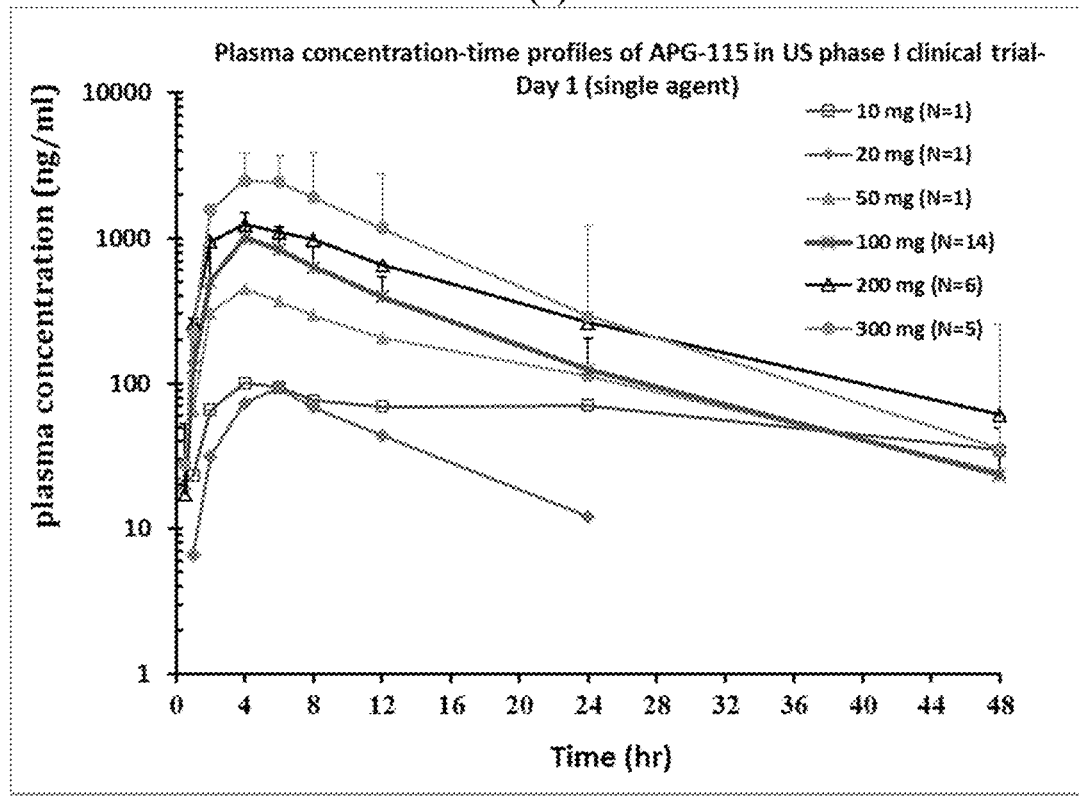
FIG. 22 illustrates plasma concentration-time profiles of APG-115 in the clinical trial on Day 1(a) or on Day 21(b).
Figure 22:
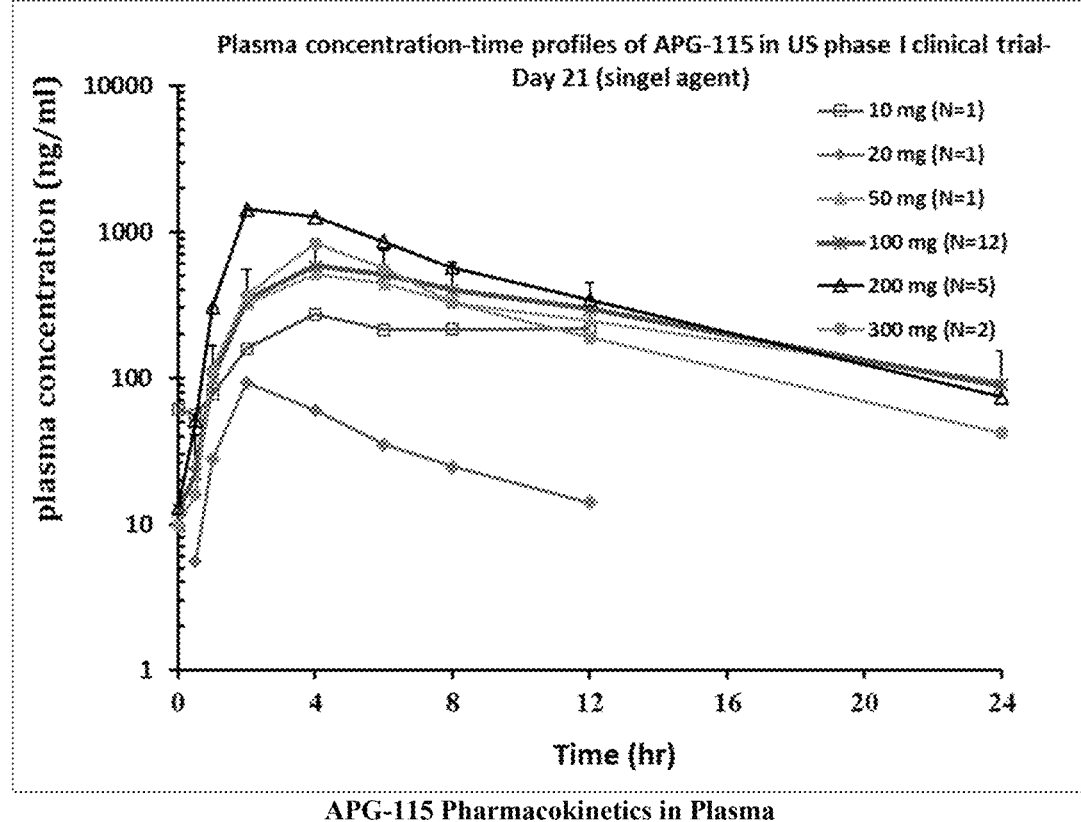
Figure 23:
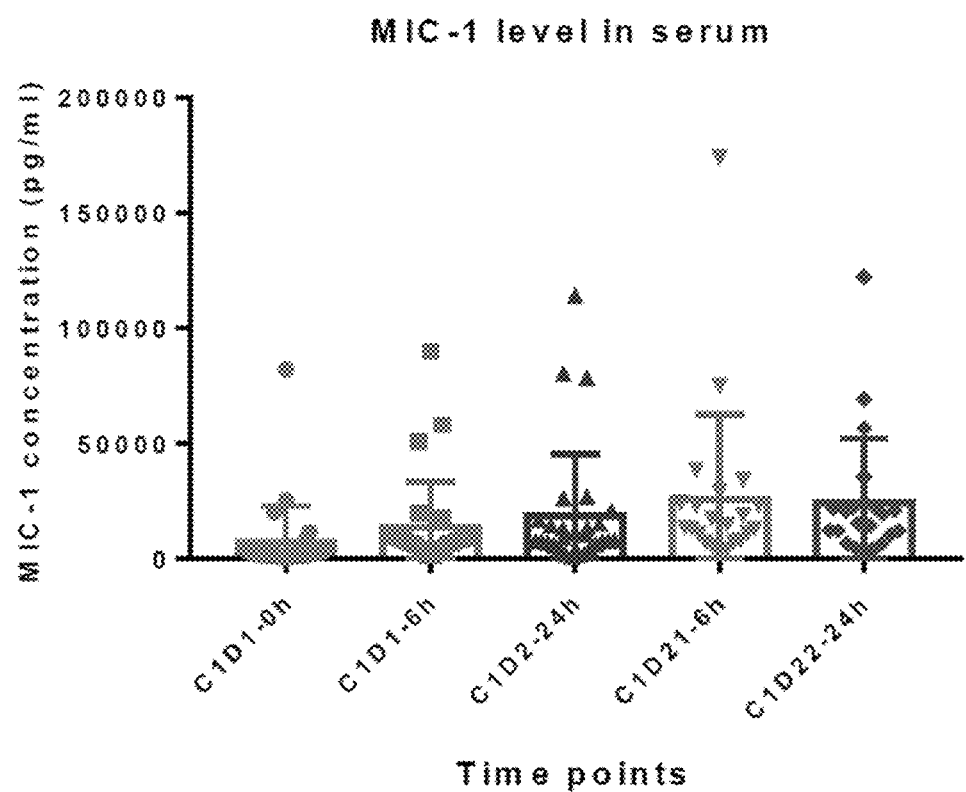
FIG. 23(*a*) and FIG. 23(*b*) illustrate that serum MIC-1 levels were elevated, and the increase was exposure dependent within the dose range tested in patients with solid tumors.
Figure 23:
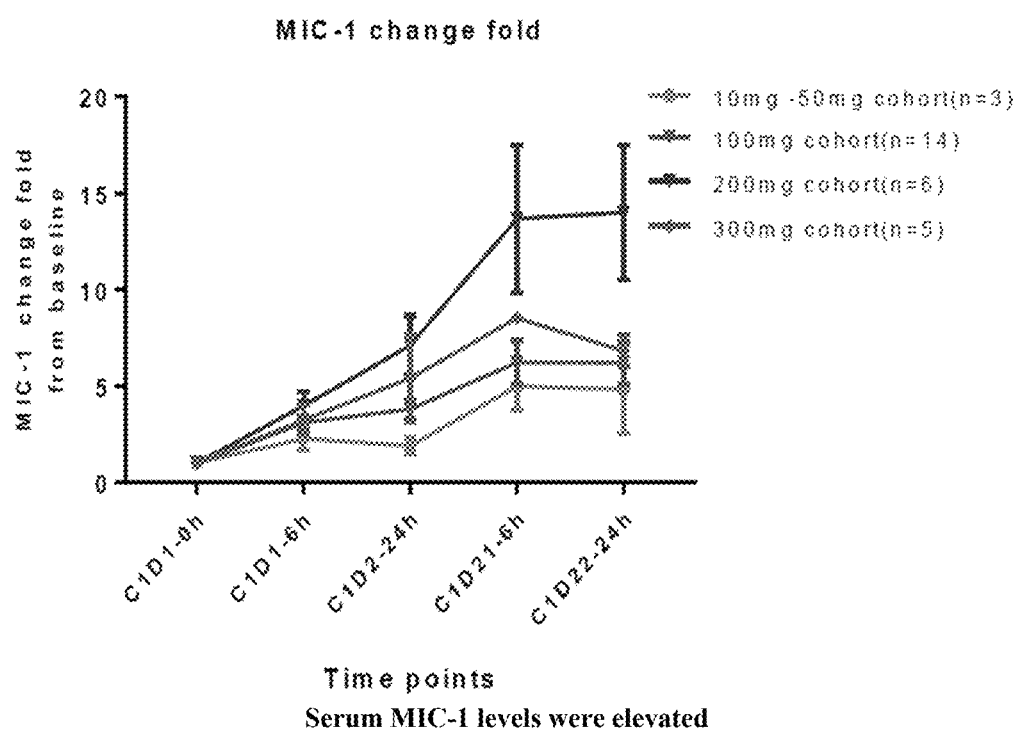
Figure 24:
FIG. 24 illustrates target lesion of the PR subject.

PK analyses have shown that AUC and Cmax generally increase dose proportionally over the dose range of 20-300 mg (see FIG. 22(a) and FIG. 22(b)). Serum MIC-1 (PD marker of TP53 activation) increase was exposure dependent within the dose range tested in pts with solid tumors (FIG. 23(a) and FIG. 23(b)). Further evaluation of APG-115 in combination with pembrolizumab in patients with advanced solid tumors is ongoing.

Example 8: A Phase I Study of a APG-115 in Chinese Patients with Advanced Soft Tissue Carcinoma APG-115 is a novel and orally active small-molecule MDM2 inhibitor. Binding to MDM2 protein, APG-115 restores p53 tumor suppressive function via induction of apoptosis in tumor cells retaining wild-type p53.

This is a Phase I study (CTR20170975) is designed to assess the safety, dose-limiting toxicities (DLT), the maximum tolerated dose (MTD)/recommended phase 2 dose (RP2D), pharmacokinetics (PK), pharmacodynamics (PD) profile and anti-tumor activity of orally administered APG-115 in Chinese patients with advanced soft tissue sarcoma and other solid tumors.

The primary objective of the study was to determine the safety and tolerability of APG-115, identify DLT, MTD/RP2D. The secondary objective of the study was to determine the PK, PD, anti-tumor effects of APG-115.

Single dose escalation study was conducted. A standard "3+3" design was employed to determine the maximum tolerated dose (MTD) of APG-115 by assessing the dose limiting toxicity (DLT) of APG-115. Three dose levels of APG-115 was tested: 100, 150, 200 mg. APG-115 was administrated orally every other day (QOD) for a consecutive 3 weeks (i.e. dosed at Day 1, 3, 5, 7, 9, 11, 13, 15, 17, 19, and 21), with one week dosing off as 4-weeks a cycle. 3 patients were enrolled per dose level, and if no patient shows DLT, then 3 patients were enrolled at the next dose level. The scheme of the trial design is provided below.

Phase I Dose Escalation Study: Standard "3+3" Design:

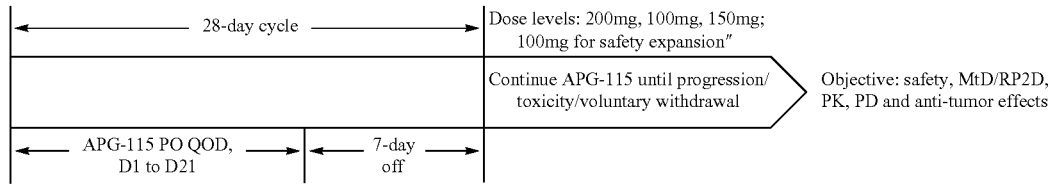

This study was conducted with an initial dosage of 200 mg, according to the preliminary safety results in phase I study of APG-115 in the US. As 2 DLTs were observed at 200 mg, a re-schedule of dose escalation from 100 mg was initiated, with no DLTs in 100 mg (n=3) and 150 mg (n=8) dose level. Due to the late onset hematologic toxicity at 150 mg in/after cycle 2, a safety expansion was conducted in 100 mg dose level.

The inclusion criteria for this study were:
1. Age≥18 years;
2. Confirmed advanced solid tumors, with no standard therapy judged appropriate by the investigator;
3. ECOG: 0-1;
4. Adequate renal, hepatic and hematologic function.

The exclusion criteria for this study were:
1. Any prior systemic MDM2-p53 inhibitor treatment;
2. Received standard or investigational anti-cancer therapy within 28 days or 5 half-lives prior to first dose of APG-115;
3. Has known active central nervous (CNS) metastases;
4. Uncontrolled concurrent or psychiatric illness/social situations that would limit compliance with the study requirements.

Baseline characteristics of pateints are shown in Tables 13(a) and 1(b)

TABLE 13 (a)

| Characteristic | APG-115 (N = 14) |
|---|---|
| Median Age, yrs(range) | 47.0 (26; 59) |
| Gender, n (%) | 9 (64.3%) |
| Male | 5 (35.7%) |
| Female | |
| ECOG, n (%) | |
| 0 | 0 |
| 1 | 14(100%) |
| # of prior anti-cancer therapies* | |
| 1 | 14 (100%) |
| ≥2 | 13 (92.9%) |
| TP53 Mutation status | 7(50.0%) |
| Wild type (WT), n (%) | 6(42.9%) |
| Mutation, n (%) | 1(7.1%) |
| Unkown, n (%) | 7(50.0%) |
| MDM2 Amplification (Amp), n (%) | 4(28.6%) |
| MDM2 Amp and TP53 WT, n (%) | |

TABLE 13 (b)

| Primary Cancer, n(%) | APG-115 (N = 14) |
|---|---|
| Sarcoma | 12 (85.7%) |
| Liposarcoma | 8 (57.1%) |
| Rhabdomyosarcoma | 1 (7.1%) |
| Synovial sarcoma | 1 (7.1%) |
| Chondrosarcoma | 1 (7.1%) |

TABLE 13 (b)-continued

| Primary Cancer, n(%) | APG-115 (N = 14) |
|---|---|
| Osteosarcoma | 1 (7.1%) |
| Adrenocortical carcinoma (ACC) | 2 (14.3%) |

TABLE 13 (c)

| Treatment Cycles | 100 mg (n = 4) | 150 mg (n = 8) | 200 mg (n = 2) | Total (n = 14) |
|---|---|---|---|---|
| <1 Cycle | 0 | 1(12.5%) | 1(50.0%) | 2 (14.3%) |
| 1 Cycle | 1(25.0%) | 1(12.5%) | 1(50.0%) | 3 (21.4%) |
| 2 Cycles | 3 (75.0%) | 3 (37.5%) | 0 | 6 (42.8%) |

TABLE 13 (c)-continued

| Treatment Cycles | 100 mg (n = 4) | 150 mg (n = 8) | 200 mg (n = 2) | Total (n = 14) |
|---|---|---|---|---|
| 3 Cycles | 0 | 1(12.5%) | 0 | 1 (7.2%) |
| >3 Cycles | 0 | 2 (25.0%) | 0 | 2 (14.3%) |

The safety study results are shown in Tables 13(d) and 1(e). Up until Apr. 23, 2019, 14 patients with advanced solid tumor (8 LPSs) received APG-115 ranging from 100-200 mg, qod, 21 days on 7 days off every 28 days.

TABLE 13 (d)

Most Common Adverse Events (frequency ≥2 pts)

| Preferred term/N | 100 mg (n = 4) | 150 mg (n = 8) | 200 mg (n = 2) | Total (n = 14) |
|---|---|---|---|---|
| Any AE | 4(100.0%) | 8 (100.0%) | 2 (100.0%) | 14 (100.0%) |
| Anaemia | 4 (100.0%) | 6 (75.0%) | 1 (50.0%) | 11 (78.6%) |
| Platelet count decreased | 1 (25.0%) | 6 (75.0%) | 2 (100.0%) | 9 (64.3%) |
| Hypercholesterolaemia | 1 (25.0%) | 7 (87.5%) | 0 | 8 (57.1%) |
| Vomiting | 2 (50.0%) | 5 (62.5%) | 1 (50.0%) | 8 (57.1%) |
| White blood cell count decreased | 0 | 6 (75.0%) | 1 (50.0%) | 7 (50.0%) |
| Hypoalbuminaemia | 4 (100.0%) | 3 (37.5%) | 0 | 7 (50.0%) |
| Hypertriglyceridaemia | 0 | 5 (62.5%) | 0 | 5 (35.7%) |
| Nausea | 1 (25.0%) | 3 (37.5%) | 1 (50.0%) | 5 (35.7%) |
| Neutrophil count decreased | 0 | 5 (62.5%) | 0 | 5 (35.7%) |
| Gamma-glutamyltransferase increased | 0 | 4 (50.0%) | 0 | 4 (28.6%) |
| Hyperuricaemia | 0 | 3 (37.5%) | 0 | 3 (21.4%) |
| Hypokalaemia | 0 | 3 (37.5%) | 0 | 3 (21.4%) |
| Oedemaperipheral | 2 (50.0%) | 1 (12.5%) | 0 | 3 (21.4%) |
| Abdominal distension | 2 (50.0%) | 0 | 0 | 2 (14.3%) |
| Abdominal pain | 1 (25.0%) | 1 (12.5%) | 0 | 2 (14.3%) |
| Asthenia | 0 | 2 (25.0%) | 0 | 2 (14.3%) |
| Blood alkaline phosphatase increased | 0 | 2 (25.0%) | 0 | 2 (14.3%) |
| Blood creatinine increased | 0 | 2 (25.0%) | 0 | 2 (14.3%) |
| Cancer pain | 0 | 2 (25.0%) | 0 | 2 (14.3%) |
| Decreased appetite | 1 (25.0%) | 0 | 1 (50.0%) | 2 (14.3%) |
| Febrile neutropenia | 0 | 1 (12.5%) | 1 (50.0%) | 2 (14.3%) |
| Headache | 1 (25.0%) | 1 (12.5%) | 0 | 2 (14.3%) |
| Insomnia | 1 (25.0%) | 0 | 1 (50.0%) | 2 (14.3%) |
| Low density lipoprotein increased | 0 | 2 (25.0%) | 0 | 2 (14.3%) |

TABLE 13 (e)

Grade 3 Adverse Events

| Preferred term/N | 100 mg (n = 4) | 150 mg (n = 8) | 200 mg (n = 2) | Total (n = 14) |
|---|---|---|---|---|
| Any AE | 1 (25.0%) | 7 (87.5%) | 2 (100.0%) | 10 (71.4%) |
| Platelet count decreased | 0 | 5 (62.5%) | 1 (50.0%) | 6 (42.9%) |
| Anaemia | 1 (25.0%) | 3 (37.5%) | 1 (50.0%) | 5 (35.7%) |
| Neutrophil count decreased | 0 | 4 (50.0%) | 0 | 4 (28.6%) |

TABLE 13 (e)-continued

Grade 3 Adverse Events

| Preferred term/N | 100 mg (n = 4) | 150 mg (n = 8) | 200 mg (n = 2) | Total (n = 14) |
|---|---|---|---|---|
| White blood cell count decreased | 0 | 3 (37.5%) | 1 (50.0%) | 4 (28.6%) |
| Febrile neutropenia | 0 | 1 (12.5%) | 1 (50.0%) | 2 (14.3%) |
| Vomiting | 0 | 2 (25.0%) | 0 | 2 (14.3%) |
| Blood creatinine increased | 0 | 1 (12.5%) | 0 | 1 (7.1%) |
| Dyspnoea | 0 | 1 (12.5%) | 0 | 1 (7.1%) |
| Lipase increased | 0 | 0 | 1 (50.0%) | 1 (7.1%) |
| Pulmonary embolism | 0 | 1 (12.5%) | 0 | 1 (7.1%) |
| Ureteric obstruction | 0 | 1 (12.5%) | 0 | 1 (7.1%) |

Two DLT were observed in one patient at 200 mg including thrombocytopenia and febrile neutropenia. No DLT was observed at 100 mg and 150 mg after 1 cycle of treatment, however late onset bone marrow suppression was observed in or after cycle 2 at 150 mg, safety expansion was ongoing at 100 mg. APG-115 was well-tolerated across all dose levels tested and the MTD was 150 mg, due to the late onset thrombocytopenia, the RP2D was 100 mg. The most common Grade 3 or 4 AEs were hematologic toxicities, particularly thrombocytopenia, which were predictable as the activation of p53 in the bone marrow.

Preliminary Anti-Tumor Activity

Among of the 14 patients, post baseline tumor measurements were obtained in 13 patients, as one subject was just starting the treatment of Cycle 2.

5 SD (Stable Disease):
1. Well-differentiation Liposarcoma patient (dose level: 200 mg; TP53-WT and MDM2 Amp): SD after cycle 1, withdraw due to G4 thrombocytopenia;
2. Synovial sarcoma patient (dose level: 100 mg; TP53-WT): SD after cycle 2;
3. Adrenocortical carcinoma patient (dose level: 150 mg; TP53-WT): SD after cycle 2, withdraw due to thrombocytopenia, maintained SD after 2 months withdraw;
4. Well-differentiation Liposarcoma patient (dose level: 150 mg; TP53-WT): SD after cycle 2;
5. Adrenocortical carcinoma patient (dose level: 150 mg; TP53-WT): SD after cycle 2, a confirmed SD after cycle 4.

1 confirmed PR(Partial Response): (dose level: 150 mg). One confirmed partial response was observed in 1 patient with lipomatoid liposarcoma at the 150 mg dose, and the duration of response has lasted after 4 months of treatment discontinuance.

1. Lipomatoid liposarcoma patient (TP53-WT and MDM2 Amp) with relapsed progressive disease after prior therapies: surgical excision and chemotherapy (AD: Adriamycin+ Dacarbazine, 5 cycles);
2. Imaging: the targeted lesion located among hepatic hilum, portacaval space decreased after 2 cycles of APG-115, withdraw on C4D15 (due to G4 thrombocytopenia) and PD after 1 month withdraw, magically a confirmed PR (best response) by RECIST criteria was observed after 4 months withdraw, target lesion decreased ~64%;

3. This patient denied taking any other anti-tumor agents during the study, due to the persistent thrombocytopenia, the patient is now under observation, whether the response dues to a legacy effect or immunological effect of APG-115 is still under investigation;
4. AEs: G4 Thrombocytopenia and G3 vomiting. Until the date of April 23, the G4 thrombocytopenia had degraded to G1.

Figure 25:
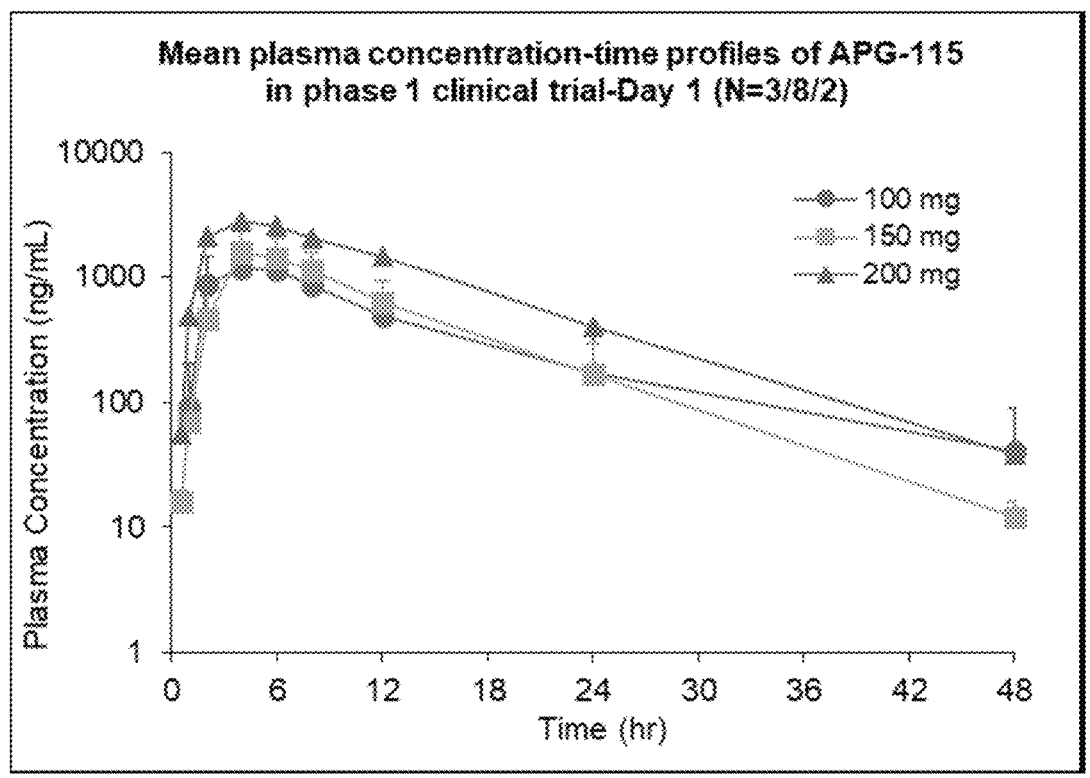
FIG. 25 illustrates the mean concentration-time profiles of APG-115 in phase I clinical trial on day 1(a) and on day 21(b).
Figure 25:
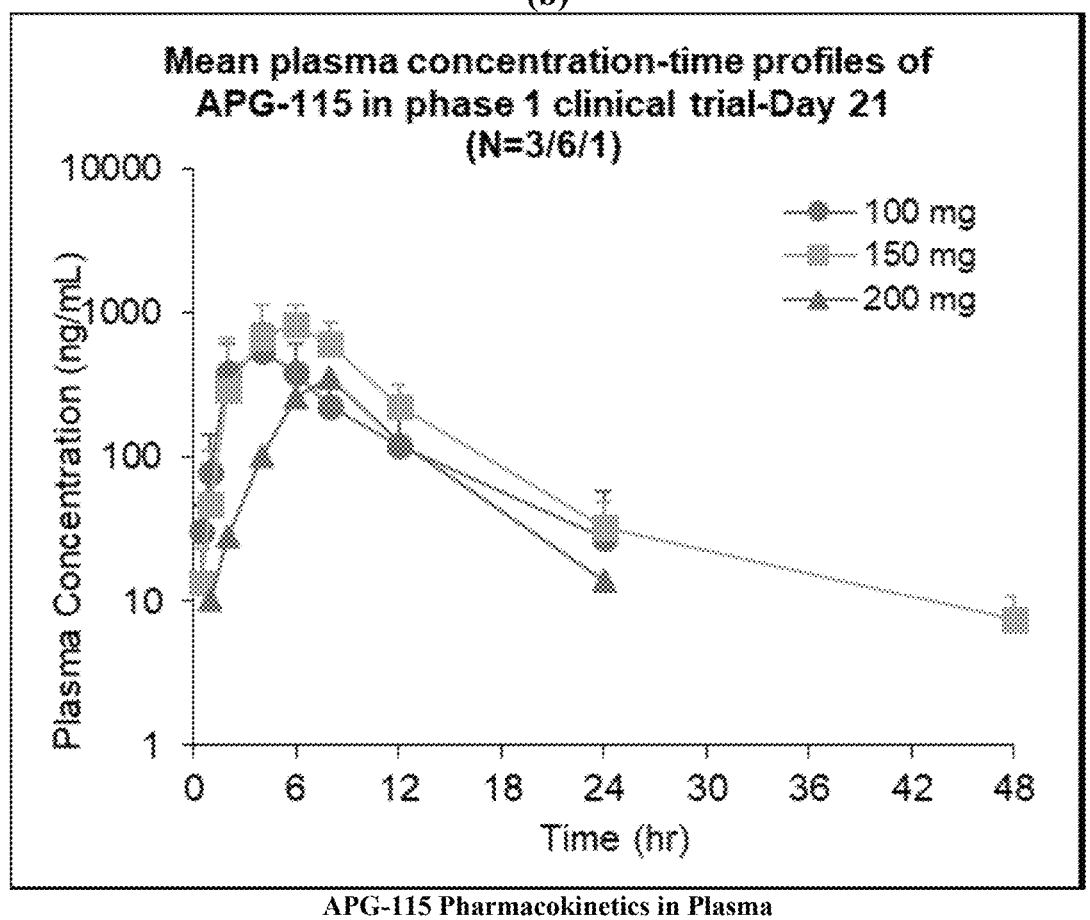
Figure 26:
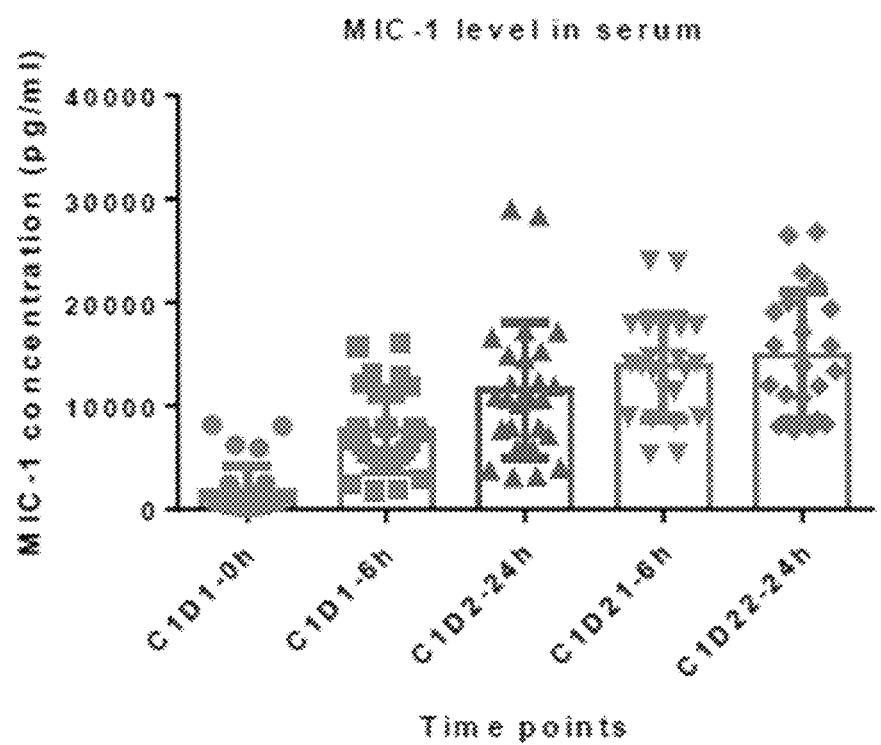
FIG. 26(*a*) and FIG. 26(*b*) illustrate that serum MIC-1 levels were elevated, and the increase was exposure dependent within the dose range tested in patients with solid tumors.
Figure 26:
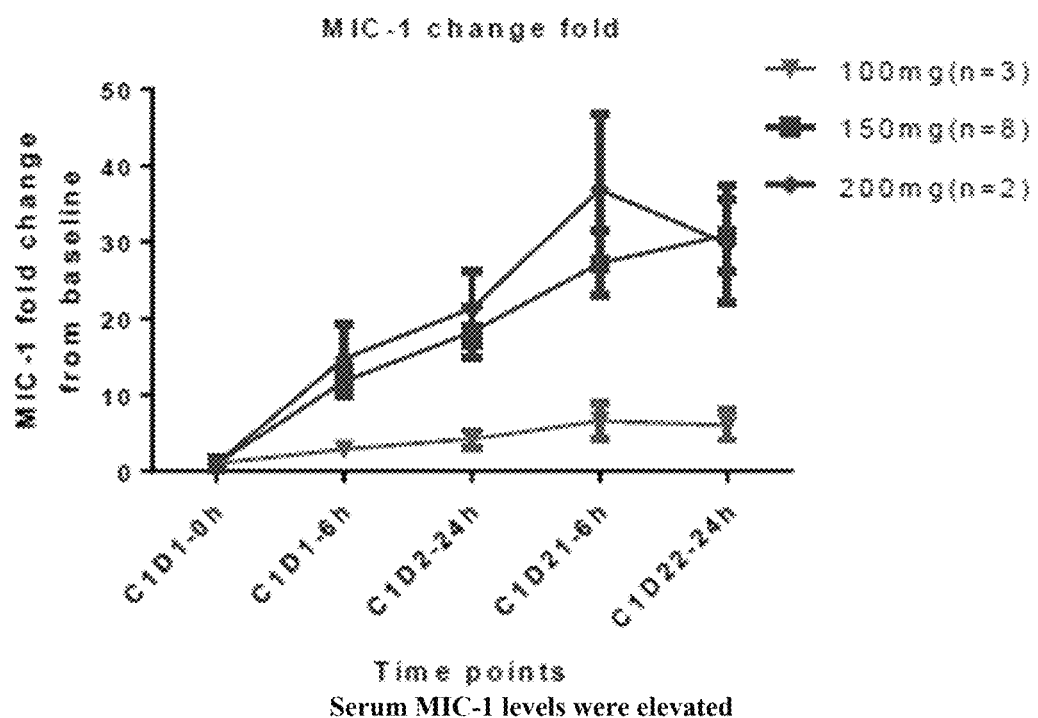

The preliminary anti-tumor activity is shown in FIG. 26. PK analyses have shown that AUC and Cmax generally increase dose proportionally over the dose range of 100-200 mg (see FIG. 25(a) and FIG. 25(b)). APG-115 displayed approximately linear pharmacokinetics over 100-200 mg range.

Serum MIC-1 (PD marker of TP53 activation) increase was exposure dependent within the dose range tested in pts with solid tumors (FIG. 26(a) and FIG. 26(b)).

Example 9. A Phase Ib/II Study of APG-115 in Combination with Pembrolizumab in Patients with Unresectable or Metastatic Melanomas or Advanced Solid Tumors Study Design The Ib/II study consists of two parts, a dose escalation study and a Simon two-stage phase II study.

In the dose escalation study, APG-115 is combined with pembrolizumab of for the treatment of patients with metastatic solid tumor. Four dose levels of APG-115 are tested: 50, 100, 150, and 200 mg. APG-115 is administrated orally every other day (QOD) for consecutive 2 weeks of a 21-day-cycle. Pembrolizumab is administrated at 200 mg IV on day 1 of a 21-day-cycle. The primary objectives of the dose escalation study is to determine safety, tolerability, and determination of MTD and RP2D; other anti-tumor assessments (assessed per RECIST v1.1 every 6 weeks) are the secondary objectives.

In the Simon two-stage phase II study, APG-115 at RP2D is combined with pembrolizumab in the patients with PD1/PD-L1 refractory/relapse melanoma. The primary objective of the study is to determine the overall response rate; the secondary objectives are the same as those of the dose escalation study.

Results

A total of 14 patients in dose escalation study had been treated in 4 cohorts of APG-115 (50 mg, 100 mg, 150 mg, 200 mg) in combination with pembrolizumab. No DLT was observed, and MTD is not reached. 11 patients experienced at least 1 TEAE, and 10 patients experienced at least 1 TRAE. The most common TRAEs (≥10%) were nausea (42.9%), neutrophil count decreased (21.4%), vomiting (14.3%), decreased appetite (14.3%), diarrhea (14.3%), platelet count decreased (14.3%), white blood cell count decreased (14.3%), and fatigue (14.3%). Four patients experienced at least 1 grade 3 or higher TRAE, neutrophil count decreased (21.4%) was the most common one (≥10%). Five SAEs occurred in 3 patients, but only one grade 3 febrile neutropenia was treatment related. One patient with advanced NSCLC in 100 mg cohort has received "confirmed PR" (still ongoing) after failed prior 6 lines therapies including 3 months' nivolumab treatment; 5 patients got "SD" after two cycle treatments, 2 of them has received "confirmed SD" (still ongoing). PK analysis indicated an approximately dose proportional increase in exposure across dose levels from 50 to 100 mg. Preliminary PD results showed that serum MIC-1 levels were elevated after APG-115 treatment, suggesting a potential p53 activation in patients.

CONCLUSION

APG-115 had manageable gastrointestinal and hematological toxicities, especially in higher dose level, when in combination with pembrolizumab. MTD is not reached. APG-115 has shown promising anti-tumor effects in several tumor types when in combination with pembrolizumab.

While the applicants have described a number of embodiments of this invention, it is apparent that these basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A method of treating liver cancer- or colon cancer, comprising administering to a subject in need thereof:
   a) an effective amount of a modulator of an immune checkpoint molecule; wherein the modulator of the immune checkpoint molecule is an anti-PD-1 antibody; and
   b) an effective amount of a MDM2 inhibitor, wherein the MDM2 inhibitor is represented by the following formula:

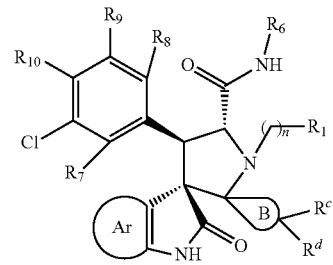

or a pharmaceutically acceptable salt thereof, wherein

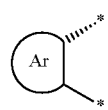

is selected from the group consisting of

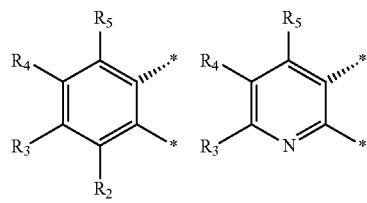

B is a C₄₋₇ carbocyclic ring;

R₁ is H, substituted or unsubstituted C₁₋₄ alkyl, substituted or unsubstituted cycloalkyl, substituted or unsubstituted heterocycloalkyl, OR$^a$, or NR$^a$R$^b$;

n is 0, 1, or 2;

R₂, R₃, R₄, R₅, R₇, R₈, R₉, and R₁₀, independently, are selected from the group consisting of H, F, Cl, CH₃, and CF₃;

R₆ is

R$^a$ is hydrogen or substituted or unsubstituted C₁₋₄ alkyl;

R$^b$ is hydrogen or substituted or unsubstituted C₁₋₄ alkyl;

R$^c$ and R$^d$ are substituents on one carbon atom of ring B, wherein

R$^e$ is H, C₁₋₃ alkyl, C₁₋₃ alkylene-OR$^a$, OR$^a$, or halo;

R$^d$ is H, C₁₋₃ alkyl, C₁₋₃ alkylene-OR$^a$, OR$^a$, or halo; or

R$^c$ and R$^d$ are taken together with the carbon to which they are attached to form a 4 to 6-membered Spiro substituent, optionally containing an oxygen atom; and R$^e$ is —C(=O) OR$^a$, —C(=O) NR$^a$R$^b$, or —C(=O) NHSO₂CH₃.

2. The method of claim 1, wherein the MDM2 inhibitor is selected from:

Compound E
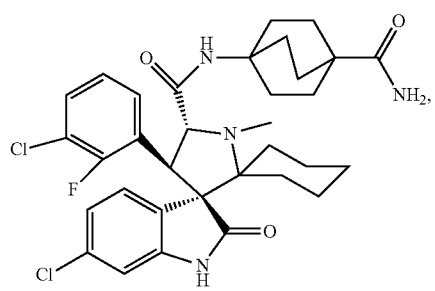
Compound C
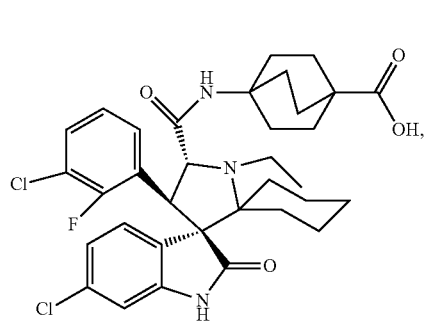
Compound F
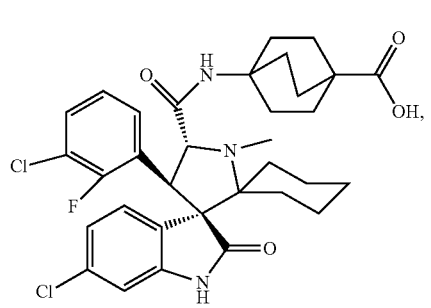
Compound Y
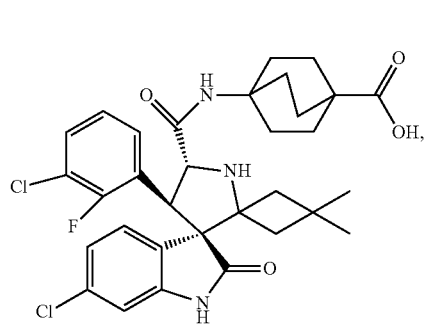
Compound K
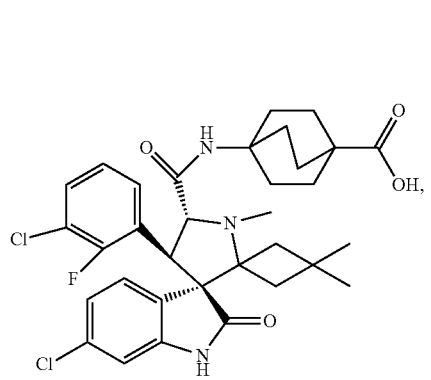
Compound P
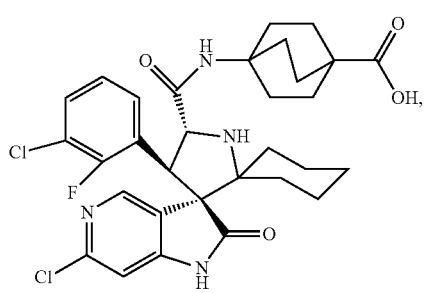
Compound T
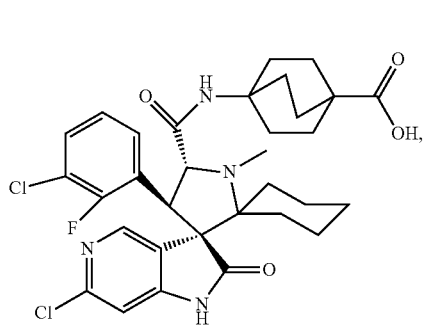
Compound S
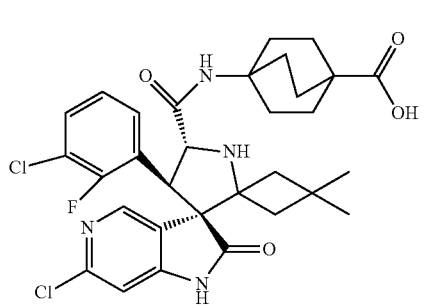
and
Compound W
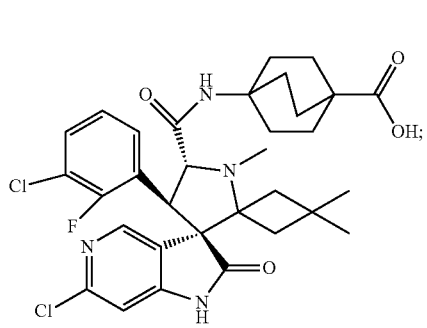
3. The method of claim 1, wherein the MDM2 inhibitor is
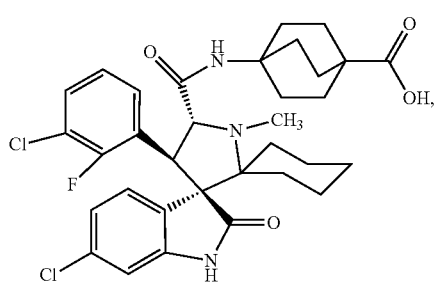 or -continued

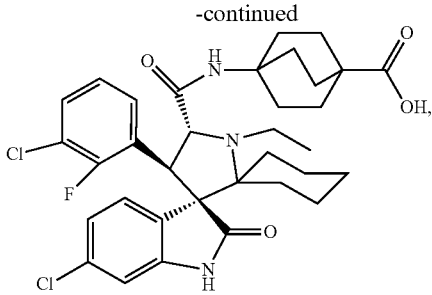

or a pharmaceutically acceptable salt thereof.

4. The method of claim 1, wherein the anti-PD-1 antibody is pembrolizumab, ipilimumab, nivolumab, atezolizumab, avelumab or durvalumab.

5. The method of claim 1, wherein the effective amount of a MDM2 inhibitor is from about 1 mg to about 300 mg.

6. The method of claim 1, wherein the MDM2 inhibitor is administered orally in an amount from about 30 mg to about 250 mg every other day, or about 50 mg to about 200 mg every other day.

7. The method of claim 1, wherein the anti-PD-1 antibody is administered via intravenous infusion in an amount of 200 mg on day 1 of a 21-day or 28-day treatment cycle.

8. The method of claim 1, wherein the method comprises at least one 21-day or 28-day treatment cycle, wherein the MDM2 inhibitor, or pharmaceutically acceptable salt thereof, is administered orally every other day in a patient in need thereof for the first two consecutive weeks of a 21-day or 28-day treatment cycle and is not administered during the third week of the treatment cycle; or the method comprises at least one 28-day treatment cycle, wherein the MDM2 inhibitor, or pharmaceutically acceptable salt thereof, is administered orally every other day in a patient in need thereof for the first three consecutive weeks of a 28-day treatment cycle and is not administered during the fourth week of the treatment cycle.

9. The method of claim 8, wherein the MDM2 inhibitor is administered orally in the patient in an amount from about 50 mg to about 200 mg on day 1, 3, 5, 7, 9, 11, and 13 of the 21-day treatment cycle; or wherein the MDM2 inhibitor is administered orally in the patient in an amount from about 50 mg to about 200 mg on day 1, 3, 5, 7, 9, 11, 13, 15, 17, 19, and 21 of the 28-day treatment cycle.

10. The method of claim 9, wherein the MDM2 inhibitor is administered orally in the patient in an amount of about 50 mg, about 100 mg, about 150 mg, or about 200 mg on day 1, 3, 5, 7, 9, 11, and 13 of the 21-day treatment cycle, or wherein the MDM2 inhibitor is administered orally in the patient in an amount of about 50 mg, about 100 mg, about 150 mg, or about 200 mg on day 1, 3, 5, 7, 9, 11, 13, 15, 17, 19, and 21 of the 28-day treatment cycle.

11. The method of claim 8, wherein the patient is refractory or relapse of or resistant to anti-PD-1 therapy.

12. The method of claim 8, wherein the patient is suffering from advanced solid tumors.

13. A method for treating hyper-progression in a patient receiving anti-PD-1/PD-L1 therapy for the treatment of liver cancer, wherein the method comprises administering to the patient in need thereof a therapeutically effective amount of a MDM2 inhibitor, wherein the MDM2 inhibitor is

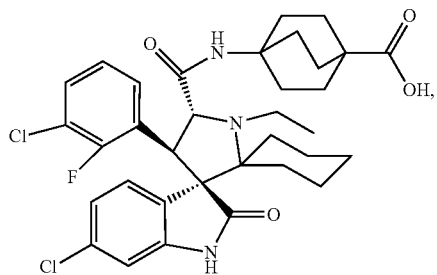 [SMILES: CCN1[C@@H](C(=O)NC23CCC(C(=O)O)(CC2)CC3)[C@H](c2cccc(Cl)c2F)[C@]2(C(=O)Nc3cc(Cl)ccc32)C12CCCCC2]

or a pharmaceutically acceptable salt thereof.

* * * * *